United States Patent
Zeidan et al.

(10) Patent No.: US 11,083,703 B2
(45) Date of Patent: Aug. 10, 2021

(54) PRODRUGS OF FUMARATES AND THEIR USE IN TREATING VARIOUS DISEASES

(71) Applicant: Alkermes Pharma Ireland Limited, Dublin (IE)

(72) Inventors: Tarek A. Zeidan, Lexington, MA (US); Scott Duncan, Bedford, MA (US); Christopher P. Hencken, Boston, MA (US); Thomas Andrew Wynn, Lexington, MA (US); Carlos N. Sanrame, Lexington, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 16/790,849

(22) Filed: Feb. 14, 2020

(65) Prior Publication Data
US 2020/0352893 A1     Nov. 12, 2020

Related U.S. Application Data

(63) Continuation of application No. 16/524,498, filed on Jul. 29, 2019, now Pat. No. 10,596,140, which is a continuation of application No. 16/145,703, filed on Sep. 28, 2018, now Pat. No. 10,406,133, which is a continuation of application No. 15/704,219, filed on Sep. 14, 2017, now Pat. No. 10,117,846, which is a continuation of application No. 15/295,370, filed on Oct. 17, 2016, now Pat. No. 9,775,823, which is a continuation of application No. 14/212,745, filed on Mar. 14, 2014, now Pat. No. 9,505,776.

(60) Provisional application No. 61/934,365, filed on Jan. 31, 2014, provisional application No. 61/782,445, filed on Mar. 14, 2013.

(51) Int. Cl.
| | |
|---|---|
| C07C 235/88 | (2006.01) |
| A61K 31/225 | (2006.01) |
| C07D 491/113 | (2006.01) |
| C07C 317/28 | (2006.01) |
| C07D 211/38 | (2006.01) |
| C07D 295/088 | (2006.01) |
| C07D 207/40 | (2006.01) |
| C07D 211/06 | (2006.01) |
| C07D 207/06 | (2006.01) |
| C07D 209/52 | (2006.01) |
| C07C 317/18 | (2006.01) |
| C07C 219/08 | (2006.01) |
| C07C 229/16 | (2006.01) |
| C07C 233/18 | (2006.01) |
| C07C 233/91 | (2006.01) |

(52) U.S. Cl.
CPC .......... *A61K 31/225* (2013.01); *C07C 219/08* (2013.01); *C07C 229/16* (2013.01); *C07C 233/18* (2013.01); *C07C 233/91* (2013.01); *C07C 235/88* (2013.01); *C07C 317/18* (2013.01); *C07C 317/28* (2013.01); *C07D 207/06* (2013.01); *C07D 207/40* (2013.01); *C07D 209/52* (2013.01); *C07D 211/06* (2013.01); *C07D 211/38* (2013.01); *C07D 295/088* (2013.01); *C07D 491/113* (2013.01)

(58) Field of Classification Search
CPC .................................................... C07C 235/88
See application file for complete search history.

(56) References Cited

U.S. PATENT DOCUMENTS

| | | |
|---|---|---|
| 2,723,967 A | 11/1955 | Thomas |
| 3,336,364 A | 8/1967 | Robert |
| 3,580,918 A | 5/1971 | Bodnarjuk et al. |
| 3,832,287 A | 8/1974 | Gale et al. |
| 3,892,671 A | 7/1975 | Song |
| 4,515,974 A | 5/1985 | Zecher et al. |
| 4,639,273 A | 1/1987 | Gilmore et al. |
| 4,746,668 A | 5/1988 | Sato et al. |
| 4,753,935 A | 6/1988 | Nelson et al. |
| 4,801,597 A | 1/1989 | Stacpoole et al. |
| 4,851,439 A | 7/1989 | Speiser et al. |
| 4,894,366 A | 1/1990 | Okuhara et al. |
| 4,959,389 A | 9/1990 | Speiser et al. |
| 5,073,641 A | 12/1991 | Bundgaard et al. |
| 5,149,695 A | 9/1992 | Speiser et al. |
| 5,214,196 A | 5/1993 | Blank |
| 5,242,905 A | 9/1993 | Blank |
| 5,278,314 A | 1/1994 | Winter et al. |
| 5,334,456 A | 8/1994 | Noren et al. |

(Continued)

FOREIGN PATENT DOCUMENTS

| | | |
|---|---|---|
| CA | 2248955 A1 | 5/1997 |
| CA | 2864040 A1 | 8/2013 |

(Continued)

OTHER PUBLICATIONS

CAS RN 25254-52-8; Entered STN: Nov. 16, 1984.

(Continued)

*Primary Examiner* — Laura L Stockton
(74) *Attorney, Agent, or Firm* — Elmore Patent Law Group, P.C.; Carolyn Elmore; Joseph Zucchero

(57) ABSTRACT

The present invention provides compounds of formula (I), and pharmaceutical compositions thereof.

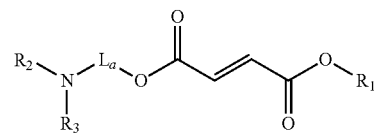

4 Claims, 7 Drawing Sheets

(56) References Cited

U.S. PATENT DOCUMENTS

| | | | |
|---|---|---|---|
| 5,359,128 A | 10/1994 | Blank | |
| 5,424,332 A | 6/1995 | Speiser et al. | |
| 5,451,667 A | 9/1995 | Speiser et al. | |
| 5,534,250 A | 7/1996 | Klaveness et al. | |
| 5,538,968 A | 7/1996 | Chiesi et al. | |
| 5,543,408 A | 8/1996 | Fu et al. | |
| 5,548,059 A | 8/1996 | Bayley et al. | |
| 5,589,504 A | 12/1996 | Dannenberg et al. | |
| 5,650,492 A | 7/1997 | Gately et al. | |
| 5,688,529 A | 11/1997 | Lidgate et al. | |
| 5,723,558 A | 3/1998 | Oishi et al. | |
| 5,877,180 A | 3/1999 | Linden et al. | |
| 5,972,363 A | 10/1999 | Guo et al. | |
| 5,977,219 A | 11/1999 | Ravichandran et al. | |
| 6,025,391 A | 2/2000 | Mak et al. | |
| 6,040,455 A | 3/2000 | Wood et al. | |
| 6,087,540 A | 7/2000 | Kamigauchi et al. | |
| 6,166,218 A | 12/2000 | Wolf et al. | |
| 6,172,107 B1 | 1/2001 | Meinzer et al. | |
| 6,245,915 B1 | 6/2001 | Ravichandran et al. | |
| 6,277,882 B1 | 8/2001 | Joshi et al. | |
| 6,306,900 B1 | 10/2001 | Meinzer et al. | |
| 6,355,676 B1 | 3/2002 | Joshi et al. | |
| 6,359,003 B1 | 3/2002 | Joshi et al. | |
| 6,436,992 B1 | 8/2002 | Joshi et al. | |
| 6,509,376 B1 | 1/2003 | Joshi et al. | |
| 6,525,046 B1 | 2/2003 | Cirillo et al. | |
| 6,645,524 B2 | 11/2003 | Midha et al. | |
| 6,858,750 B2 | 2/2005 | Joshi et al. | |
| 7,157,423 B2 | 1/2007 | Joshi et al. | |
| 7,320,999 B2 | 1/2008 | Joshi et al. | |
| 7,432,240 B2 | 10/2008 | Joshi et al. | |
| 7,612,110 B2 | 11/2009 | Joshi et al. | |
| 7,619,001 B2 | 11/2009 | Joshi et al. | |
| 7,638,118 B2 | 12/2009 | Flachsmann et al. | |
| 7,790,916 B2 | 9/2010 | Joshi et al. | |
| 7,803,840 B2 | 9/2010 | Joshi et al. | |
| 7,906,659 B2 | 3/2011 | Joshi et al. | |
| 7,915,310 B2 | 3/2011 | Joshi et al. | |
| 8,067,467 B2 | 11/2011 | Joshi et al. | |
| 8,148,414 B2 | 4/2012 | Zerangue et al. | |
| 8,399,514 B2 | 3/2013 | Lukashev et al. | |
| 8,524,773 B2 | 9/2013 | Joshi et al. | |
| 8,669,281 B1 | 3/2014 | Duncan et al. | |
| 9,090,558 B2 | 7/2015 | Duncan et al. | |
| 9,102,649 B1 | 8/2015 | Kandula | |
| 9,505,776 B2 | 11/2016 | Duncan et al. | |
| 9,775,823 B2 | 10/2017 | Zeidan et al. | |
| 2002/0035175 A1 | 3/2002 | Wood et al. | |
| 2003/0004235 A1 | 1/2003 | Wood et al. | |
| 2003/0013761 A1 | 1/2003 | Joshi et al. | |
| 2003/0018072 A1 | 1/2003 | Joshi et al. | |
| 2003/0135172 A1 | 7/2003 | Whitmore et al. | |
| 2004/0038889 A1 | 2/2004 | Joshi et al. | |
| 2004/0054001 A1 | 3/2004 | Joshi et al. | |
| 2004/0102525 A1 | 5/2004 | Kozachuk | |
| 2005/0044644 A1 | 3/2005 | Pearson et al. | |
| 2005/0096369 A1 | 5/2005 | Hoang | |
| 2005/0101779 A1 | 5/2005 | Sagi et al. | |
| 2005/0148664 A1 | 7/2005 | Joshi et al. | |
| 2006/0002869 A1 | 1/2006 | Bonda et al. | |
| 2006/0069161 A1 | 3/2006 | Lee et al. | |
| 2006/0205659 A1 | 9/2006 | Joshi et al. | |
| 2007/0027076 A1 | 2/2007 | Joshi et al. | |
| 2007/0207331 A1 | 9/2007 | Pearson et al. | |
| 2007/0208087 A1 | 9/2007 | Sanders et al. | |
| 2007/0248662 A1 | 10/2007 | Joshi et al. | |
| 2007/0248663 A1 | 10/2007 | Joshi et al. | |
| 2007/0253902 A1 | 11/2007 | Lobb et al. | |
| 2008/0004344 A1 | 1/2008 | Nilsson et al. | |
| 2008/0089861 A1 | 4/2008 | Went et al. | |
| 2008/0227847 A1 | 9/2008 | Nilsson et al. | |
| 2008/0233185 A1 | 9/2008 | Joshi et al. | |
| 2008/0299196 A1 | 12/2008 | Nilsson et al. | |
| 2008/0300217 A1 | 12/2008 | Nilsson | |
| 2009/0011986 A1 | 1/2009 | Joshi et al. | |
| 2009/0181085 A1 | 7/2009 | Joshi et al. | |
| 2009/0182047 A1 | 7/2009 | Joshi et al. | |
| 2009/0304790 A1 | 12/2009 | Nilsson et al. | |
| 2010/0048651 A1 | 2/2010 | Gangakhedkar et al. | |
| 2010/0130607 A1 | 5/2010 | Gold | |
| 2010/0144651 A1 | 6/2010 | Nilsson et al. | |
| 2010/0316706 A1 | 12/2010 | Joshi et al. | |
| 2011/0080547 A1 | 4/2011 | Matsumori et al. | |
| 2011/0112196 A1 | 5/2011 | Lukashev | |
| 2011/0124615 A1 | 5/2011 | Joshi et al. | |
| 2012/0196931 A1 | 8/2012 | Lukashev et al. | |
| 2012/0202756 A1 | 8/2012 | Franklin et al. | |
| 2012/0259012 A1 | 10/2012 | Lukashev | |
| 2013/0004526 A1 | 1/2013 | Joshi et al. | |
| 2013/0158077 A1 | 6/2013 | Kahrs | |
| 2013/0203753 A1 | 8/2013 | Cundy et al. | |
| 2013/0216615 A1 | 8/2013 | Goldman | |
| 2013/0283349 A1 | 10/2013 | Liu et al. | |
| 2013/0287732 A1 | 10/2013 | Goelz et al. | |
| 2013/0324539 A1 | 12/2013 | Virsik et al. | |
| 2014/0056973 A1 | 2/2014 | Ma et al. | |
| 2014/0056978 A1 | 2/2014 | Karabomi et al. | |
| 2014/0057917 A1 | 2/2014 | Cundy et al. | |
| 2014/0057918 A1 | 2/2014 | Wustrow et al. | |
| 2014/0065211 A1 | 3/2014 | Karabomi et al. | |
| 2014/0179778 A1 | 6/2014 | Mao et al. | |
| 2014/0194427 A1 | 7/2014 | Chao | |
| 2014/0275250 A1 | 9/2014 | Cundy | |
| 2014/0284245 A1 | 9/2014 | Karabomi et al. | |
| 2014/0329818 A1 | 11/2014 | Gangakhedkar et al. | |
| 2014/0364604 A1 | 12/2014 | Raillard et al. | |
| 2014/0378542 A1 | 12/2014 | Mao et al. | |
| 2015/0038499 A1 | 2/2015 | Virsik | |
| 2015/0073049 A1 | 3/2015 | Mao et al. | |
| 2015/0079180 A1 | 3/2015 | Karabomi et al. | |
| 2015/0190360 A1 | 7/2015 | Cundy | |
| 2016/0137660 A1 | 5/2016 | Duncan et al. | |

FOREIGN PATENT DOCUMENTS

| | | |
|---|---|---|
| CA | 2882730 A1 | 2/2014 |
| CN | 101774913 A | 7/2010 |
| DE | 3524542 A1 | 1/1987 |
| DE | 3524543 A1 | 1/1987 |
| DE | 3532035 A1 | 3/1987 |
| DE | 3609361 A1 | 3/1987 |
| DE | 19750906 A1 | 5/1998 |
| DE | 10206097 A1 | 8/2003 |
| EP | 0133164 A2 | 2/1985 |
| EP | 300688 A1 | 1/1989 |
| EP | 326974 A1 | 8/1989 |
| EP | 466640 A1 | 1/1992 |
| EP | 469481 A1 | 2/1992 |
| EP | 667339 A1 | 8/1995 |
| EP | 928820 A2 | 7/1999 |
| EP | 0928820 A2 | 7/1999 |
| EP | 970945 A1 | 1/2000 |
| EP | 1123915 A1 | 8/2001 |
| EP | 1230919 A2 | 8/2002 |
| GB | 1206359 A | 9/1970 |
| GB | 1404989 A | 9/1975 |
| GB | 2285805 A | 7/1995 |
| JP | 48007082 | 1/1973 |
| JP | 48-42083 | 6/1973 |
| JP | 61283694 A | 12/1986 |
| JP | 62199643 U | 9/1987 |
| JP | 02214731 A | 8/1990 |
| JP | 8005969 A | 1/1996 |
| JP | 2000513023 A | 10/2000 |
| JP | 2002249471 A | 9/2002 |
| JP | 2007061155 A | 3/2007 |
| JP | 2007186512 A | 7/2007 |
| JP | 2008156334 A | 7/2008 |
| JP | 2009510137 A | 3/2009 |
| JP | 2010260840 A | 11/2010 |
| JP | 2011231094 A | 11/2011 |
| KR | 10-2014-0129136 A | 11/2014 |
| WO | 8603741 A1 | 7/1986 |

(56) References Cited

FOREIGN PATENT DOCUMENTS

| | | |
|---|---|---|
| WO | 9214717 A1 | 9/1992 |
| WO | 9214718 A1 | 9/1992 |
| WO | 9503827 A1 | 2/1995 |
| WO | 9516668 A1 | 6/1995 |
| WO | 9613495 A1 | 5/1996 |
| WO | 9708177 A1 | 3/1997 |
| WO | 9732578 A1 | 9/1997 |
| WO | 9738983 A1 | 10/1997 |
| WO | 9749685 A1 | 12/1997 |
| WO | 9804290 A2 | 2/1998 |
| WO | 9827191 A1 | 6/1998 |
| WO | 9829114 A1 | 7/1998 |
| WO | 9852549 A2 | 11/1998 |
| WO | 9906378 A1 | 2/1999 |
| WO | 9906396 A1 | 2/1999 |
| WO | 9949858 A1 | 10/1999 |
| WO | 9951191 A1 | 10/1999 |
| WO | 9962973 A1 | 12/1999 |
| WO | 0010560 A1 | 3/2000 |
| WO | 0012072 A2 | 3/2000 |
| WO | 0018391 A1 | 4/2000 |
| WO | 0030622 A2 | 6/2000 |
| WO | 0066676 A1 | 11/2000 |
| WO | 0151047 A1 | 7/2001 |
| WO | 0196281 A1 | 12/2001 |
| WO | 0211205 A1 | 2/2002 |
| WO | 0212202 A2 | 2/2002 |
| WO | 0212204 A1 | 2/2002 |
| WO | 02055063 A2 | 7/2002 |
| WO | 02055066 A1 | 7/2002 |
| WO | 02081466 A1 | 10/2002 |
| WO | 03046017 A1 | 6/2003 |
| WO | 03048257 A1 | 6/2003 |
| WO | 03070819 A1 | 8/2003 |
| WO | 03091287 A1 | 11/2003 |
| WO | 2004039787 A1 | 5/2004 |
| WO | 2005021051 A1 | 3/2005 |
| WO | 2006037342 A2 | 4/2006 |
| WO | 2006050730 A1 | 5/2006 |
| WO | 2006129199 A1 | 12/2006 |
| WO | 2006131649 A2 | 12/2006 |
| WO | 2007006308 A1 | 1/2007 |
| WO | 2007020631 A2 | 2/2007 |
| WO | 2007033418 A1 | 3/2007 |
| WO | 2007042034 A1 | 4/2007 |
| WO | 2007042035 A2 | 4/2007 |
| WO | 2008000646 A1 | 1/2008 |
| WO | 2008016692 A2 | 2/2008 |
| WO | 2008049257 A1 | 5/2008 |
| WO | 2008096271 A2 | 8/2008 |
| WO | 2008145705 A1 | 12/2008 |
| WO | 2009030649 A2 | 3/2009 |
| WO | 2010002625 A1 | 1/2010 |
| WO | 2010022177 A2 | 2/2010 |
| WO | 2010079222 A1 | 7/2010 |
| WO | 2011085211 A1 | 7/2011 |
| WO | 2011112662 A1 | 9/2011 |
| WO | 2011146326 A1 | 11/2011 |
| WO | 2012004414 A2 | 1/2012 |
| WO | 2012014162 A1 | 2/2012 |
| WO | 2012018682 A1 | 2/2012 |
| WO | 2012046062 A1 | 4/2012 |
| WO | 2012117421 A1 | 9/2012 |
| WO | 2012122383 A2 | 9/2012 |
| WO | 2012129112 A2 | 9/2012 |
| WO | 2012162669 A1 | 11/2012 |
| WO | 2012170923 A1 | 12/2012 |
| WO | 2013022996 A2 | 2/2013 |
| WO | 2013024040 A2 | 2/2013 |
| WO | 2013076216 A1 | 5/2013 |
| WO | 2013090799 A1 | 6/2013 |
| WO | 2013119677 A1 | 8/2013 |
| WO | 2013119791 A1 | 8/2013 |
| WO | 2013150529 A2 | 10/2013 |
| WO | 2013181451 A1 | 12/2013 |
| WO | 2014031844 A1 | 2/2014 |
| WO | 2014031892 A1 | 2/2014 |
| WO | 2014031894 A1 | 2/2014 |
| WO | 2014068506 A2 | 5/2014 |
| WO | 2014096425 A2 | 6/2014 |
| WO | 2014100728 A1 | 6/2014 |
| WO | 2014152494 A1 | 9/2014 |
| WO | 2014195850 A2 | 12/2014 |
| WO | 2015082590 A2 | 6/2015 |
| WO | 2017108960 A1 | 6/2017 |
| WO | 2019022177 A1 | 1/2019 |

OTHER PUBLICATIONS

CAS RN 82246-13-7; Entered STN: Nov. 16, 1984.
CAS RN 86147-71-9; Entered STN: Nov. 16, 1984.
Center for Drug Evaluation and Research. Tecfidera Addendum to Biopharmaceutics Review for Application No. 204063Orig1s000, Dated Feb. 12, 2013.
Center for Drug Evaluation and Research. Tecfidera Administrative and Correspondence Documents for Application No. 204063Orig1s000, Dated Aug. 30, 2006-Mar. 27, 2013.
Center for Drug Evaluation and Research. Tecfidera Approval Letter for Application No. 204063Orig1s000, Dated Mar. 27, 2013.
Center for Drug Evaluation and Research. Tecfidera Chemistry Reviews for Application No. 204063Orig1s000, Dated Mar. 20, 2013.
Center for Drug Evaluation and Research. Tecfidera FDA Approved Labeling Text for Application No. 204063Orig1s000, Dated Mar. 27, 2013.
Center for Drug Evaluation and Research. Tecfidera Medical Review for Application No. 204063Orig1s000, Dated Mar. 17, 2013.
Center for Drug Evaluation and Research. Tecfidera Office Director Memo for Application No. 204063Orig1s000, Dated Mar. 27, 2013.
Center for Drug Evaluation and Research. Tecfidera Officer/ Employee List for Application No. 204063Orig1s000.
Center for Drug Evaluation and Research. Tecfidera Other Reviews for Application No. 204063Orig1s000.
Center for Drug Evaluation and Research. Tecfidera Pharmacology Reviews for Application No. 204063Orig1s000, Dated Feb. 27, 2012.
Center for Drug Evaluation and Research. Tecfidera Proprietary Name Reviews for Application No. 204063Orig1s000, Dated Jan. 16, 2013.
Center for Drug Evaluation and Research. Tecfidera Risk Assessment and Risk Mitigation Review for Application No. 204063Orig1s000, Dated Feb. 6, 2013.
Center for Drug Evaluation and Research. Tecfidera Statistical Reviews for Application No. 204063Orig1s000, Dated Jan. 16, 2013.
Center for Drug Evaluation and Research. Tecfidera Summary Reviews for Application No. 204063Orig1s000, Dated Feb. 27, 2012.
International Search Report and Written Opinion of the ISA for PCT/US14/027401, dated Aug. 26, 2014.
Opposition Against EP2970101; Patentee: Alkermes Pharma Ireland Limited; Generics [UK] Limited; Mar. 6, 2019.
Opposition Against EP2970101; Patentee: Alkermes Pharma Ireland Limited; Hexal AG; Mar. 6, 2019.
Opposition Against EP2970101B; Patentee: Alkermes Pharma Ireland Limited; Opponent: Teva Pharmaceuticals Industries, Ltd., Mar. 5, 2019.
Preliminary Opinion of the EP Opposition Board.
Structure Search Results. HCAPLUS, ACS on STN, Jan. 2013.
TECFIDERA Full Prescribing Information.
U.S. Appl. No. 61/653,375, filed May 30, 2021.
Xenoport's Ceo Hosts Xenoport XP23829 Clinical Trial Results Call (Transcript). Dated Oct. 6, 2012.
Xenoport's Ceo Presents at Citi 2013 Global Healthcare Conference (Transcript), Dated Feb. 27, 2013.
Aakeroy, C. B. et al., "A High-Yielding Supramolecular Reaction", J. Am. Chem. Soc, vol. 124, 2002, 14425-14432.

(56) References Cited

OTHER PUBLICATIONS

Adams, J. D. et al., "Plasma Glutathione and Glutathione Disulfide in the Rat: Regulation and Response to Oxidative Stress", J.Pharmacol. Exper. Ther., vol. 227, 1983, 749-754.
Aguilar, F. et al., "Inositol Hexanicotinate(inositol hexaniacinate) as a Source of Niacin (vitamin B3) Added for Nutritional Purposes in Food Supplements", The EFSA Journal, vol. 949, 2009, 1-20.
Altmeyer, P. et al., "Antipsoriatic Effect of Fumaric Acid Derivatives", J. Am. Acad, Derm., vol. 30, 1994, 977-981.
Bahar, F. G. et al., "Species Difference of Esterase Expression and Hydrolase Activity in Plasma", J. Pharm. Sci.,vol. 101, 2012, 3979-3988.
Balasubramaniyan, V. et al., "Heterocyclisation of Maleic Anhydride Derivatives with Thiourea: Synthesis of 5-substituted-2imino-4-oxo-1,3-thiazolidines", Ind., J., Chem., vol. 29B, 1990, 1092-1096.
Baldi, B. G. et al., "Hydrolysis of Indole-3-Acetic Acid Esters Exposed to Mild Alkaline Conditions", Plant. Physiol, vol. 91, 1989, 9-12.
Bar-Or, A. et al., "Effect of BG-12 (Dimethyl Fumarate) in Subgroups of Patients with Relapsing-Remitting Multiple Sclerosis: An Integrated Analysis of Phase 3 DEFINE and CONFIRM Studies", 65th Annual Meeting of the American Academy of Neurology,: Mar. 16-23, 2013 (San Diego) Poster P07.095.
Barrett, M. et al., "Supersaturation Tracking for the Development, Optimization and Control of Crystallization Processes", Chem. Eng. Res Design, vol. 88, 2010, 1108-1119.
Benyo, Z et al., "GPR109A (PUMA-G/HM74A) Mediates Nicotinic Acid-Induced Flushing", J. Clin. Invest., vol. 115, 2005, 3634-3640.
Benyo, Z. et al., "Nicotinic Acid-Induced Flushing in Mediated by Activation of Epidermal Langerhans Cells", Mol. Pharmacol., vol. 70, 2006, 1844-1849.
Bodor, et al., "Nicotinic Acid: An Old Drug with a Promising Future", Brit. J. Pharmacol. vol. 153, 2008, PPs68-S75.
Bonina, F. et al., "1-ethylazacycloalkan-2-one indomethacin esters as new oral prodrugs: chemical stability, enzymatic hydrolysis, anti-inflammatory activity and gastrointestinal toxicity", Int. J. Pharm, 1997, 245-250.
Breuning, A. et al., Journal of Medicinal Chemistry, vol. 53, No. 5, 2010, 1951-1963.
Brewer, L. et al., "Fumaric Acid Esters in the Management of Severe Psoriasis", Clinical Dermatology, 32, 2007, 246-249.
Bullingham, R. et al., "Clinical Pharmacokinetics of Mycophenolate", Clin. Pharmacokinet., vol. 34, 1998, 429-455.
Bundgaard, H. et al., "Esters of N, N-Disubstituted 2-Hydroxyacetamides as a Novel Highly Biolabile Prodrug Type for Carboxylic Acid Agents", J. Med. Chem., vol. 30, 1987, 451-454.
Bundgaard, H. et al., "Glycolamide Esters as a Novel Biolabile Prodrug Type for Non-Steroidal Anti-Inflammatory Carboxylic Acid Drugs", Int. J. Pharmaceut., vol. 43, 1988, 101-110.
Chmara, H. et al., "Inactivation of glucosamine-6-phosphate synthetase from *Salmonella typhimurium* LT2 by fumaroyl diaminopropanoic acid derivatives, a novel group of glutamine analogs", Biochimica et Biophysica Acta, 870, 1985, 357-366.
Dejong, R. et al., "Selective Stimulation of T Helper 2 Cytokine Responses by the Anti-Psoriasis Agent Monomethyl Fumarate", Eur. J. Immunol., vol. 26, 1996, 2067-2074.
Ellrichmann, G. , "Efficacy of Fumaric Acid Esters in the R6/2 and YAC128 Models of Huntington's Disease", PLoS One, vol. 6, 2011, 1-11.
Engelhardt, A. et al., Naunyn-Schmiedebergs Archiv fuer Experimentelle Pathologie and Pharmakologie, 225, 1955, 541-50.
Eritsian, M. L. et al., "Epoxy Terminated Isocyanuric Acid Derivatives,", Chemical Journal of Armenia, vol. 36, 1983, 116-120.
Evans, D. F. , "Measurement of Gastrointestinal pH Profiles in Normal Ambulant Human Subjects", Gut, vol. 9, 1988, 1035-1041.
Fan, H. et al., "Ester Prodrugs of Ampicillin Tailored for Intracellular Accumulation", Bioorganic & Medicinal Chemistry Letters, vol. 7, No. 24, 1997, 3107-3112.

Fox, R. J. et al., "Clinical Efficacy of BG-12 (Dimethyl Fumurate) in Relapsing-Remitting Multiple Sclerosis (RRMS): An Integrated Analysis of the Phase 3 DEFINE and CONFIRM Studies", 65th Annual Meeting of the American Academy of Neurology,: Mar. 16-23, 2013 (San Diego) Poster P01.162.
Frohman, T. et al., "Symptomatic Therapy in Multiple Sclerosis", Ther. Adv. Neurol. Discord, vol. 4, 2011, 83-98.
Frycak, P. et al., "Evidence of Covalent Interaction of Fumaric Acid Esters with Sulfhydyl Groups in Peptides", J. Mass Spec., vol. 40, 2005, 1309-1318.
Fujiyama, N. , "Involvement of Carboxylesterase 1 and 2 in the Hydrolysis of Mycophenolate", Drug. Met. Dispos, vol. 38, 2010, 2210-2217.
Gadad, A. K. et al., "Synthesis, Spectral Studies and Anti-Inflammatory Activity of Glycolamide Esters of Niflumic Acid as Potential Prodrugs", ArzeimForschDrug Res., vol. 52, 2002, 817-821.
Giovannoni, G. et al., "Relapses Requiring Intravenous Steroid Use and Multiple Sclerosis-Related Hospitalizations: An Integrated Analysis of the BG-12 (Dimethyl Fumurate) Phase 3 Studies", 65th Annual Meeting of the American Academy of Neurology,: Mar. 16-23, 2013 (San Diego) Poster P07.121.
Gogas, K. et al., "Comparison of the Efficacy and Tolerability of a Novel Methylhydrogenfumarate Prodrug with Dimethylfumarate in Rodent Experimental Autoimmune Encephalomyelitis and GI Irritation Models", Congress of European Committee for Treatment and Research in Multiple Sclerosis and 15th Annual Conference of Rehabilitation in MS, Dated Oct. 19, 2010 (Abstract).
Gold, R. et al., "BG-12 (Dimethyl Fumurate) and Pregnancy: Preclinical and Clinical Data from the Clinical Development Program", 65th Annual Meeting of the American Academy of Neurology,: Mar. 16-23, 2013 (San Diego) Poster P02.129.
Gold, R. et al., "Placebo-Controlled Phase 3 Study of Oral BG-12 for Relapsing Multiple Sclerosis", The New England Journal of Medicine, 367(12), 2012, 1098-1107.
Goldstein, J. L. et al., "Clinical Trial: Endoscopic Evaluation of Naproxen Etemesil, A Naproxen Prodrug, vs. Naproxen-A Proof-of-Concept, Randomized, Double-Blind, Active-Comparator Study", Aliment. Pharmacol., Thera, vol. 32, 2010, 1091-1101.
Guarino, V. , "Design and Application of Prodrugs for Drug Delivery", AAPS Webinar, Aug. 23, 2012.
Hanson, et al., "Nicotinic Acid-and Monomethyl Fumarate-Induced Flushing Involves GPR109A Expressed by Keratinocytes and COX-2-Dependent Prostanoid Formation in Mice", J. Clin. Invest, vol. 120, 2010, 2910-2919.
Hanson, J. et al., "Role of HCA2 (GPR109A) in Nicotinic Acid and Fumaric Acid Ester-Induced Effects on the Skin", Pharmacology & Therapeutics 136, 2012, 1-7.
Harthon, L. et al., "Enzymatic Hydrolysis of Pentaerythritoltetranicotinate and Meso-Inositahexanicotinate in Blood and Tissues", Arzneim-Forsch. (Drug Res.), vol. 29, 1979, 1859-1862.
Harthon, L. et al., "On the Absorption, Excretion and Metabolism of Pentaerythritoltetranicotinate", Arzneim-Forsch (Drug Res), vol. 24, 1980, 1688-1692.
Hartmann, M. et al., "Biocide polymers. IV. Synthesis and polymerization of acyl derivatives of N-hydroxymethyl-and N-aminomethylchloroacetamide", Acta Polymerica, 33(3):, 1982, 215-217.
Hartmann, M. et al., "Biozide Polymere II. Synthese Phosphorylierter Phenoxyessigsaureester des Polyvinylalkohols", Acta Polymerica, vol. 31, 1980, 612-613.
Hatanaka, T. et al., "Transport of Amino Acid-Based Prodrugs by the Na+ and Cl-Coupled Amino Acid Transporter ATB0, + and Expression of the Transporter in Tissues Amedable for Drug Delivery", J. Pharmacol., Exper, Ther., vol. 308, 2004, 1138-1147.
Havrdova, E. et al., "BG-12 (Dimethyl Fumurate) Treatment for Relapsing-Remitting Multiple Sclerosis (RRMS) Increases the Proportion of Patients Free of Measured Clinical and Neuroradiologic Disease Activity in the Phase 3 Studies", 65th Annual Meeting ofthe American Academy of Neurology,: Mar. 16-23, 2013 (San Diego) Poster P07.106.

(56) References Cited

OTHER PUBLICATIONS

Head, K. A., "Inositol Hexaniacinate: A Safer Alternative to Niacin", Alternative Med. Rev., vol. 1, 1996, 176-184.
Hoefnagel, J. J. et al., "Long-Term Safety Aspects of Systemic Therapy with Fumaric Acid Esters in Severe Psoriasis", British Journal of Dermatology, 149, 2003, 363-369.
Hosokawa, M., "Structure and Catalytic Properties of Carboxylesterase Isozymes Involved in Metabolic Activation of Prodrugs", Molecules, vol. 13, 2008, 412-431.
Hoxtermann, S. et al., "Fumaric Acid Esters Suppress Peripheral CD4- and CD-8 Positive Lymphocytes in Psoriasis", Dermatology, vol. 196, 1998, 223-230.
Hutchinson, M. et al., "Clinical Efficacy of BG-12 (Dimethyl Fumarate) for Relapsing-Remitting Multiple Sclerosis (RRMS) According to Prior Therapy: An Integrated Analysis of the Phase 3 DEFINE and CONFIRM Studies", 65th Annual Meeting of the American Academy of Neurology,: Mar. 16-23, 2013 (San Diego) Poster P07.128.
Ibay, A. et al., "Synthesis and Properties of Polymers for Biodegradable Implants", ACS Polymeric Materials Science and Engineering, 1985, 505-509.
Jaeger, D. A. et al., "Regioselectivity control in Diels-Alder reactions of surfactar 1,3-dienes with surfactant dienophiles", Journal American Chemical Society, vol. 122, No. 12, 2000, 2749-2757.
Jaeger, D. A. et al., "Regioselectivity of Diels-Adler Reactions of a Surfactant 1,3- Diene with Surfactant Dienophiles", Journal of Organic Chemistry, 58(24):, 1993, 6745-6755.
Jennings, L. et al., "Squamous Cell Carcinoma as a Complication of Fumaric Acid Ester Immunosuppression", JEADV, vol. 23, 2009, 1451.
Jonsson, S. et al., "Synthesis and biological evaluation of new 1,2 Dihydro-4hydroxy-2oxo-3-quinolinecarboxamides for treatement of autoimmun Disoders: Structure-activity relationship", Journal of Medicinal Chemistry, vol. 47(8), 2004, 2075-2088.
Jung, et al., "Intramolecular Diels-Alder chemistry of pyrroles", Journal of the Chemical Society, Chemical Communications, (10),, 1984, 630-632.
Kamanna, V. et al., "The Mechanism and Mitigation of Niacin-Induced Flushing", Int. J. Clin. Prac., vol. 63, 2009, 1369-1377.
Kamimura, V. et al., "Stereoselective Formation of Optically Active 2-oxy-1,3-oxazolidin-4-ones from Chiral O-acylmandelamides or Lactamides", Tetrahedron, vol. 58, 2002, 8763-8770.
Kappos, L. et al., "Efficacy and Safety of Oral Fumarate in Patients with Relapsing-Remitting Multiple Sclerosis: A Multicentre, Randomised, Double-Bind, Placebo-Controlled Phase IIb Study", Lancet, vol. 372, 2008, 1463-1472.
Karaman, R. et al., "Prodrugs of Fumarate Esters for the Treatment of Psoriasis and Multiple Sclerosis-A Computational Approach", J. Mol. Model, vol. 19, 2013, 439-452.
Killestein, J. et al., "Oral Treatment of Multiple Sclerosis", Lancet Neurol., vol. 10, 2011, 1026-1034.
Kita, et al., "Effects of BG-12 (Dimethyl Fumarate) on Quality of Life in Patients with Relapsing-Remitting Multiple Sclerosis (RRMS): An Integrated Analysis of the Phase 3 DEFINE and CONFIRM studies", 65th Annual Meeting of the American Academy of Neurology, 2013 (Poster).
Kita, M. et al., "Clinical and Neuroradiological Efficacy of BG-12 (Dimethyl Fumarate) in US Patients with Relapsing-Remitting Multiple Sclerosis (Rrms): An Integrated Analysis of the Phase 3 DEFINE and CONFIRM Studies", 65th Annual Meeting of the American Academy of Neurology, Mar. 16-23, 2013 (San Diego, CA, USA) Poster P07.1091.
Komadel, P. et al., "Alkaline Hydrolysis of Monomethyl Esters of Maleic and Fumaric Acids", Collection Czechoslovak Chem. Commun., vol. 48, 1983, 1305-1313.
Konzett, V. et al., "The Elimination of Unabsorbed Meso-Inositalhexanicotinate in the Faeces", Arzneim-Forsch, vol. 14, 1964, 1169-1171.
Lehmann, M. et al., "Fumaric Acid Esters are Potent Immunosuppressants: Inhibition of Acute and Chronic Rejection in Rat Kidney Transplantation Models by Methyl Hydrogen Fumarate", Arch Dermatol Res, 294, 2002, 399-404.
Letcher, R. M., "Addition Reactions of Heterocyclic Compounds, Part 79, Reaction of Dimethyl Acetylenedicarboxylate with some cyclohept[b]indoles and cyclo-oct[b]indoles", J. Chem. Soc., Perkin Trans., 1983, 515-525.
Li, B. et al., "Butyrylcholinesterase, Paraoxonase, and Albumin Esterase, but not carboxylesterase, are Present in Human Plasma", Biochem. Pharmacol., vol. 70, 2005, 1673-1684.
Liang, D. et al., "Determination of Inositol Hexanicotinate in Rate Plasma by High Performance Liquid Chromatography with UV Detection", J. Chromat., B., vol. 863, 2008, 172-176.
Lim, R. K. et al., "Azirine Ligation: Fast and Selective Protein Conjugation via Photoinduced Azirine-Alkene Cycloaddition", Chemical Communications 46(42), 2010, 7993-7995.
Lim, S. et al., "TNF-alpha: A Paradigm of Paradox and Complexity in Multiple Sclerosis and Its Animal Models", Open Autoimmun. J., vol. 2, 2010, 160-170.
Linker, R. et al., "Fumaric Acid Esters Exert Neuroprotective Effects in Neuroinflammation Via Activation of the Nrf2 Antioxidant Pathway", Brain, vol. 134, 2011, 678-392.
Lissin, D. et al., "Favorable Metabolism and Pharmacokinetics of Formulations of XP23929, a Novel Fumaric Acid Ester, in Healthy Subjects", 65th Annual Meeting of the American Academy of Neurology,: Mar. 16-23, 2013 (San Diego) Poster P05.189.
Litjens, N. et al., "In vitro Pharmacokinetics of Anti-Psoriatic Fumaric Acid Esters", BMC Pharmacol, vol. 4, 2004, 1-7.
Litjens, N. et al., "Pharmacokinetics of Oral Fumarates in Healthy Subjects", Brit. J. Clin. Pharamcol., vol. 58, 2004.
"Prodrugs: Challenges and Rewards Part 1", Prodrugs of Carboxylic Acids, Springer, 2007, 3-11.
Mahfouz, N. M., "Cyclic amide derivatives as potential prodrugs II: N-hydroxymethylsuccinimide-/isatin esters of some NSAIDs as prodrugs with an improved therapeutic index", Eur. J. Med Chem, 34, 1999, 551-562.
McCullough, T. et al., "Compartive Gastric Irritation of the Fumaric Acid Esters Dimethyl Fumarate (DMF) and XP23829 in Rat and Monkey", American Academy of Neurology (AAN) Conference Mar. 2013 (Abstract).
Meltzer, L. et al., "Gastrointestinal Tolerability Events in Relapsing-Remitting Multiple Sclerosis Patients Treated with BG-12 (Dimethyl Fumarate) in DEFINE and CONFIRM", 65th Annual Meeting of the American Academy of Neurology,: Mar. 16-23, 2013 (San Diego) Poster P01.164.
Meyers, et al., "Varying Cost and Free Nicotinic Acid Content in Over-The-Counter Niacin Preparations for Dyslipidemia", Annals Intern. Med., vol. 139, 2003, 996-1003.
Michelet, F. et al., "Blood and Plasma Glutathione Measured in Healthy Subjects by HPLC: Relation to Sex, Aging, Biological Variables, and Life Habits", Gen. Clin. Chem. vol. 41, 1995, 1509-1517.
Moharregh-Khiabani, D. et al., "Fumaric Acid and its Esters: An Emerging Treatment for Multiple Sclerosis", Current Neuropharmacology, 7, 2009, 60-64.
Mroweitz, et al., "Treatment of Severe Psoriasis with Fumaric Acid Esters: Scientific Background and Guidelines for Therapeutic Use", British Journal of Dermatology, vol. 141, 1999, 424-429.
Mrowietz, U. et al., "Treatment of Psoriasis with Fumaric Acid Esters: Results of a Prospective Multicentre Study", Brit. J. Dermatol., vol. 138, 1998, 456-460.
Nelson, K. C. et al., "Effect of Dietary Inducer Dimethylfumarate on Glutathione in Cultured Human Retinal Pigment Epithelial Cells", IVOS, vol. 40, 1999, 1927-1935.
Nicholas, R. et al., "Development of Oral Immunomodulatory Agents in the Management of Multiple Sclerosis", Drug Des. Dev. Ther., vol. 5, 2011, 255-274.
Nieboer, C. et al., "Fumaric Acid Therapy in Psoriasis: A Double-Blind Comparison Between Fumaric Acid Compound Therapy and Monotherapy with Dimethylfumaric Acid Ester", Dermatologica, vol. 181, 1990, 33-37.
Nieboer, C. et al., "Systematic Therapy with Fumaric Acid Derivatives: New Possibilities in the Treatment of Psoriasis", J. Am. Acad. Dermatol., vol. 20, 1989, 601-608.

(56) References Cited

OTHER PUBLICATIONS

Nielsen, N. M. et al., "Glycolamide Esters as Biolabile Prodrugs of Carboxylic Acid Agents: Synthesis, Stability, Bioconversion, and Physicochemical Properties", J. of Pharmaceutical Sciences, 77(4), or vol. 74 (285-297)1988, 285-298.
Norris, R. B., "Flush-Free Niacin," Dietary Supplement May be Benefit-Free, Preventative Cardiology, 2006, 64-65.
Papadopoulou, A. et al., "Dimethyl Fumarate for Multiple Sclerosis", Expert Opin. Investig. Drug, vol. 19, 2010, 1603-1612.
Paulvannan, K., "An Atom-Economical Approach to Conformationally Constrained Tricyclic Nitrogen Heterocycles via Sequential and Tandem Ugi/Intramolecular Diels-Adler Reaction of Pyrrole", J. Org. Chem., vol. 69, 2004, 1207-1214.
Paulvannan, K. et al., "Preparation of Tricyclic Nitrogen Heterocycles via Intramolecular Diels-Adler Reaction of Furans", Tetrahedron, vol. 55, 1999, 7433-7440.
Phillips, L. et al., "Safety and Tolerability of Oral BG-12 (Dimethyl Fumarate) in Relapsing-Remitting Multiple Sclerosis (RRMS): Interim Results from ENDORSE Extension Study", 65th Annual Meeting of the American Academy of Neurology,: Mar. 16-23, 2013 (San Diego) Poster P01.162.
Poon, I. O. et al., "Dissolution Profiles of Nonprescription Extended Release Niacin and Inositol Niacinate Products", Am. H. Health-Syst. Pharm., 2006, 2128-2134.
Rautio, J. et al., Nat. Rev. Drug Disc., vol. 7, 2008, 255-270.
Reich, K. et al., "Efficacy and Safety of Fumaric Acid Esters in the Long-Term Treatment of Psoriasis =A Retrospective Study (FUTURE)", JDDG, vol. 7, 2009, 603-610.
Rhodes, K. et al., "BG-12 and Neuroprotection in MS", Biogen IDEC (Presentation).
Roll, A. et al., "Use of Fumaric Acid Esters in Psoriasis", Indian J. Dermatol.,Venerol., Leprol., vol. 73, 2007, 133-137.
Rostami-Yazdi, M. et al., "Detection of Metabolites of Fumaric Acid Esters in Human Urine: Implications for Their Mode of Action", J. Investigative Dermatol., vol. 129, 2010, 231-234.
Rostami-Yazdi, M. et al., "Pharmacokinetics of Anti-Psoriatic Fumaric Acid Esters in Psoriasis Patients", Arch. Dermatol, Res., vol. 302, 2010, 531-538.
Saari, et al., "Synthesis and Antihypertensive Activity of Some Ester Progenitors of Methyldopa", Journal of Medicinal Chemistry 21(8), 1978, 746-753.
Sadeh, T. et al., "The Photodimerization of Monomethyl Fumarate", J. Am. Chem. Soc, 1962, 3970.
Salvi, A. et al., "Esterase-Like Activity of Human Serum Albumin Toward Prodrug Esters of Nicotinic Acid", Drug Met. Dispos., vol. 25, 1997, 395-398.
Scannevin, R. et al., "BG-12 (Dimethyl Fumarate) in Neuroprotective in the Murine Cuprizone/Rapamycin Model of Demyeliniation and Neurodegeneration", 65th Annual Meeting of the American Academy of Neurology,: Mar. 16-23, 2013 (San Diego) Poster P05.184.
Schilling, S. et al., "Fumaric Acid Esters are Effective in Chronic Experimental Autoimmune Encephalomyelitis and Suppress Macrophage Infiltration", Clinical and Experimental Immunology, 145, 2006, 101-107.
Schimrigk, S. et al., "Oral Fumaric Acid Esters for the Treatment of Active Multiple Sclerosis: an Open-Label, Baseline-Controlled Pilot Study", European Journal of Neurology, 13, 2006, 604-610.
Schmidt, T. et al., "Reacivity of Dimethyl Fumarate and Methylhydrogen Fumarate Towards Glutathione and N-Acetyl-L-Cysteine-Preparation of S-Substituted Thiosuccinic Acid Esters", Biorg. Med. Chem., vol. 15, 2007, 333-342.
Sebok, B. et al., "Antiprolifertive and Cytotoxic Profiles of Antipsoriatic Fumaric Acid Derivatives in Keratinocyte Cultures", Eur. J. Pharmaco. Sec., vol. 270, 1994, 79-87.
Serajuddin, A., "Salt Formation to Improve Drug Solubility", Adv. Drug. Deliv. Rev., vol. 59, 2007, 603-616.
Shackett, M. et al., "BG-12 (Dimethyl Fumarate) Pharmacodynamic Responses Have Distinct Temporal Profiles and are Dose-Dependent", 65th Annual Meeting of the American Academy of Neurology,: Mar. 16-23, 2013 (San Diego) Poster P05.146.
Sigroth, K., "Pentaerythritolteranicotinate (Perycit) in the Treatment of Hypercholesteraemia", Acta. Med. Scand., vol. 184, 1968, 269-273.
Sobieraj, D. M. et al., "Dimethyl Fumarate: A Fumaric Acid Ester Under Investigation for the Treatment of Relapsing-Remitting Multiple Sclerosis", Formulatory, J., vol. 47, 2012, 386-391.
Sommer, V. H., "Nicotinic Acid Levels in the Blood and Fibrinolysis Under the Influence of Hexanicotinic Acid Ester of m-inositol", Arzneimitteforschung, vol. 15, 1965, 1337-1339.
Spatz, S. et al., "Methyl Hydrogen Fumarate", J. Org. Chem., vol. 23, 1958, 1559-1560.
Spencer, S. R. et al., "Induction of Glutathione Transferases and NAD(P)H: Quinone Reductase by Fumaric Acid Derivatives in Rodent Cells and Tissues", Cancer Res., vol. 50, 1990, 7871-7875.
Svedmyr, N., "Comparison Between Absorption of Nicotinic Acid and Pentaerythritol Tetranicotinate (Perycit) Form Ordinary and Enterocoated Tablets", Acta Pharmacol, Et., Toxicol., vol. 28, 1970, 66-74.
Tam, S. et al., "Multiple Sclerosis, A Paradigm Change with Oral Agents?", Formulary, vol. 46, 2011, 228-240.
Testa, B. et al., "Hydrolysis in Drug and Prodrug Metabolism", Chemistry, Biochemistry And Enzymology, John Wiley and Sons, Ltd., 2002.
Thio, H. B. et al., "Fumaric Acid Derivatives Evoke a Transient Increase in Intracellular Free Calcium Concentration and Inhibit the Proliferation of Human Keratinocytes II", Brit. J. Dermatol., vol. 1361, 1994, 856-861.
Tsujikawa, K. et al., "In Vitro Stability and Metabolism of Salvinorin A in Rat Plasma", Xenobiotica, vol. 39, 2009, 391-398.
Wain, E. M. et al., "Treatment of Severe, Recalcitrant, Chronic Plaque Psoriasis with Fumaric Acid Esters: A Prospective Study", Brit. J. Dermatol., vol. 162, 2010, 427-434.
Wang, J. et al., "A Biosynthetic Route to Photoclick Chemistry on Proteins", Journal of the American Chemical Society, 132(42), 2010, 14812-14818.
Wang, Y. et al., "Synthesis of Spin-Labelled Anticancer Derivatives of 5-Fluorouracil", Chemical J. Chinese Univ., vol. 13, 1992, 1561-1563.
Wantanabe, K., "The Toxicological Assessment of Cyclopentyl Methyl Ether (CPME) as a Green Solvent", Molecules, vol. 18, 2013, 3183-3194.
Welsh, A. L. et al., "Inositol Hexanicotinate for Improved Nicotinic Acid Therapy", Int. Rec. Med., vol. 174, 1961, 9-15.
Wendelin, et al., "1-Chlormethylisatin-ein neues Reagens zur Identiizierung yon Carbonsauren", Monatshefte Fur Chemie, 103, Jan. 14, 1972, 1632-1642.
Werdenberg, D. et al., "Presystematic Metabolism and Intestinal Absorption of Antipsoriatic Fumaric Acid Esters", Biopharm. Drug Dispos., vol. 24, 2003, 259-273.
Werdenberg, D., "Stability, Permeability and Pharmacokinetics of Perorally Administrated Fumarates", Swiss Federal Institute of Technology Zurich (Dissertation), 2003.
Wollina, U. et al., "Fumaric Acid Esters in Dermatology", Ind. Dermatol. Online, J., vol. 2, 2011, 111-119.
Wustrow, D. et al., "Comparison of the Efficacy and Tolerability of a Novel Methyl Hydrogenfumarate Prodrug with Dimethyl Fumarate in Rodent EAE and GI Irritation", Neurology, Bol. 76, Abstract, 2011.
Wustrow, D. et al., "Comparison of XP23829 with DMF, the Active Ingredient of BG-12", Poster SC03.
Yamada, M. et al., "Synthesis and Polymerization of Unsaturated Dibasic Acid Derivatives. IV.", Journal of synthetic organic chemistry, Japan, vol. 23, No. 2, 1965, 166-170.
Yazdi, M. R. et al., "Fumaric Acid Esters", Clinics In Dermatology, 26, 2008, 522-526.
Zhu, K. et al., "Inhibition of Dendritic Cell Differentation by Fumaric Acid Esters", J. Investigative Dermatol., Vo. 116, 2001, 203-208.
Ziliotto, G. et al., "Comparitive Studies of the Response of Normolipemic and Dyslipemic Aged Subjects to 2 Forms of Delayed-Action Nicotinic Acid Polyesters, Pentaerythrotol Tetranicotinate

(56) References Cited

OTHER PUBLICATIONS and Inositol Hexanicotinate, Results of a Controlled Cross-Over Trial", Arch. Sc. Med., vol. 134, 1977, 359-394.

Figure 1 Hydrolysis of Compound 16 at pH 7.9, 25° C, showing vinylic region, initial time points.

Figure 2 Hydrolysis of Compound 16 at pH 7.9, 25° C, showing vinylic region, later time points.

Figure 3 Hydrolysis of Compound 16 at pH 7.9, 25° C, showing aliphatic region, later time points.

Figure 4 Hydrolysis of Reference Compound A at pH 7.9, 37° C, showing vinylic region.

Figure 5 Hydrolysis of Reference Compound A at pH 7.9, 37° C, showing aliphatic region (water peak at 4.8 ppm removed for clarity).

PRODRUGS OF FUMARATES AND THEIR USE IN TREATING VARIOUS DISEASES

RELATED APPLICATIONS

This application is a continuation of U.S. application Ser. No. 16/524,498, filed Jul. 29, 2019, which is a continuation of U.S. application Ser. No. 16/145,703, filed Sep. 28, 2018, now U.S. Pat. No. 10,406,133, issued Sep. 10, 2019, which is a continuation of U.S. application Ser. No. 15/704,219, filed Sep. 14, 2017, now U.S. Pat. No. 10,117,846, issued Nov. 6, 2018, which is a continuation of U.S. application Ser. No. 15/295,370, filed Oct. 17, 2016, now U.S. Pat. No. 9,775,823, issued Oct. 3, 2017, which is a continuation of U.S. application Ser. No. 14/212,745, filed Mar. 14, 2014, now U.S. Pat. No. 9,505,776, issued Nov. 29, 2016, which claims the benefit of U.S. Provisional Application No. 61/934,365, filed Jan. 31, 2014 and U.S. Provisional Application No. 61/782,445, filed Mar. 14, 2013, the contents of which are incorporated herein by reference in their entireties.

FIELD OF THE INVENTION

The present invention relates to various prodrugs of monomethyl fumarate. In particular, the present invention relates to derivatives of monomethyl fumarate which offer improved properties relative to dimethyl fumarate. The invention also relates to methods of treating various diseases.

BACKGROUND OF THE INVENTION

Fumaric acid esters (FAEs) are approved in Germany for the treatment of psoriasis, are being evaluated in the United States for the treatment of psoriasis and multiple sclerosis, and have been proposed for use in treating a wide range of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, *Trends Mol Med* 2005, 111(1), 43-48; and Yazdi and Mrowietz, *Clinics Dermatology* 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. Nos. 6,509,376, 6,858,750, and 7,157,423); transplantation (Joshi and Strebel, WO 2002/055063, US 2006/0205659, U.S. Pat. Nos. 6,359,003, 6,509,376, and 7,157,423; and Lehmann et al., *Arch Dermatol Res* 2002, 294, 399-404); autoimmune diseases (Joshi and Strebel, WO 2002/055063, U.S. Pat. Nos. 6,509,376, 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., *Eur J Neurology* 2006, 13, 604-610; and Schilling et al., *Clin Experimental Immunology* 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

FUMADERM®, an enteric coated tablet containing a salt mixture of monoethyl fumarate and dimethyl fumarate (DMF) which is rapidly hydrolyzed to monomethyl fumarate, regarded as the main bioactive metabolite, was approved in Germany in 1994 for the treatment of psoriasis. FUMADERM® is dosed TID with 1-2 grams/day administered for the treatment of psoriasis. FUMADERM® exhibits a high degree of interpatient variability with respect to drug absorption and food strongly reduces bioavailability. Absorption is thought to occur in the small intestine with peak levels achieved 5-6 hours after oral administration. Significant side effects occur in 70-90% of patients (Brewer and Rogers, *Clin Expt'l Dermatology* 2007, 32, 246-49; and Hoefnagel et al., *Br J Dermatology* 2003, 149, 363-369). Side effects of current FAE therapy include gastrointestinal upset including nausea, vomiting, diarrhea and/or transient flushing of the skin.

Multiple sclerosis (MS) is an autoimmune disease with the autoimmune activity directed against central nervous system (CNS) antigens. The disease is characterized by inflammation in parts of the CNS, leading to the loss of the myelin sheathing around neuronal axons (gradual demyelination), axonal loss, and the eventual death of neurons, oligodendrocytes and glial cells.

Dimethyl fumarate (DMF) is the active component of the experimental therapeutic, BG-12, studied for the treatment of relapsing-remitting MS (RRMS). In a Phase IIb RRMS study, BG-12 significantly reduced gadolinium-enhancing brain lesions. In preclinical studies, DMF administration has been shown to inhibit CNS inflammation in murine and rat EAE. It has also been found that DMF can inhibit astrogliosis and microglial activations associated with EAE. See, e.g., US Published Application No. 2012/0165404.

There are four major clinical types of MS: 1) relapsing-remitting MS (RRMS), characterized by clearly defined relapses with full recovery or with sequelae and residual deficit upon recovery; periods between disease relapses characterized by a lack of disease progression; 2) secondary progressive MS (SPMS), characterized by initial relapsing remitting course followed by progression with or without occasional relapses, minor remissions, and plateaus; 3) primary progressive MS (PPMS), characterized by disease progression from onset with occasional plateaus and temporary minor improvements allowed; and 4) progressive relapsing MS (PRMS), characterized by progressive disease onset, with clear acute relapses, with or without full recovery; periods between relapses characterized by continuing progression.

Clinically, the illness most often presents as a relapsing-remitting disease and, to a lesser extent, as steady progression of neurological disability. Relapsing-remitting MS (RRMS) presents in the form of recurrent attacks of focal or multifocal neurologic dysfunction. Attacks may occur, remit, and recur, seemingly randomly over many years. Remission is often incomplete and as one attack follows another, a stepwise downward progression ensues with increasing permanent neurological deficit. The usual course of RRMS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes. Periods between relapses during the relapsing-remitting phase are clinically stable. On the other hand, patients with progressive MS exhibit a steady increase in deficits, as defined above and either from onset or after a period of episodes, but this designation does not preclude the further occurrence of new relapses.

Notwithstanding the above, dimethyl fumarate is also associated with significant drawbacks.

For example, dimethyl fumarate is known to cause side effects upon oral administration, such as flushing and gastrointestinal events including, nausea, diarrhea, and/or upper abdominal pain in subjects. See, e.g., Gold et al., *N. Eng. J. Med.*, 2012, 367(12), 1098-1107. Dimethyl fumarate is dosed BID or TID with a total daily dose of about 480 mg to about 1 gram or more. Further, in the use of a drug for long-term therapy it is desirable that the drug be formulated so that it is suitable for once- or twice-daily administration to aid patient compliance. A dosing frequency of once-daily or less is even more desirable.

Another problem with long-term therapy is the requirement of determining an optimum dose which can be tolerated by the patient. If such a dose is not determined this can lead to a diminution in the effectiveness of the drug being administered.

Accordingly, it is an object of the present invention to provide compounds and/or compositions which are suitable for long-term administration.

It is a further object of the present invention to provide the use of a pharmaceutical active agent in a manner which enables one to achieve a tolerable steady state level for the drug in a subject being treated therewith.

Because of the disadvantages of dimethyl fumarate described above, there continues to be a need to decrease the dosing frequency, reduce side-effects and/or improve the physicochemical properties associated with DMF. There remains, therefore, a real need in the treatment of neurological diseases, such as MS, for a product which retains the pharmacological advantages of DMF but overcomes its flaws in formulation and/or adverse effects upon administration. The present invention addresses these needs.

SUMMARY OF THE INVENTION

Figure 1:
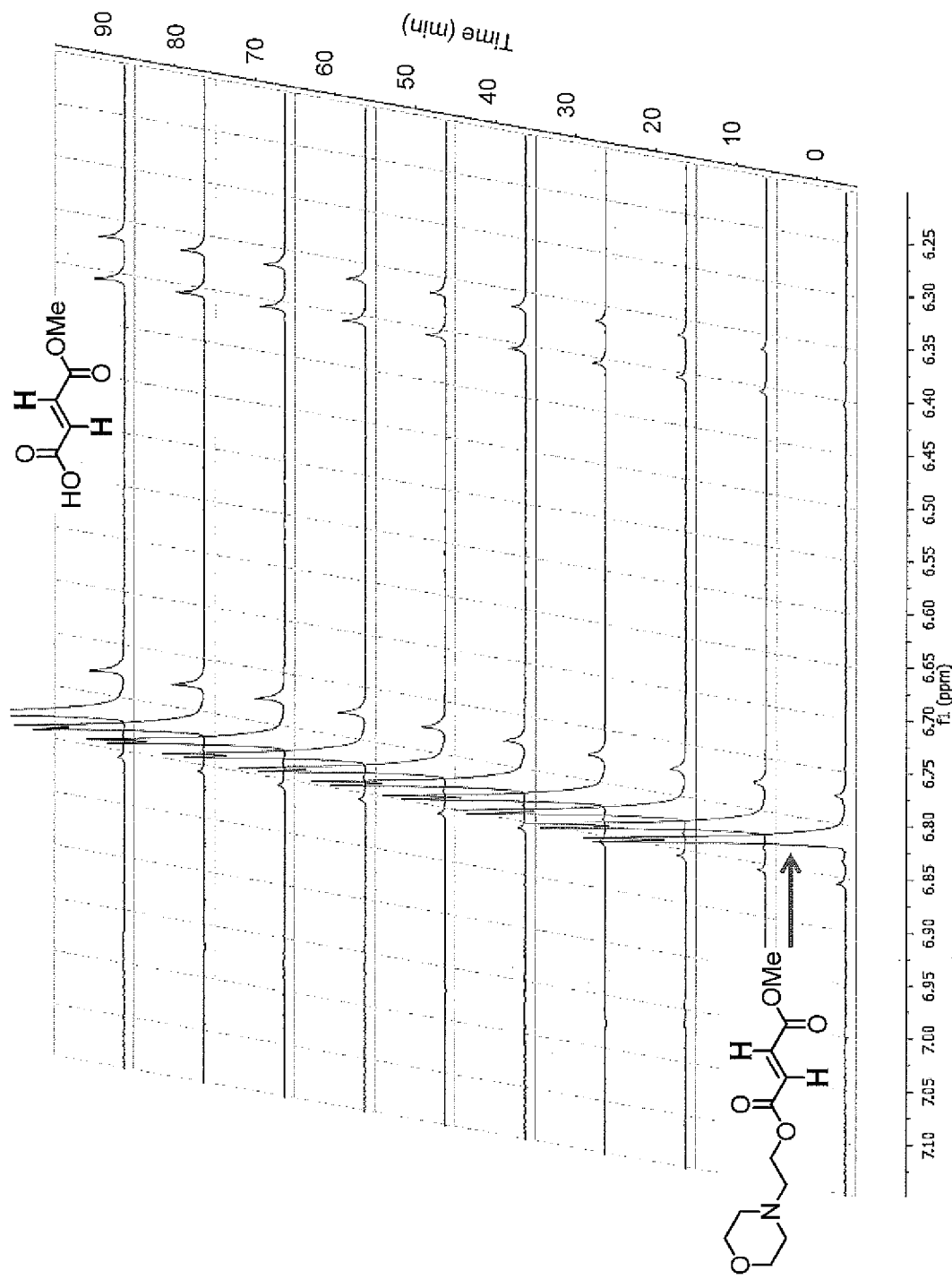
FIG. 1 depicts the hydrolysis of Compound 16 at pH 7.9, 25° C., showing vinylic region, as observed by NMR over 90 minutes.
Figure 2:
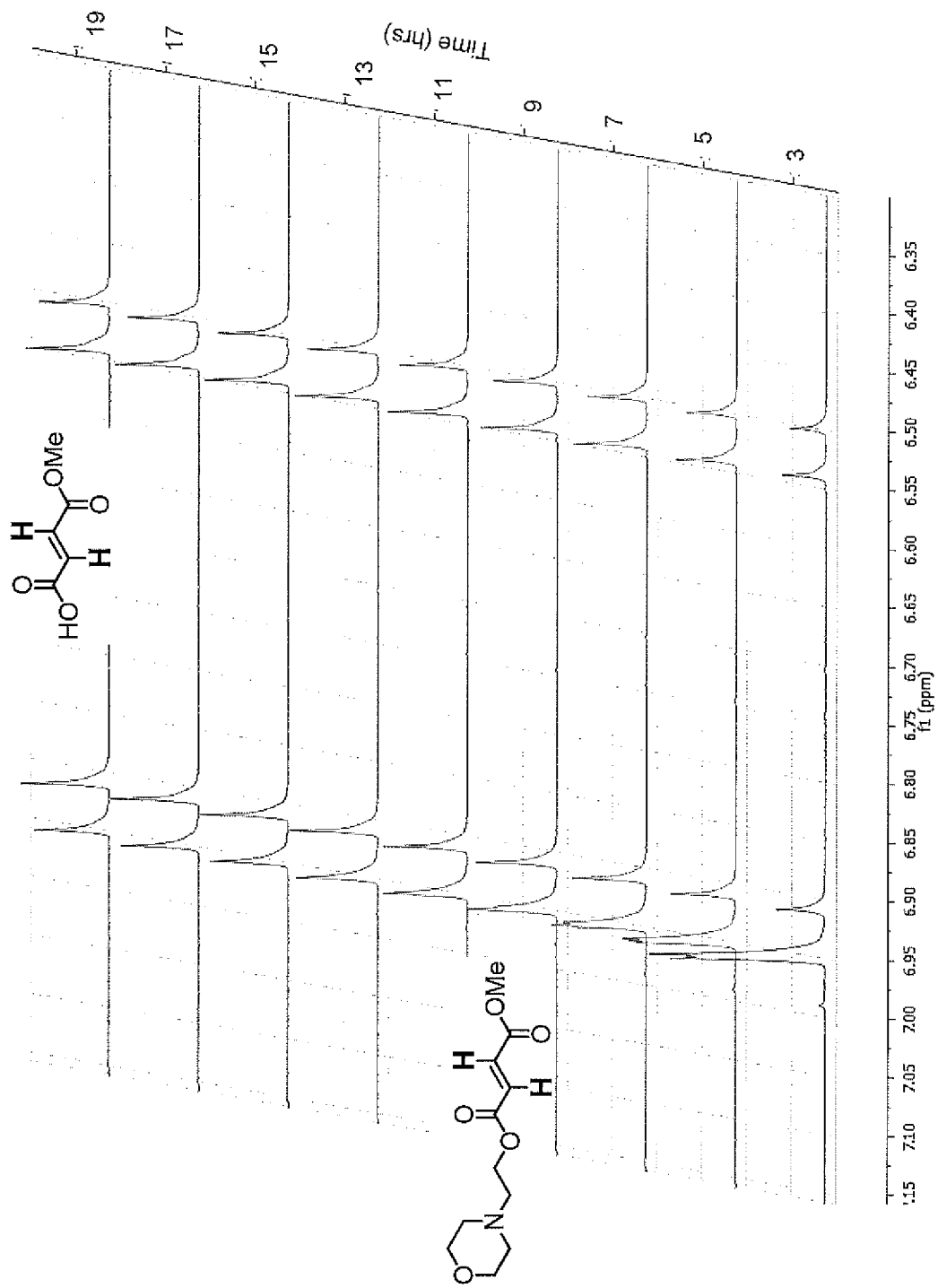
FIG. 2 depicts the hydrolysis of Compound 16 at pH 7.9, 25° C., showing vinylic region, as observed by NMR over 19 hours.
Figure 3:
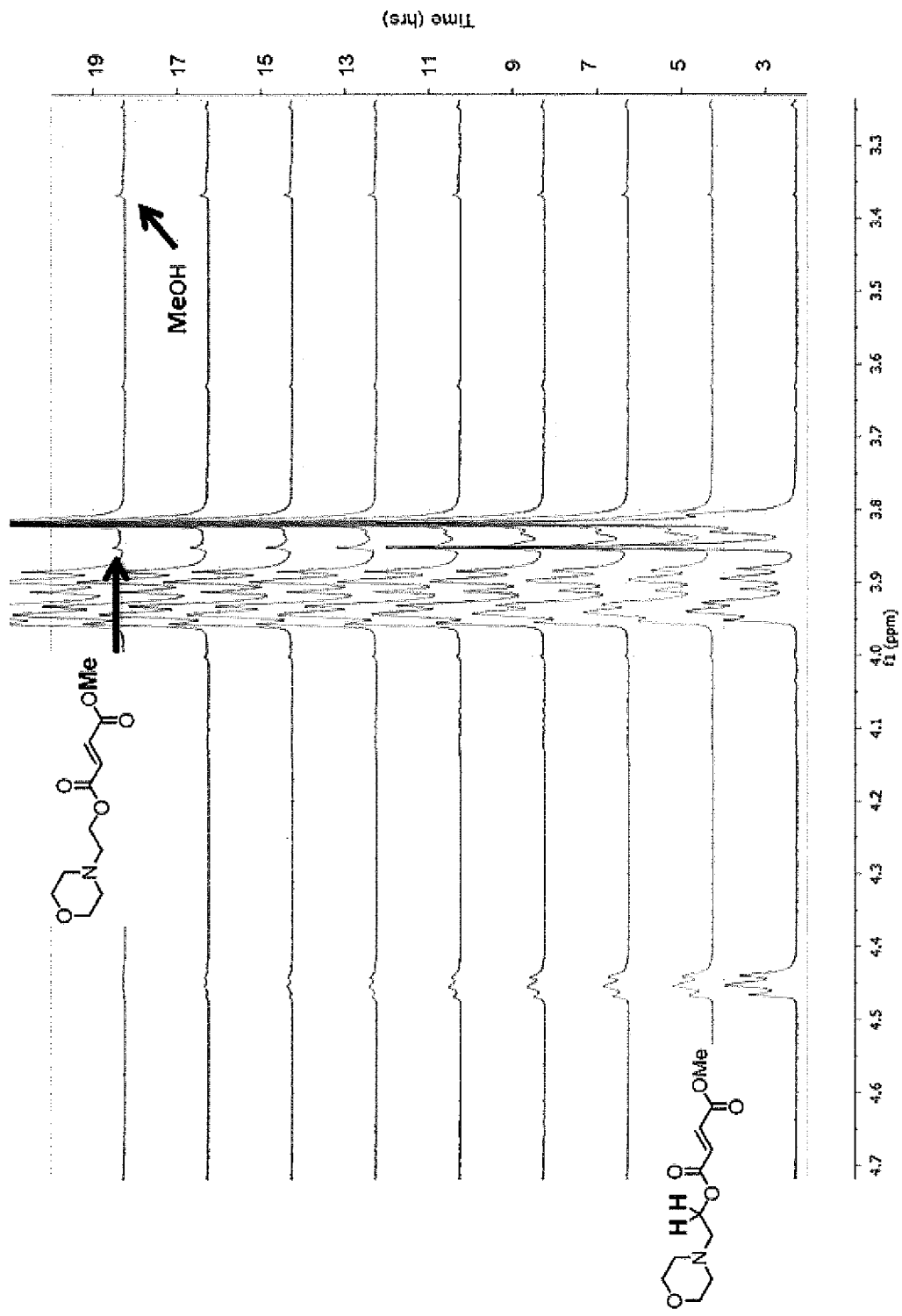
FIG. 3 depicts the hydrolysis of Compound 16 at pH 7.9, 25° C., showing aliphatic region, as observed by NMR over 19 hours.
Figure 4:
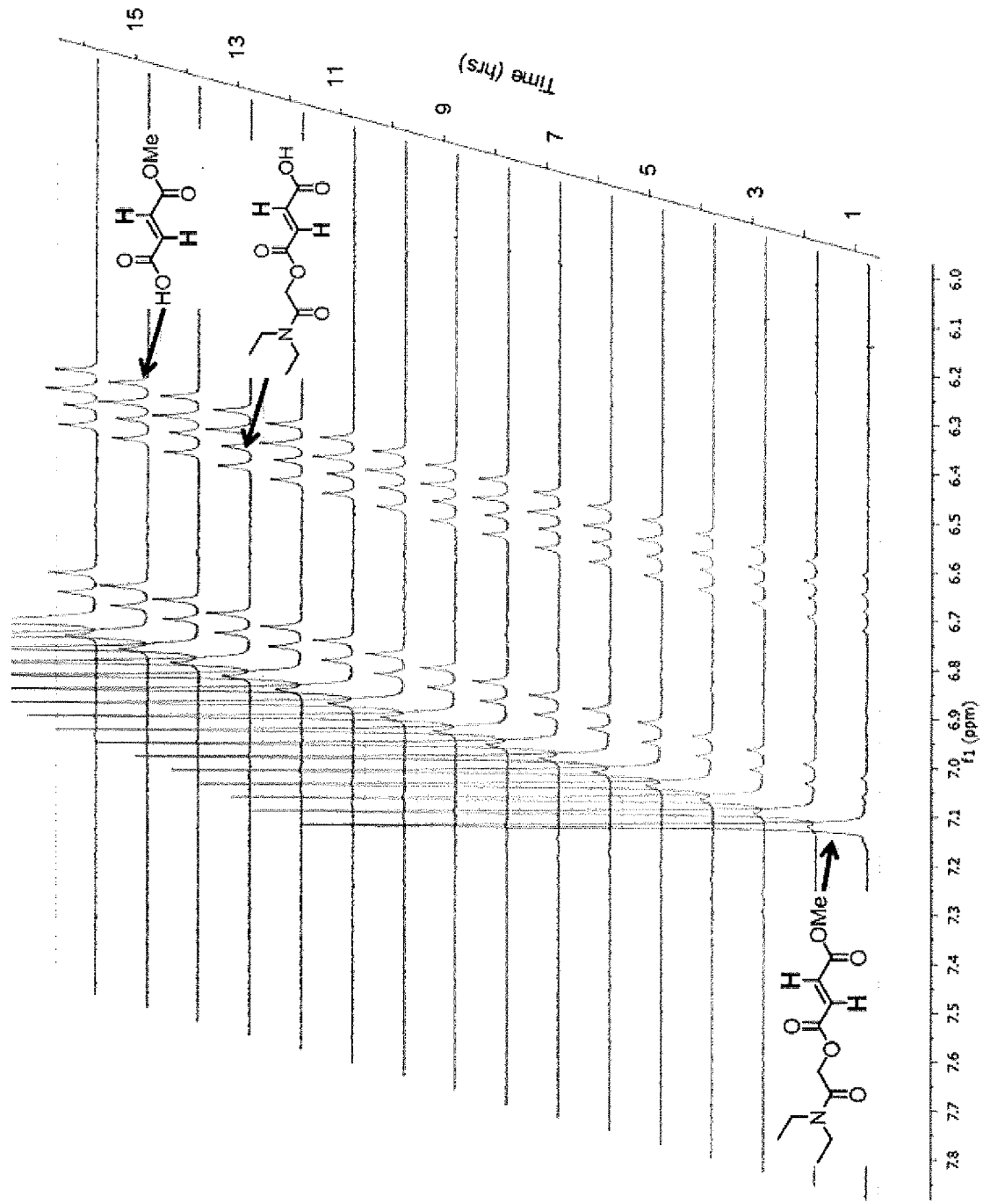
FIG. 4 depicts the hydrolysis of Reference Compound A at pH 7.9, 37° C., showing vinylic region, as observed by NMR over 15 hours.
Figure 5:
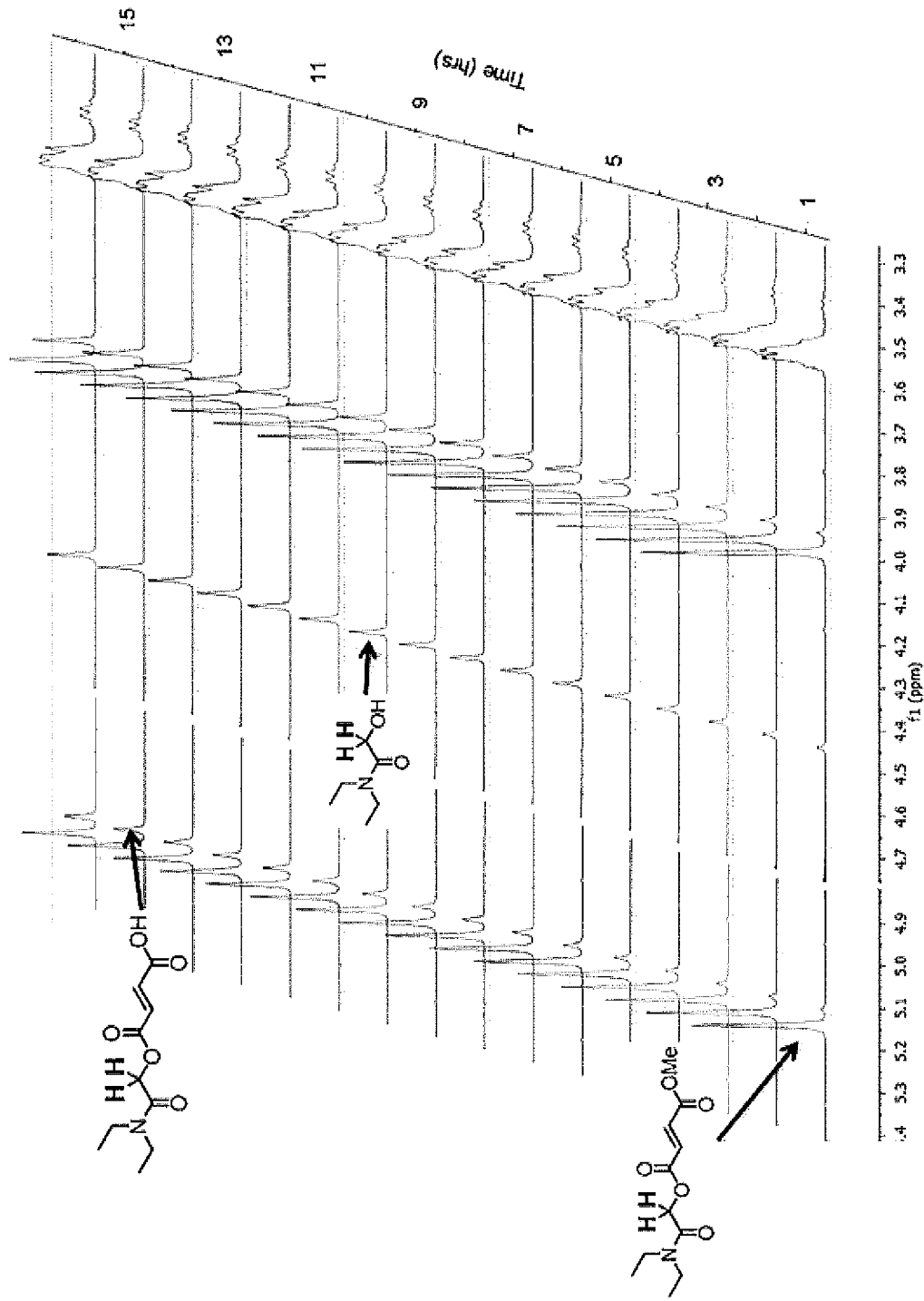
FIG. 5 depicts the hydrolysis of Reference Compound A at pH 7.9, 37° C., showing aliphatic region, as observed by NMR over 15 hours.

This invention is directed to the surprising and unexpected discovery of novel prodrugs and related methods useful in the treatment of neurological diseases. The methods and compositions described herein comprise one or more prodrugs (e.g., aminoalkyl prodrugs) of monomethyl fumarate (MMF). The methods and compositions provide for a therapeutically effective amount of an active moiety in a subject for a time period of at least about 8 hours to at least about 24 hours.

More specifically, the compounds of the invention can be converted in vivo, upon oral administration, to monomethyl fumarate. Upon conversion, the active moiety (i.e., monomethyl fumarate) is effective in treating subjects suffering from a neurological disease.

The present invention provides, in part, a compound of Formula (I), or a pharmaceutically acceptable salt, polymorph, hydrate, solvate or co-crystal thereof:

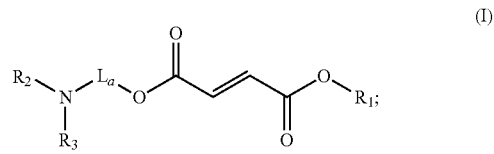

wherein:

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S; and $R_2$ and $R_3$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

or alternatively, $R_2$ and $R_3$, together with the nitrogen atom to which they are attached, form a substituted or unsubstituted heteroaryl comprising one or two 5- or 6-member rings and 1-4 heteroatoms selected from N, O and S or a substituted or unsubstituted heterocycle comprising one or two 5- or 6-member rings and 1-4 heteroatoms selected from N, O and S. The present invention also provides pharmaceutical compositions comprising one or more compounds of any of the formulae described herein and one or more pharmaceutically acceptable carriers.

The present invention also provides methods of treating a neurological disease by administering to a subject in need thereof, a therapeutically effective amount of a compound of any of the formulae described herein, or a pharmaceutically acceptable salt, polymorph, hydrate, solvate or co-crystal thereof, such that the disease is treated.

The present invention also provides methods of treating multiple sclerosis by administering to a subject in need thereof, a therapeutically effective amount of a compound of any of the formulae described herein, or a pharmaceutically acceptable salt, polymorph, hydrate, solvate or co-crystal thereof, such that the multiple sclerosis is treated.

The present invention also provides methods of treating relapsing-remitting multiple sclerosis (RRMS) by administering to a subject in need thereof, a therapeutically effective amount of a compound of any of the formulae described herein, or a pharmaceutically acceptable salt, polymorph, hydrate, solvate or co-crystal thereof, such that the multiple sclerosis is treated. The present invention also provides methods of treating secondary progressive multiple sclerosis (SPMS) by administering to a subject in need thereof, a therapeutically effective amount of a compound of any of the formulae described herein, or a pharmaceutically acceptable salt, polymorph, hydrate, solvate or co-crystal thereof, such that the multiple sclerosis is treated.

The present invention also provides methods of treating primary progressive multiple sclerosis (PPMS) by administering to a subject in need thereof, a therapeutically effective amount of a compound of any of the formulae described herein, or a pharmaceutically acceptable salt, polymorph, hydrate, solvate or co-crystal thereof, such that the multiple sclerosis is treated. The present invention also provides methods of treating progressive relapsing multiple sclerosis (PRMS) by administering to a subject in need thereof, a therapeutically effective amount of a compound of any of the formulae described herein, or a pharmaceutically acceptable salt, polymorph, hydrate, solvate or co-crystal thereof, such that the multiple sclerosis is treated.

The present invention also provides methods of treating Alzheimer's disease by administering to a subject in need thereof, a therapeutically effective amount of a compound of any of the formulae described herein, or a pharmaceutically acceptable salt, polymorph, hydrate, solvate or co-crystal thereof, such that the Alzheimer's disease is treated.

The present invention also provides methods of treating cerebral palsy by administering to a subject in need thereof, a therapeutically effective amount of a compound of any of the formulae described herein, or a pharmaceutically acceptable salt, polymorph, hydrate, solvate or co-crystal thereof, such that the cerebral palsy is treated.

The present invention also provides compounds and compositions that enable improved oral, controlled- or sustained-release formulations. Specifically, dimethyl fumarate is administered twice or three times daily for the treatment of relapsing-remitting multiple sclerosis. In contrast, the compounds and compositions of the present invention may enable formulations with a modified duration of therapeutic efficacy for reducing relapse rates in subjects with multiple sclerosis. For example, the present compounds and compositions provide therapeutically effective amounts of monomethyl fumarate in subjects for at least about 8 hours, at least about 12 hours, at least about 16 hours, at least about 20 hours or at least about 24 hours.

The present invention also provides compounds, compositions and methods which may result in decreased side effects upon administration to a subject relative to dimethyl fumarate. For example, gastric irritation and flushing are known side effects of oral administration of dimethyl fumarate in some subjects. The compounds, compositions and methods of the present invention can be utilized in subjects that have experienced or are at risk of developing such side effects.

The present invention also provides for compounds and compositions which exhibit improved physical stability relative to dimethyl fumarate. Specifically, dimethyl fumarate is known in the art to undergo sublimation at ambient and elevated temperature conditions. The compounds of the invention possess greater physical stability than dimethyl fumarate under controlled conditions of temperature and relative humidity. Specifically, in one embodiment, the compounds of the formulae described herein exhibit decreased sublimation relative to dimethyl fumarate.

Further, dimethyl fumarate is also known to be a contact irritant. See e.g., Material Safety Data Sheet for DMF. In one embodiment, the compounds of the present invention exhibit reduced contact irritation relative to dimethyl fumarate. For example, the compounds of the formulae described herein exhibit reduced contact irritation relative to dimethyl fumarate.

The present invention also provides for compounds and compositions which exhibit decreased food effect relative to dimethyl fumarate. The bioavailability of dimethyl fumarate is known in the art to be reduced when administered with food. Specifically, in one embodiment, the compounds of the formulae described herein exhibit decreased food effect relative to dimethyl fumarate.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

The present invention provides novel compounds and methods of treating a neurological disease by administering a compound of Formula (I), (Ia), (Ib), (II), (III), or (IV), synthetic methods for making a compound of Formula (I), (Ia), (Ib), (II), (III), or (IV), and pharmaceutical compositions containing a compound of Formula (I), (Ia), (Ib), (II), (III), or (IV).

The present invention also provides compounds and methods for the treatment of psoriasis by administering to a subject in need thereof, a therapeutically effective amount of a compound of Formula (I), (Ia), (Ib), (II), (III), or (IV), or a pharmaceutically acceptable salt, polymorph, hydrate, solvate or co-crystal thereof.

The present invention provides, in part, methods for the treatment of a neurological disease by administering to a subject in need thereof, a therapeutically effective amount of a compound of Formula (I), (Ia), (Ib), (II), (III), or (IV), or a pharmaceutically acceptable salt, polymorph, hydrate, solvate or co-crystal thereof. The neurological disease can be multiple sclerosis. The present invention further provides the use of a compound of Formula (I), (Ia), (Ib), (II), (III), or (IV), or a pharmaceutically acceptable salt, polymorph, hydrate, solvate or co-crystal thereof, for the preparation of a medicament useful for the treatment of a neurological disease.

According to the present invention, a neurological disease is a disorder of the brain, spinal cord or nerves in a subject. In one embodiment, the neurological disease is characterized by demyelination, or degeneration of the myelin sheath, of the central nervous system. The myelin sheath facilitates the transmission of nerve impulses through a nerve fiber or axon. In another embodiment, the neurological disease is selected from the group consisting of multiple sclerosis, Alzheimer's disease, cerebral palsy, spinal cord injury, Amyotrophic lateral sclerosis (ALS), stroke, Huntington's disease, Parkinson's disease, optic neuritis, Devic disease, transverse myelitis, acute disseminated encephalomyelitis, adrenoleukodystrophy and adrenomyeloneuropathy, acute inflammatory demyelinating polyneuropathy (AIDP), chronic inflammatory demyelinating polyneuropathy (CIDP), acute transverse myelitis, progressive multifocal leucoencephalopathy (PML), acute disseminated encephalomyelitis (ADEM), and other hereditary disorders, such as leukodystrophies, Leber's optic atrophy, and Charcot-Marie-Tooth disease. In some embodiments, the neurological disorder is an auto-immune disease. In one embodiment, the neurological disease is multiple sclerosis. In another embodiment, the neurological disease is stroke. In another embodiment, the neurological disease is Alzheimer's disease. In another embodiment, the neurological disease is cerebral palsy. In another embodiment, the neurological disease is spinal cord injury. In another embodiment, the neurological disease is ALS. In another embodiment, the neurological disease is Huntington's disease. See, e.g., U.S. Pat. No. 8,007,826, WO2005/099701 and WO2004/082684, which are incorporated by reference in their entireties.

In a further embodiment, the present invention provides methods for the treatment of a disease or a symptom of a disease described herein by administering to a subject in need thereof, a therapeutically effective amount of a compound of Formula (I), (Ia), (Ib), (II), (III), or (IV), or a pharmaceutically acceptable salt, polymorph, hydrate, solvate or co-crystal thereof. The present invention further provides the use of a compound of Formula (I), (Ia), (Ib), (II), (III), or (IV), or a pharmaceutically acceptable salt, polymorph, hydrate, solvate or co-crystal thereof, for the preparation of a medicament useful for the treatment of a disease or a symptom of a disease described herein.

In another embodiment, the present invention provides a compound of Formula (I), or a pharmaceutically acceptable salt, polymorph, hydrate, solvate or co-crystal thereof, or a method for the treatment of a neurological disease by administering to a subject in need thereof, a therapeutically effective amount of a compound of Formula (I), or a pharmaceutically acceptable salt, polymorph, hydrate, solvate or co-crystal thereof:

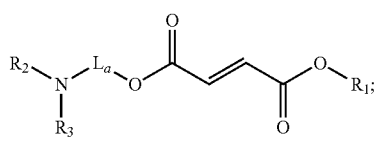
(I)

wherein:
$R_1$ is unsubstituted $C_1$-$C_6$ alkyl;
$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S; and
$R_2$ and $R_3$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;
or alternatively, $R_2$ and $R_3$, together with the nitrogen atom to which they are attached, form a substituted or unsubstituted heteroaryl comprising one or two 5- or 6-member rings and 1-4 heteroatoms selected from N, O and S or a substituted or unsubstituted heterocycle comprising one or two 5- or 6-member rings and 1-4 heteroatoms selected from N, O and S.

In one aspect of the compound of Formula (I), or a pharmaceutically acceptable salt, polymorph, hydrate, solvate or co-crystal thereof:
$R_1$ is unsubstituted $C_1$-$C_6$ alkyl;
$L_a$ is unsubstituted $C_1$-$C_6$ alkyl linker, unsubstituted $C_3$-$C_{10}$ carbocycle, unsubstituted $C_6$-$C_{10}$ aryl, unsubstituted heterocycle comprising one or two 5- or 6-member rings and 1-4 heteroatoms selected from N, O and S, or unsubstituted heteroaryl comprising one or two 5- or 6-member rings and 1-4 heteroatoms selected from N, O and S; and
$R_2$ and $R_3$ are each, independently, H, $C_1$-$C_6$ alkyl, $C_2$-$C_6$ alkenyl, $C_6$-$C_{10}$ aryl, $C_3$-$C_{10}$ carbocycle, heterocycle comprising one or two 5- or 6-member rings and 1-4 heteroatoms selected from N, O and S, or heteroaryl comprising one or two 5- or 6-member rings and 1-4 heteroatoms selected from N, O and S, wherein the alkyl, alkenyl, aryl, carbocycle, heterocycle, or heteroaryl groups may be optionally independently substituted one or more times with $C_1$-$C_3$-alkyl, OH, O($C_1$-$C_4$ alkyl), carbonyl, halo, $NH_2$, N(H)($C_1$-$C_6$ alkyl), N($C_1$-$C_6$ alkyl)$_2$, $SO_2H$, $SO_2$($C_1$-$C_6$ alkyl), CHO, $CO_2H$, $CO_2$($C_1$-$C_6$ alkyl), or CN;
or alternatively, $R_2$ and $R_3$, together with the nitrogen atom to which they are attached, form a heteroaryl comprising one or two 5- or 6-member rings and 1-4 heteroatoms selected from N, O and S; or a heterocycle comprising one or two 5- or 6-member rings and 1-4 heteroatoms selected from N, O and S, wherein the heteroaryl or heterocycle may be optionally substituted one or more times with $C_1$-$C_6$ alkyl, CN, OH, halo, O($C_1$-$C_6$ alkyl), CHO, carbonyl, thione, NO, or $NH_2$.

In one embodiment of this aspect, at least one of $R_1$ and $R^2$ is H.

In another embodiment of this aspect, $L_a$ is $(CH_2)_2$.

In another embodiment of Formula (I), $R_2$ and $R_3$ together with the nitrogen to which they are attached form a heteroaryl, wherein the heteroaryl ring is a pyrrole ring, a pyrazole ring, an imidazole ring, a benzimidazole ring, a thiazole ring, a 1H-1,2,4-triazole ring, a 1H-1,2,3-triazole ring, a 1H-tetrazole ring, a pyrimidinone ring, an indole ring, or a benzoisothiazole ring, wherein all of the rings may be optionally substituted one or more times with $C_1$-$C_6$ alkyl, CN, OH, O($C_1$-$C_6$ alkyl), CHO, $NO_2$, or $NH_2$.

In still another embodiment of Formula (I), $R_2$ and $R_3$ together with the nitrogen to which they are attached form a heterocycle, wherein the heterocycle is a morpholine ring, a thiomorpholine ring, a pyrrolidine ring, a 2,5-dihydropyrrole ring, a 1,2-dihydropyridine ring, a piperazine ring, a succinimide ring, an isoindoline ring, a 2,5-dihydro-1H-tetrazole ring, an azetidine ring, a piperidine ring, a hexahydropyrimidine ring, a 2,3,3a,4,7,7a-hexahydro-1H-4,7-epoxyisoindole ring, a 3,4-dihydroquinazoline ring, a 1,2,3,4-tetrahydroquinazoline ring, an oxazolidine ring, an oxazolidinone ring, an imidazolidinone ring, a 1,3-dihydro-2H-imidazol-2-one ring, an imidizolidine thione ring, or an isothiazolidine ring, wherein all of the rings may be optionally substituted one or more times with $C_1$-$C_6$ alkyl, $CO_2$($C_1$-$C_6$ alkyl), OH, $(CH_2)_{1-4}OH$, $O(C_1$-$C_6$ alkyl), halo, $NH_2$, $(CH_2)_{1-4}NH_2$, $(CH_2)_{1-4}NH(C_1$-$C_4$ alkyl), $(CH_2)_{1-4}N(C_1$-$C_4$alkyl$)_2$, carbonyl, or thione.

In one embodiment of Formula (I):
$R_1$ is unsubstituted $C_1$-$C_3$ alkyl;
$L_a$ is $(CH_2)_{1-6}$; and
$R_2$ and $R_3$ are each, independently: H, methyl, ethyl, isopropyl, butyl, tert-butyl, cyclohexyl, cyclohexenyl, phenyl, benzyl, benzodioxole, pyridinyl, $(CH_2)_2N(CH_3)_2$, $(CH_2)_3SO_2H$, $(CH_2)_2SO_2Me$, $CH_2CO_2H$, or $(CH_2)_2CN$,
or alternatively, $R_2$ and $R_3$, together with the nitrogen atom to which they are attached, form a morpholine ring optionally substituted one or more times with $C_1$-$C_4$ alkyl, carbonyl, or $(CH_2)_{1-3}N(C_1$-$C_4$ alkyl$)_2$; an 8-oxa-3-azabicyclo[3.2.1]octane ring; a 1,4-dioxa-8-azaspiro[4.5]decane ring; a thiomorpholine ring substituted one or more times with carbonyl or thione; a piperazine ring optionally substituted with $C_1$-$C_4$ alkyl, halo, $(CH_2)_2OH$, $C_1$-$C_4$ alkyl ester; a pyrrolidine ring optionally substituted one or more times with $C_1$-$C_4$ alkyl or carbonyl; a 2,5-dihydropyrrole ring optionally substituted one or more times with $C_1$-$C_4$ alkyl or carbonyl; a succinimide ring optionally substituted one or more times with $C_1$-$C_4$ alkyl; a 3-azabicyclo[3.1.0]hexane-2,4-dione ring; a hexahydropyrimidine ring optionally substituted one or more times with $C_1$-$C_4$ alkyl or carbonyl; a pyrimidinone ring optionally substituted one or more times with $C_1$-$C_4$ alkyl; a pyrrole ring optionally substituted one or more times with $C_1$-$C_4$ alkyl, halo, $C(O)NH_2$, or $NO_2$; a pyrazole ring optionally substituted one or more times with $C_1$-$C_4$ alkyl, $C(O)NH_2$, or $NO_2$; an imidazole ring optionally substituted one or more times with $C_1$-$C_4$ alkyl or $NO_2$; a 1,3-dihydro-2H-imidazol-2-one ring; a benzimidazole ring; a thiazole ring; an isoindoline ring substituted with carbonyl; a 1H-tetrazole ring; a 1H 2,5-dihydro-1H-tetrazole ring substituted with thione; a 1H-1,2,4-triazole ring; a 1H-1,2,3-triazole ring; an azetidine ring substituted with carbonyl; an piperidine ring optionally substituted one or more times with $C_1$-$C_4$ alkyl, carbonyl, halo, OH, or $(CH_2)_{1-4}OH$; a pyridinone ring optionally substituted one or more times with $C_1$-$C_4$ alkyl, OH, or CN; a 1,2-dihydropyridine ring substituted with carbonyl; a pyrimidinone ring optionally substituted one or more times with $C_1$-$C_4$ alkyl; an oxazolidine ring optionally substituted one or more times with $C_1$-$C_4$ alkyl; an oxazolidinone ring; an imidazolidinone ring optionally substituted one or more times with $C_1$-$C_4$ alkyl or carbonyl; an imidizolidine thione ring; an isothiazolidine ring optionally substituted one or more times with carbonyl; an indole ring; a 2,3,3a,4,7,7a-hexahydro-1H-4,7-epoxyisoindole ring optionally substituted one or more times with carbonyl; a 3,4-dihydroquinazoline ring substituted with carbonyl; 1,2,3,4-tetrahydroquinazoline ring substituted one or more times with carbonyl; or a benzoisothiazole ring optionally substituted one or more times with carbonyl.

In another embodiment of Formula (I):
$R_1$ is unsubstituted $C_1$-$C_3$ alkyl;
$L_a$ is $(CH_2)_{1-6}$; and
$R_2$ and $R_3$ are each, independently: H, methyl, ethyl, isopropyl, butyl, tert-butyl, cyclohexyl, phenyl, benzyl, benzodioxole, pyridinyl, $(CH_2)_2N(CH_3)_2$, $(CH_2)_3SO_2H$, $(CH_2)_2SO_2Me$, $CH_2CO_2H$, or $(CH_2)_2CN$;
or alternatively, $R_2$ and $R_3$, together with the nitrogen atom to which they are attached, form a morpholine ring optionally substituted one or more times with $C_1$-$C_4$ alkyl, carbonyl, or $(CH_2)_{1-3}N(C_1$-$C_4$ alkyl$)_2$; an 8-oxa-3-azabicyclo[3.2.1]octane ring; a thiomorpholine ring substituted one or more times with carbonyl or thione; a piperazine ring substituted with $C_1$-$C_4$ alkyl ester; a pyrrolidine ring optionally substituted one or more times with $C_1$-$C_4$ alkyl or carbonyl; a 2,5-dihydropyrrole ring optionally substituted one or more times with $C_1$-$C_4$ alkyl or carbonyl; a succinimide ring optionally substituted one or more times with $C_1$-$C_4$ alkyl; a 3-azabicyclo[3.1.0]hexane-2,4-dione ring; a hexahydropyrimidine ring optionally substituted one or more times with $C_1$-$C_4$ alkyl or carbonyl; a pyrimidinone ring optionally substituted one or more times with $C_1$-$C_4$ alkyl; an imidazole ring substituted with $NO_2$; an isoindoline ring substituted with carbonyl; an azetidine ring substituted with carbonyl; an piperidine ring optionally substituted one or more times with $C_1$-$C_4$ alkyl, carbonyl, halo, OH, or $(CH_2)_{1-4}OH$; a pyridinone ring optionally substituted one or more times with $C_1$-$C_4$ alkyl, OH, or CN; a pyrimidinone ring optionally substituted one or more times with $C_1$-$C_4$ alkyl; an oxazolidine ring optionally substituted one or more times with $C_1$-$C_4$ alkyl; an oxazolidinone ring; an imidazolidinone ring optionally substituted one or more times with $C_1$-$C_4$ alkyl or carbonyl; an imidizolidine thione ring; an isothiazolidine ring optionally substituted one or more times with carbonyl; or a benzoisothiazole ring optionally substituted one or more times with carbonyl.

In one aspect of the compound of Formula (I), or a pharmaceutically acceptable salt, polymorph, hydrate, solvate or co-crystal thereof:
$R_1$ is unsubstituted $C_1$-$C_6$ alkyl;
$L_a$ is unsubstituted $C_1$-$C_6$ alkyl linker, unsubstituted $C_3$-$C_{10}$ carbocycle, unsubstituted $C_6$-$C_{10}$ aryl, unsubstituted heterocycle comprising one or two 5- or 6-member rings and 1-4 heteroatoms selected from N, O and S, or unsubstituted heteroaryl comprising one or two 5- or 6-member rings and 1-4 heteroatoms selected from N, O and S; and
or $R_2$ and $R_3$, together with the nitrogen atom to which they are attached, form a heteroaryl comprising one or two 5- or 6-member rings and 1-4 heteroatoms selected from N, O and S; or a heterocycle comprising a 5-member ring and 1-3 heteroatoms selected from N, O and S, wherein the heteroaryl or heterocycle may be optionally substituted one or more times with $C_1$-$C_6$ alkyl, CN, OH, halo, $O(C_1$-$C_6$ alkyl), CHO, carbonyl, thione, NO, or $NH_2$.

In one embodiment of this aspect, at least one of $R_2$ and $R_3$ is H.

In another embodiment of this aspect, $L_a$ is $(CH_2)_2$.

In still another embodiment of Formula (I), $R_2$ and $R_3$ together with the nitrogen to which they are attached form a heterocycle, wherein the heterocycle is, a thiomorpholine ring, a pyrrolidine ring, a 2,5-dihydropyrrole ring, a 1,2-dihydropyridine ring, a piperazine ring, a succinimide ring, an isoindoline ring, a 2,5-dihydro-1H-tetrazole ring, an azetidine ring, a piperidine ring, a hexahydropyrimidine ring, a 2,3,3a,4,7,7a-hexahydro-1H-4,7-epoxyisoindole ring, a 3,4-dihydroquinazoline ring, a 1,2,3,4-tetrahydroquinazoline ring, an oxazolidine ring, an oxazolidinone ring, an imidazolidinone ring, a 1,3-dihydro-2H-imidazol-2-one ring, an imidizolidine thione ring, or an isothiazolidine ring, wherein all of the rings may be optionally substituted one or more times with $C_1$-$C_6$ alkyl, $CO_2(C_1$-$C_6$ alkyl), OH, $(CH_2)_{1-4}$OH, $O(C_1$-$C_6$ alkyl), halo, $NH_2$, $(CH_2)_{1-4}NH_2$, $(CH_2)_{1-4}NH(C_1$-$C_4$ alkyl), $(CH_2)_{1-4}N(C_1$-$C_4$ alkyl)$_2$, carbonyl, or thione.

In one embodiment of Formula (I):
$R_1$ is unsubstituted $C_1$-$C_3$ alkyl;
$L_a$ is $(CH_2)_{1-6}$; and
$R_2$ and $R_3$, together with the nitrogen atom to which they are attached, form a morpholine ring substituted one or more times with $C_1$-$C_4$ alkyl, carbonyl, or $(CH_2)_{1-3}N(C_1$-$C_4$ alkyl)$_2$; an 8-oxa-3-azabicyclo[3.2.1]octane ring; a 1,4-dioxa-8-azaspiro[4.5]decane ring; a thiomorpholine ring substituted one or more times with carbonyl or thione; a piperazine ring optionally substituted with $C_1$-$C_4$ alkyl, halo, $(CH_2)_2$OH, $C_1$-$C_4$ alkyl ester; a pyrrolidine ring optionally substituted one or more times with $C_1$-$C_4$ alkyl or carbonyl; a 2,5-dihydropyrrole ring optionally substituted one or more times with $C_1$-$C_4$ alkyl or carbonyl; a succinimide ring optionally substituted one or more times with $C_1$-$C_4$ alkyl; a 3-azabicyclo[3.1.0]hexane-2,4-dione ring; a hexahydropyrimidine ring optionally substituted one or more times with $C_1$-$C_4$ alkyl or carbonyl; a pyrimidinone ring optionally substituted one or more times with $C_1$-$C_4$ alkyl; a pyrrole ring optionally substituted one or more times with $C_1$-$C_4$ alkyl, halo, $C(O)NH_2$, or $NO_2$; a pyrazole ring optionally substituted one or more times with $C_1$-$C_4$ alkyl, $C(O)NH_2$, or $NO_2$; an imidazole ring optionally substituted one or more times with $C_1$-$C_4$ alkyl or $NO_2$; a 1,3-dihydro-2H-imidazol-2-one ring; a benzimidazole ring; a thiazole ring; an isoindoline ring substituted with carbonyl; a 1H-tetrazole ring; a 1H 2,5-dihydro-1H-tetrazole ring substituted with thione; a 1H-1,2,4-triazole ring; a 1H-1,2,3-triazole ring; an azetidine ring substituted with carbonyl; an piperidine ring optionally substituted one or more times with $C_1$-$C_4$ alkyl, carbonyl, halo, OH, or $(CH_2)_{1-4}$OH; a pyridinone ring optionally substituted one or more times with $C_1$-$C_4$ alkyl, OH, or CN; a 1,2-dihydropyridine ring substituted with carbonyl; a pyrimidinone ring optionally substituted one or more times with $C_1$-$C_4$ alkyl; an oxazolidine ring optionally substituted one or more times with $C_1$-$C_4$ alkyl; an oxazolidinone ring; an imidazolidinone ring optionally substituted one or more times with $C_1$-$C_4$ alkyl or carbonyl; an imidizolidine thione ring; an isothiazolidine ring optionally substituted one or more times with carbonyl; an indole ring; a 2,3,3a,4,7,7a-hexahydro-1H-4,7-epoxyisoindole ring optionally substituted one or more times with carbonyl; a 3,4-dihydroquinazoline ring substituted with carbonyl; 1,2,3,4-tetrahydroquinazoline ring substituted one or more times with carbonyl; or a benzoisothiazole ring optionally substituted one or more times with carbonyl.

In some embodiments of Formula (I), at least one of $R^1$ and $R^2$ is H.

In other embodiments of Formula (I), $L_a$ is $(CH_2)_2$.

In a particular embodiment of Formula (I):
$R_1$ is methyl;
$L_a$ is $(CH_2)_2$; and
$R_2$ and $R_3$, together with the nitrogen atom to which they are attached, form a succinimide ring.

In another embodiment of Formula (I):
$R_1$ is methyl;
$L_a$ is $(CH_2)_3$; and
$R_2$ and $R_3$, together with the nitrogen atom to which they are attached, form a succinimide ring.

In still another embodiment of Formula (I):
$R_1$ is methyl;
$L_a$ is $(CH_2)_4$; and
$R_2$ and $R_3$, together with the nitrogen atom to which they are attached, form a succinimide ring.

For example, the neurological disease is multiple sclerosis.

For example, the neurological disease is relapsing-remitting multiple sclerosis (RRMS).

For example, the compound of Formula (I) is a compound listed in Table 1 herein.

For example, in the compound of Formula (I), $R_1$ is methyl.

For example, in the compound of Formula (I), $R_1$ is ethyl.

For example, in the compound of Formula (I), $L_a$ is substituted or unsubstituted $C_1$-$C_6$ alkyl linker.

For example, in the compound of Formula (I), $L_a$ is substituted or unsubstituted $C_1$-$C_3$ alkyl linker.

For example, in the compound of Formula (I), $L_a$ is substituted or unsubstituted $C_2$ alkyl linker.

For example, in the compound of Formula (I), $L_a$ is methyl substituted or unsubstituted $C_2$ alkyl linker.

For example, in the compound of Formula (I), $L_a$ is di-methyl substituted or unsubstituted $C_2$ alkyl linker.

For example, in the compound of Formula (I), $L_a$ is methyl or di-methyl substituted $C_2$ alkyl linker.

For example, in the compound of Formula (I), $L_a$ is unsubstituted $C_2$ alkyl linker.

For example, in the compound of Formula (I), $R_2$ is substituted or unsubstituted $C_1$-$C_6$ alkyl.

For example, in the compound of Formula (I), $R_2$ is unsubstituted $C_1$-$C_6$ alkyl.

For example, in the compound of Formula (I), $R_2$ is unsubstituted $C_1$-$C_3$ alkyl.

For example, in the compound of Formula (I), $R_2$ is unsubstituted $C_1$-$C_2$ alkyl.

For example, in the compound of Formula (I), $R_2$ is $C(O)OR_a$-substituted $C_1$-$C_6$ alkyl, wherein $R_a$ is H or unsubstituted $C_1$-$C_6$ alkyl.

For example, in the compound of Formula (I), $R_2$ is $S(O)(O)R_b$-substituted $C_1$-$C_6$ alkyl, wherein $R_b$ is unsubstituted $C_1$-$C_6$ alkyl.

For example, in the compound of Formula (I), $R_3$ is H.

For example, in the compound of Formula (I), $R_3$ is substituted or unsubstituted $C_1$-$C_6$ alkyl.

For example, in the compound of Formula (I), $R_3$ is unsubstituted $C_1$-$C_6$ alkyl.

For example, in the compound of Formula (I), $R_2$ and $R_3$, together with the nitrogen atom to which they are attached, form a substituted or unsubstituted heteroaryl comprising one or two 5- or 6-member rings and 1-4 heteroatoms selected from N, O and S, or a substituted or unsubstituted heterocycle comprising one or two 5- or 6-member rings and 1-4 heteroatoms selected from N, O and S.

For example, in the compound of Formula (I), $R_2$ and $R_3$, together with the nitrogen atom to which they are attached, form a substituted or unsubstituted heterocycle comprising one or two 5- or 6-member rings and 1-4 heteroatoms selected from N, O and S.

For example, in the compound of Formula (I), $R_2$ and $R_3$, together with the nitrogen atom to which they are attached, form a substituted or unsubstituted pyrrolidinyl, imidazolidinyl, pyrazolidinyl, oxazolidinyl, isoxazolidinyl, triazolidinyl, tetrahydrofuranyl, piperidinyl, piperazinyl, or morpholinyl ring.

For example, in the compound of Formula (I), $R_2$ and $R_3$, together with the nitrogen atom to which they are attached, form a substituted or unsubstituted piperidinyl ring.

For example, in the compound of Formula (I), $R_2$ and $R_3$, together with the nitrogen atom to which they are attached, form an unsubstituted piperidinyl ring.

For example, in the compound of Formula (I), $R_2$ and $R_3$, together with the nitrogen atom to which they are attached, form a halogen substituted piperidinyl ring.

For example, in the compound of Formula (I), $R_2$ and $R_3$, together with the nitrogen atom to which they are attached, form a 4-halogen substituted piperidinyl ring.

For example, in the compound of Formula (I), $R_2$ and $R_3$, together with the nitrogen atom to which they are attached, form an unsubstituted morpholinyl ring.

For example, in the compound of Formula (I), $R_2$ and $R_3$, together with the nitrogen atom to which they are attached, form a morpholino N-oxide ring.

For example, in the compound of Formula (I), $R_2$ and $R_3$, together with the nitrogen atom to which they are attached, form an unsubstituted pyrrolidinyl ring.

For example, in the compound of Formula (I), $R_2$ and $R_3$, together with the nitrogen atom to which they are attached, form a substituted or unsubstituted heteroaryl comprising one or two 5- or 6-member rings and 1-4 heteroatoms selected from N, O and S.

For example, in the compound of Formula (I), $R_2$ is substituted or unsubstituted $C_6$-$C_{10}$ aryl.

For example, in the compound of Formula (I), $R_2$ is unsubstituted $C_6$-$C_{10}$ aryl.

For example, in the compound of Formula (I), $R_2$ is unsubstituted phenyl.

For example, in the compound of Formula (I), $R_2$ is unsubstituted benzyl.

In another embodiment, the present invention provides a compound of Formula (Ia), or a pharmaceutically acceptable salt, polymorph, hydrate, solvate or co-crystal thereof, or a method for the treatment of a neurological disease by administering to a subject in need thereof a therapeutically effective amount of a compound of Formula (Ia), or a pharmaceutically acceptable salt, polymorph, hydrate, solvate or co-crystal thereof:

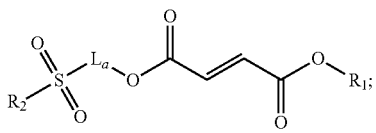

(Ia)

wherein:
$R_1$ is unsubstituted $C_1$-$C_6$ alkyl;
$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S; and
$R_2$ is H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S.

For example, the neurological disease is multiple sclerosis.

For example, the neurological disease is relapsing-remitting multiple sclerosis (RRMS).

For example, in the compound of Formula (Ia), $R_1$ is methyl.

For example, in the compound of Formula (Ia), $R_1$ is ethyl.

For example, in the compound of Formula (Ia), $L_a$ is substituted or unsubstituted $C_1$-$C_6$ alkyl linker.

For example, in the compound of Formula (Ia), $L_a$ is substituted or unsubstituted $C_1$-$C_3$ alkyl linker.

For example, in the compound of Formula (Ia), $L_a$ is substituted or unsubstituted $C_2$ alkyl linker.

For example, in the compound of Formula (Ia), $L_a$ is methyl substituted or unsubstituted $C_2$ alkyl linker.

For example, in the compound of Formula (Ia), $L_a$ is di-methyl substituted or unsubstituted $C_2$ alkyl linker.

For example, in the compound of Formula (Ia), $L_a$ is methyl or di-methyl substituted $C_2$ alkyl linker.

For example, in the compound of Formula (Ia), $L_a$ is unsubstituted $C_2$ alkyl linker.

For example, in the compound of Formula (Ia), $R_2$ is substituted or unsubstituted $C_1$-$C_6$ alkyl.

For example, in the compound of Formula (Ia), $R_2$ is unsubstituted $C_1$-$C_6$ alkyl.

For example, in the compound of Formula (Ia), $R_2$ is methyl.

For example, in the compound of Formula (Ia), $R_2$ is unsubstituted $C_1$-$C_3$ alkyl.

For example, in the compound of Formula (Ia), $R_2$ is unsubstituted $C_1$-$C_2$ alkyl.

For example, in the compound of Formula (Ia), $R_2$ is $C(O)OR_a$-substituted $C_1$-$C_6$ alkyl, wherein $R_a$ is H or unsubstituted $C_1$-$C_6$ alkyl.

For example, in the compound of Formula (Ia), $R_2$ is $S(O)(O)R_b$-substituted $C_1$-$C_6$ alkyl, wherein $R_b$ is unsubstituted $C_1$-$C_6$ alkyl.

In another embodiment, the present invention provides a compound of Formula (Ib), or a pharmaceutically acceptable polymorph, hydrate, solvate or co-crystal thereof, or a method for the treatment of a neurological disease by administering to a subject in need thereof a therapeutically effective amount of a compound of Formula (Ib), or a pharmaceutically acceptable polymorph, hydrate, solvate or co-crystal thereof:

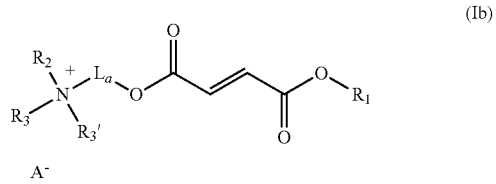

(Ib)

$A^-$ is a pharmaceutically acceptable anion;
$R_1$ is unsubstituted $C_1$-$C_6$ alkyl;
$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

$R_3'$ is substituted or unsubstituted $C_1$-$C_6$ alkyl; and $R_2$ and $R_3$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

or alternatively, $R_2$ and $R_3$, together with the nitrogen atom to which they are attached, form a substituted or unsubstituted heteroaryl comprising one or two 5- or 6-member rings and 1-4 heteroatoms selected from N, O and S, or a substituted or unsubstituted heterocycle comprising one or two 5- or 6-member rings and 1-4 heteroatoms selected from N, O and S.

For example, the neurological disease is multiple sclerosis.

For example, the neurological disease is relapsing-remitting multiple sclerosis (RRMS).

For example, in the compound of Formula (Ib), $R_1$ is methyl.

For example, in the compound of Formula (Ib), $R_1$ is ethyl.

For example, in the compound of Formula (Ib), $L_a$ is substituted or unsubstituted $C_1$-$C_6$ alkyl linker.

For example, in the compound of Formula (Ib), $L_a$ is substituted or unsubstituted $C_1$-$C_3$ alkyl linker.

For example, in the compound of Formula (Ib), $L_a$ is substituted or unsubstituted $C_2$ alkyl linker.

For example, in the compound of Formula (Ib), $L_a$ is methyl substituted or unsubstituted $C_2$ alkyl linker.

For example, in the compound of Formula (Ib), $L_a$ is di-methyl substituted or unsubstituted $C_2$ alkyl linker.

For example, in the compound of Formula (Ib), $L_a$ is methyl or di-methyl substituted or unsubstituted $C_2$ alkyl linker.

For example, in the compound of Formula (Ib), $L_a$ is unsubstituted $C_2$ alkyl linker.

For example, in the compound of Formula (Ib), $R_2$ is substituted or unsubstituted $C_1$-$C_6$ alkyl.

For example, in the compound of Formula (Ib), $R_2$ is unsubstituted $C_1$-$C_6$ alkyl.

For example, in the compound of Formula (Ib), $R_2$ is unsubstituted $C_1$-$C_3$ alkyl.

For example, in the compound of Formula (Ib), $R_2$ is unsubstituted $C_1$-$C_2$ alkyl.

For example, in the compound of Formula (Ib), $R_2$ is $C(O)OR_a$-substituted $C_1$-$C_6$ alkyl, wherein $R_a$ is H or unsubstituted $C_1$-$C_6$ alkyl.

For example, in the compound of Formula (Ib), $R_2$ is $S(O)(O)R_b$-substituted $C_1$-$C_6$ alkyl, wherein $R_b$ is unsubstituted $C_1$-$C_6$ alkyl.

For example, in the compound of Formula (Ib), $R_3$ is H.

For example, in the compound of Formula (Ib), $R_3$ is substituted or unsubstituted $C_1$-$C_6$ alkyl.

For example, in the compound of Formula (Ib), $R_3$ is unsubstituted $C_1$-$C_6$ alkyl.

For example, in the compound of Formula (Ib), $R_2$ and $R_3$, together with the nitrogen atom to which they are attached, form a substituted or unsubstituted heteroaryl comprising one or two 5- or 6-member rings and 1-4 heteroatoms selected from N, O and S, or a substituted or unsubstituted heterocycle comprising one or two 5- or 6-member rings and 1-4 heteroatoms selected from N, O and S.

For example, in the compound of Formula (Ib), $R_2$ and $R_3$, together with the nitrogen atom to which they are attached, form a substituted or unsubstituted heterocycle comprising one or two 5- or 6-member rings and 1-4 heteroatoms selected from N, O and S.

For example, in the compound of Formula (Ib), $R_2$ and $R_3$, together with the nitrogen atom to which they are attached, form a substituted or unsubstituted pyrrolidinyl, imidazolidinyl, pyrazolidinyl, oxazolidinyl, isoxazolidinyl, triazolidinyl, tetrahydrofuranyl, piperidinyl, piperazinyl, or morpholinyl ring.

For example, in the compound of Formula (Ib), $R_2$ and $R_3$, together with the nitrogen atom to which they are attached, form a substituted or unsubstituted piperidinyl ring.

For example, in the compound of Formula (Ib), $R_2$ and $R_3$, together with the nitrogen atom to which they are attached, form an unsubstituted piperidinyl ring.

For example, in the compound of Formula (Ib), $R_2$ and $R_3$, together with the nitrogen atom to which they are attached, form a halogen substituted piperidinyl ring.

For example, in the compound of Formula (Ib), $R_2$ and $R_3$, together with the nitrogen atom to which they are attached, form a 4-halogen substituted piperidinyl ring.

For example, in the compound of Formula (Ib), $R_2$ and $R_3$, together with the nitrogen atom to which they are attached, form an unsubstituted morpholinyl ring.

For example, in the compound of Formula (Ib), $R_2$ and $R_3$, together with the nitrogen atom to which they are attached, form an unsubstituted pyrrolidinyl ring.

For example, in the compound of Formula (Ib), $R_2$ and $R_3$, together with the nitrogen atom to which they are attached, form a substituted or unsubstituted heteroaryl comprising one or two 5- or 6-member rings and 1-4 heteroatoms selected from N, O and S.

For example, in the compound of Formula (Ib), $R_2$ is substituted or unsubstituted $C_6$-$C_{10}$ aryl.

For example, in the compound of Formula (Ib), $R_2$ is unsubstituted $C_6$-$C_{10}$ aryl.

For example, in the compound of Formula (Ib), $R_2$ is unsubstituted phenyl.

For example, in the compound of Formula (Ib), $R_2$ is unsubstituted benzyl.

For example, in the compound of Formula (Ib), $R_3'$ is unsubstituted $C_1$-$C_6$ alkyl.

For example, in the compound of Formula (Ib), $R_3'$ is unsubstituted $C_1$-$C_3$ alkyl.

For example, in the compound of Formula (Ib), $R_3'$ is methyl.

In one embodiment, the present invention provides a compound of Formula (II), or a pharmaceutically acceptable salt, polymorph, hydrate, solvate or co-crystal thereof, or a method for the treatment of a neurological disease by administering to a subject in need thereof a therapeutically effective amount of a compound of Formula (II), or a pharmaceutically acceptable salt, polymorph, hydrate, solvate or co-crystal thereof:

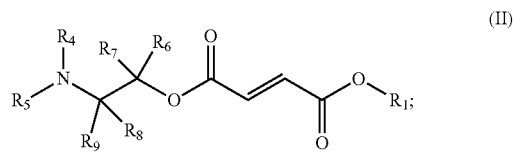

wherein:

$R_1$ is unsubstituted $C_1$-$C_6$ alkyl;

$R_4$ and $R_5$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

$R_6$, $R_7$, $R_8$ and $R_9$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl or $C(O)OR_a$; and $R_a$ is H or substituted or unsubstituted $C_1$-$C_6$ alkyl.

In one embodiment of Formula (II), $R_1$ is methyl;

$R_4$ and $R_5$ are each methyl; and $R_6$, $R_7$, $R_8$ and $R_9$ are each, independently, H or methyl.

For example, the neurological disease is multiple sclerosis.

For example, the neurological disease is relapsing-remitting multiple sclerosis (RRMS).

For example, in the compound of Formula (II), $R_1$ is methyl.

For example, in the compound of Formula (II), $R_1$ is ethyl.

For example, in the compound of Formula (II), $R_4$ is substituted or unsubstituted $C_1$-$C_6$ alkyl.

For example, in the compound of Formula (II), $R_4$ is unsubstituted $C_1$-$C_6$ alkyl.

For example, in the compound of Formula (II), $R_4$ is unsubstituted $C_1$-$C_3$ alkyl.

For example, in the compound of Formula (II), $R_4$ is unsubstituted $C_1$-$C_2$ alkyl.

For example, in the compound of Formula (II), $R_4$ is $C(O)OR_a$-substituted $C_1$-$C_6$ alkyl, wherein $R_a$ is H or unsubstituted $C_1$-$C_6$ alkyl.

For example, in the compound of Formula (II), $R_4$ is $S(O)(O)R_b$-substituted $C_1$-$C_6$ alkyl, wherein $R_b$ is unsubstituted $C_1$-$C_6$ alkyl.

For example, in the compound of Formula (II), $R_5$ is H.

For example, in the compound of Formula (II), $R_5$ is substituted or unsubstituted $C_1$-$C_6$ alkyl.

For example, in the compound of Formula (II), $R_5$ is unsubstituted $C_1$-$C_6$ alkyl.

For example, in the compound of Formula (II), $R_4$ is substituted or unsubstituted $C_6$-$C_{10}$ aryl.

For example, in the compound of Formula (II), $R_4$ is unsubstituted $C_6$-$C_{10}$ aryl.

For example, in the compound of Formula (II), $R_4$ is unsubstituted phenyl.

For example, in the compound of Formula (II), $R_4$ is unsubstituted benzyl.

For example, in the compound of Formula (II), $R_6$, $R_7$, $R_8$ and $R_9$ are each H.

For example, in the compound of Formula (II), $R_6$ is substituted or unsubstituted $C_1$-$C_6$ alkyl and $R_7$, $R_8$ and $R_9$ are each H.

For example, in the compound of Formula (II), $R_6$ is unsubstituted $C_1$-$C_6$ alkyl and $R_7$, $R_8$ and $R_9$ are each H.

For example, in the compound of Formula (II), $R_8$ is substituted or unsubstituted $C_1$-$C_6$ alkyl and $R_6$, $R_7$ and $R_9$ are each H.

For example, in the compound of Formula (II), $R_8$ is unsubstituted $C_1$-$C_6$ alkyl and $R_6$, $R_7$ and $R_9$ are each H.

For example, in the compound of Formula (II), $R_6$ and $R_8$ are each, independently, substituted or unsubstituted $C_1$-$C_6$ alkyl and $R_7$ and $R_9$ are each H.

For example, in the compound of Formula (II), $R_6$ and $R_8$ are each, independently, unsubstituted $C_1$-$C_6$ alkyl and $R_7$ and $R_9$ are each H.

For example, in the compound of Formula (II), $R_6$ and $R_7$ are each, independently, substituted or unsubstituted $C_1$-$C_6$ alkyl and $R_8$ and $R_9$ are each H.

For example, in the compound of Formula (II), $R_6$ and $R_7$ are each, independently, unsubstituted $C_1$-$C_6$ alkyl and $R_8$ and $R_9$ are each H.

For example, in the compound of Formula (II), $R_8$ and $R_9$ are each, independently, substituted or unsubstituted $C_1$-$C_6$ alkyl and $R_6$ and $R_7$ are each H.

For example, in the compound of Formula (II), $R_8$ and $R_9$ are each, independently, unsubstituted $C_1$-$C_6$ alkyl and $R_6$ and $R_7$ are each H.

In one embodiment, the present invention provides a compound of Formula (III), or a pharmaceutically acceptable salt, polymorph, hydrate, solvate or co-crystal thereof, or a method for the treatment of a neurological disease by administering to a subject in need thereof a therapeutically effective amount of a compound of Formula (III), or a pharmaceutically acceptable salt, polymorph, hydrate, solvate or co-crystal thereof:

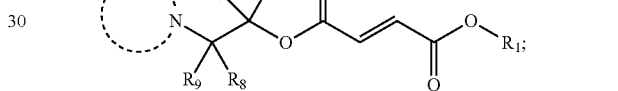

(III)

wherein:

$R_1$ is unsubstituted $C_1$-$C_6$ alkyl;

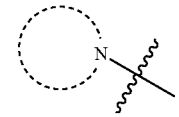

is selected from the group consisting of:

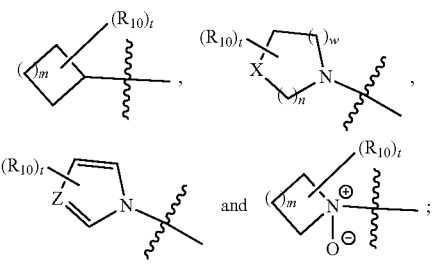

X is N, O, S, or $SO_2$;

Z is C or N;

m is 0, 1, 2, or 3;

n is 1 or 2;

w is 0, 1, 2 or 3;

t is 0, 1, 2, 3, 4, 5, 6, 7, 8, 9, or 10;

$R_6$, $R_7$, $R_8$ and $R_9$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl or $C(O)OR_a$; and $R_a$ is H or substituted or unsubstituted $C_1$-$C_6$ alkyl; and each $R_{10}$ is, independently, H, halogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

or, alternatively, two $R_{10}$'s attached to the same carbon atom, together with the carbon atom to which they are attached, form a carbonyl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

or, alternatively, two $R_{10}$'s attached to different atoms, together with the atoms to which they are attached, form a substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S.

For example, the neurological disease is multiple sclerosis.

For example, the neurological disease is relapsing-remitting multiple sclerosis (RRMS).

For example, in the compound of Formula (III), $R_1$ is methyl.

For example, in the compound of Formula (III), $R_1$ is ethyl.

For example, in the compound of Formula (III),

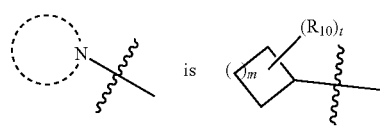

For example, in the compound of Formula (III),

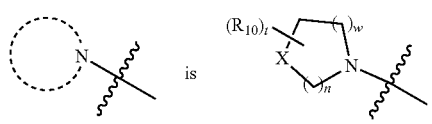

For example, in the compound of Formula (III),

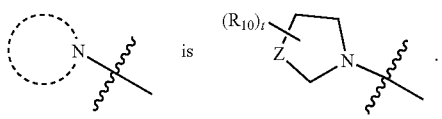

For example, in the compound of Formula (III),

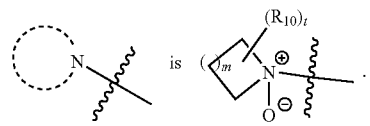

For example, in the compound of Formula $R_6$ is substituted or unsubstituted $C_1$-$C_6$ alkyl and $R_7$, $R_8$ and $R_9$ are each H.

For example, in the compound of Formula (III), $R_6$ is unsubstituted $C_1$-$C_6$ alkyl and $R_7$, $R_8$ and $R_9$ are each H.

For example, in the compound of Formula (III), $R_8$ is substituted or unsubstituted $C_1$-$C_6$ alkyl and $R_6$, $R_7$ and $R_9$ are each H.

For example, in the compound of Formula (III), $R_8$ is unsubstituted $C_1$-$C_6$ alkyl and $R_6$, $R_7$ and $R_9$ are each H.

For example, in the compound of Formula (III), $R_6$ and $R_8$ are each, independently, substituted or unsubstituted $C_1$-$C_6$ alkyl and $R_7$ and $R_9$ are each H.

For example, in the compound of Formula (III), $R_6$ and $R_8$ are each, independently, unsubstituted $C_1$-$C_6$ alkyl and $R_7$ and $R_9$ are each H.

For example, in the compound of Formula (III), $R_6$ and $R_7$ are each, independently, substituted or unsubstituted $C_1$-$C_6$ alkyl and $R_8$ and $R_9$ are each H.

For example, in the compound of Formula (III), $R_6$ and $R_7$ are each, independently, unsubstituted $C_1$-$C_6$ alkyl and $R_8$ and $R_9$ are each H.

For example, in the compound of Formula (III), $R_8$ and $R_9$ are each, independently, substituted or unsubstituted $C_1$-$C_6$ alkyl, and $R_6$ and $R_7$ are each H.

For example, in the compound of Formula (III), $R_8$ and $R_9$ are each, independently, unsubstituted $C_1$-$C_6$ alkyl, and $R_6$ and $R_7$ are each H.

In one embodiment of Formula (III):
$R_1$ is unsubstituted $C_1$-$C_6$ alkyl;

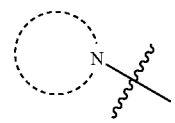

is selected from a group consisting of

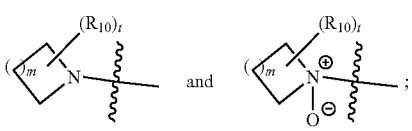

m is 0, 1, 2, or 3;
t is 2, 4, or 6;
$R_6$, $R_7$, $R_8$ and $R_9$ are each, independently, H, unsubstituted $C_1$-$C_6$ alkyl, or C(O)O$R_a$, wherein $R_a$ is H or unsubstituted $C_1$-$C_6$ alkyl; and
two $R_{10}$'s attached to the same carbon atom, together with the carbon atom to which they are attached, form a carbonyl.

In another embodiment, the present invention provides a compound of Formula (IV), or a pharmaceutically acceptable salt, polymorph, hydrate, solvate or co-crystal thereof, or a method for the treatment of a neurological disease by administering to a subject in need thereof, a therapeutically effective amount of a compound of Formula (IV), or a pharmaceutically acceptable salt, polymorph, hydrate, solvate or co-crystal thereof:

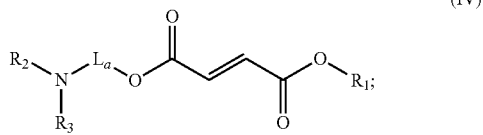

(IV)

wherein:

$R_1$ is unsubstituted $C_1$-$C_6$ alkyl;

$L_a$ is substituted or unsubstituted $C_1$-$C_6$ alkyl linker;

$R_2$ and $R_3$ are each, independently, H, substituted or unsubstituted acyl, $NR_{14}R_{15}$, $C(S)R_{11}$, $C(S)SR_{11}$, $C(S)NR_{11}R_{12}$, $C(S)NR_{11}NR_{13}R_{14}$, $C(NR_{13})NR_{11}R_{12}$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

$R_{11}$ and $R_{12}$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

$R_{13}$ is H or substituted or unsubstituted $C_1$-$C_6$ alkyl; and $R_{14}$ and $R_{15}$ are each, independently, H, substituted or unsubstituted acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S;

wherein at least one of $R_2$ and $R_3$ is substituted or unsubstituted acyl, $NR_{14}R_{15}$, $C(S)R_{11}$, $C(S)SR_{11}$, $C(S)NR_{11}R_{12}$, $C(S)NR_{11}NR_{13}R_{14}$, or $C(NR_{13})NR_{11}R_{12}$.

In one embodiment of Formula (IV), $R_1$ is $C_1$-$C_6$ alkyl;

$L_a$ is substituted or unsubstituted $C_1$-$C_4$ alkyl linker; and one of $R_2$ and $R_3$ is $CO_2(C_1$-$C_6$ alkyl), $CO_2CH_2Ph$, $CO_2Ph$, $CO_2Py$, pyridinyl-N-oxide ester, $C(O)CH_2$(imidazole), $C(S)NHPh$, or $C(NH)NH_2$, wherein Ph or imidazole groups are optionally substituted with $NO_2$.

In another embodiment of Formula (IV), $R_1$ is $C_1$-$C_4$ alkyl;

$L_a$ is substituted or unsubstituted $C_1$-$C_4$ alkyl linker; and $R_2$ and $R_3$ are each, independently, H, methyl, ethyl, isopropyl, butyl, tert-butyl, cyclohexyl, cyclohexenyl, phenyl, benzyl, benzodioxole, pyridinyl, $(CH_2)_2N(CH_3)_2$, $(CH_2)_3SO_2H$, $(CH_2)_2SO_2Me$, CHO, $CH_2CO_2H$, $C(O)(CH_2)_2CO_2H$, NO, $C(O)NH_2$, $(CH_2)_2CN$, tert-butyl ester, benzyl ester, pyridinyl ester, pyridinyl-N-oxide ester, $C(O)CH_2$(2-nitro-1H-imidazol-1-yl), $C(S)NHPh$, $C(NH)NH_2$, ethyl substituted with carbonyl, propyl substituted with carbonyl, or phenyl ester substituted with $NO_2$, wherein the phenyl and benzyl groups can be optionally substituted one or more times with methyl, $NH_2$, $NO_2$, OH, or CHO;

wherein at least one of $R_2$ and $R_3$ is substituted or unsubstituted acyl, $NR_{14}R_{15}$, $C(S)R_{11}$, $C(S)SR_{11}$, $C(S)NR_{11}R_{12}$, $C(S)NR_{11}NR_{13}R_{14}$, or $C(NR_{13})NR_{11}R_{12}$.

In one embodiment of Formula (IV), $R_1$ is $C_1$-$C_6$ alkyl;

$L_a$ is $(CH_2)_{1-4}$;

$R_2$ is H or $C(O)C_1$-$C_6$ alkyl; and $R_3$ is H or $C(O)C_1$-$C_6$ alkyl wherein at least one of $R_2$ and $R_3$ is $C(O)C_{1-6}$ alkyl.

For example, the compound is a compound listed in Table 1 herein.

Representative compounds of the present invention include compounds listed in Table 1 and in Table 2.

TABLE 1

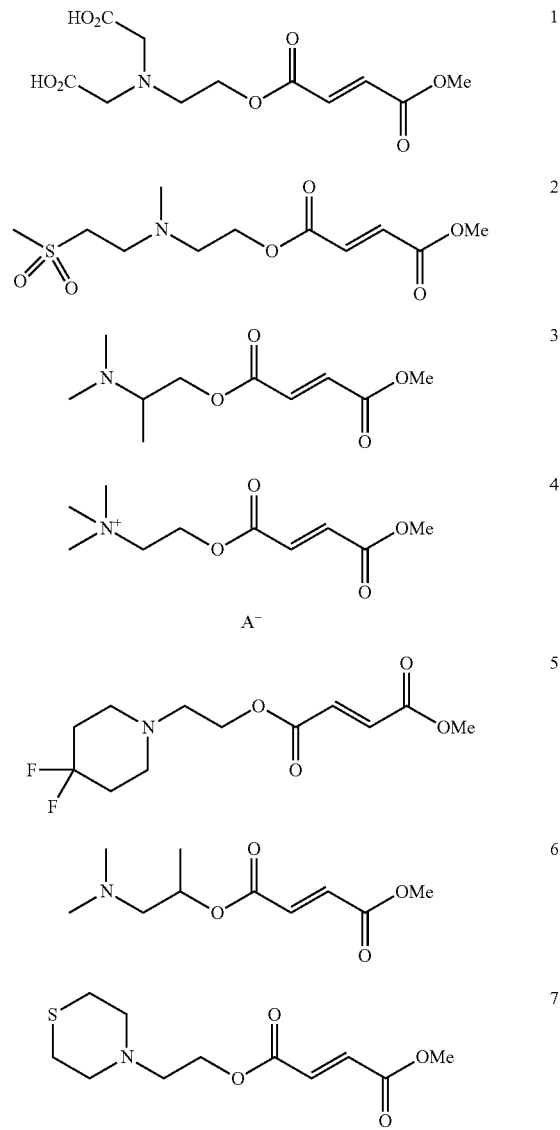

TABLE 1-continued
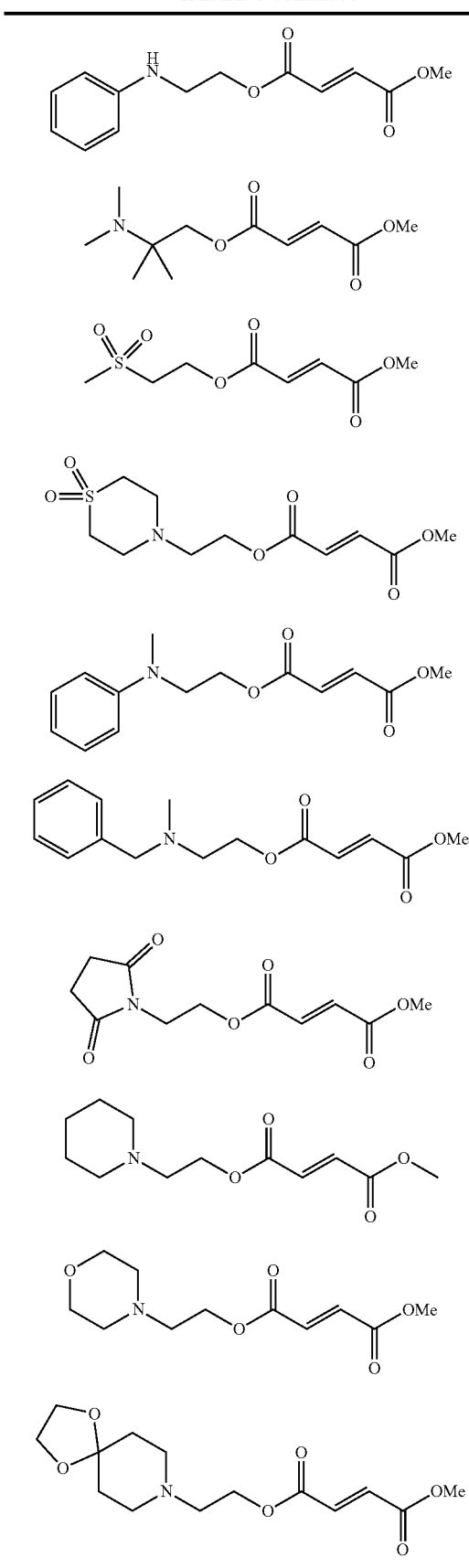
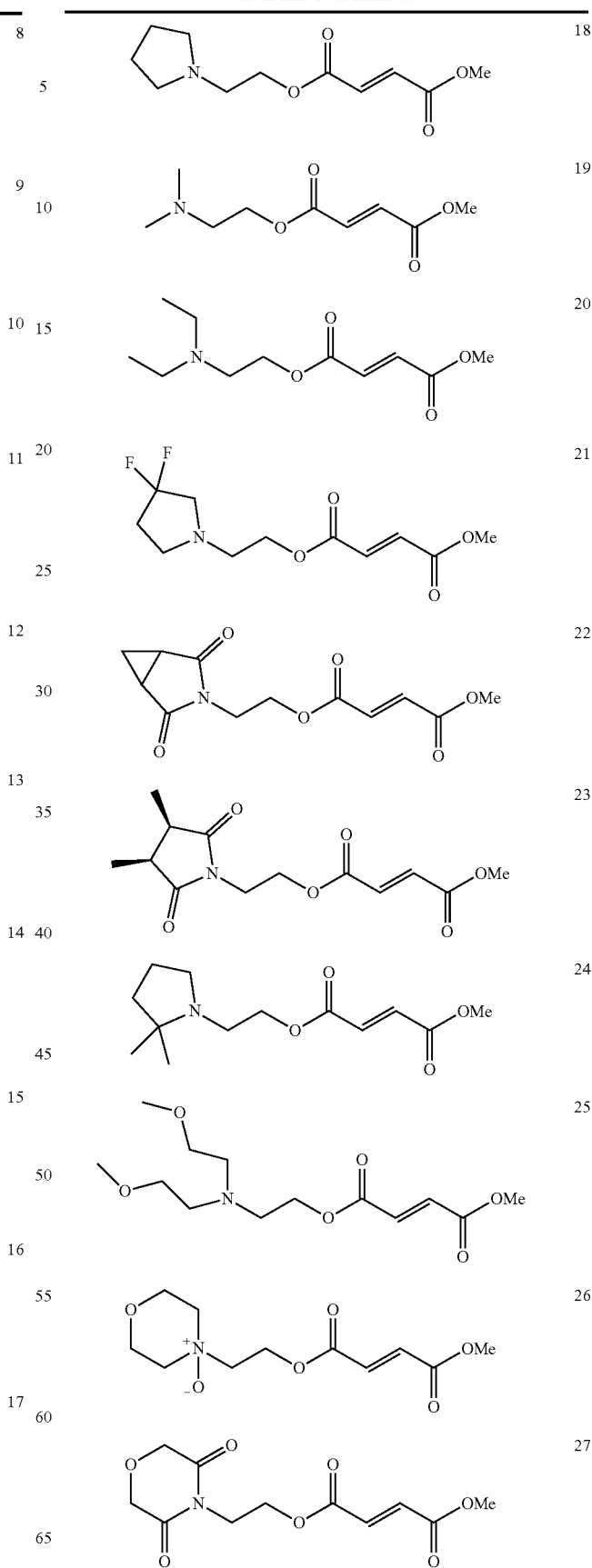

TABLE 1-continued
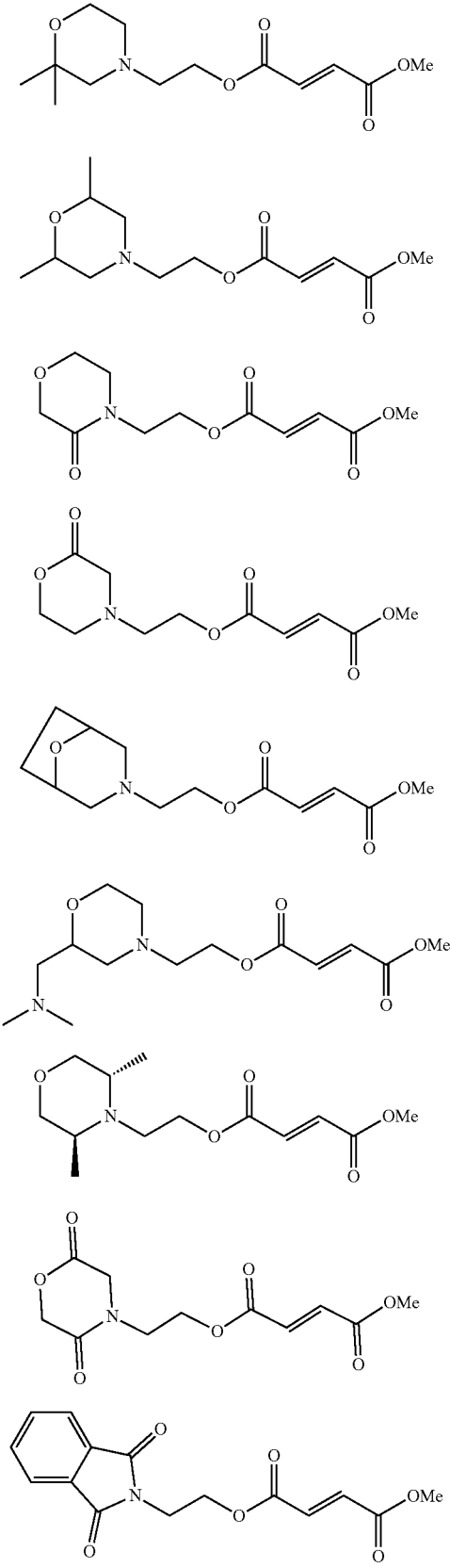
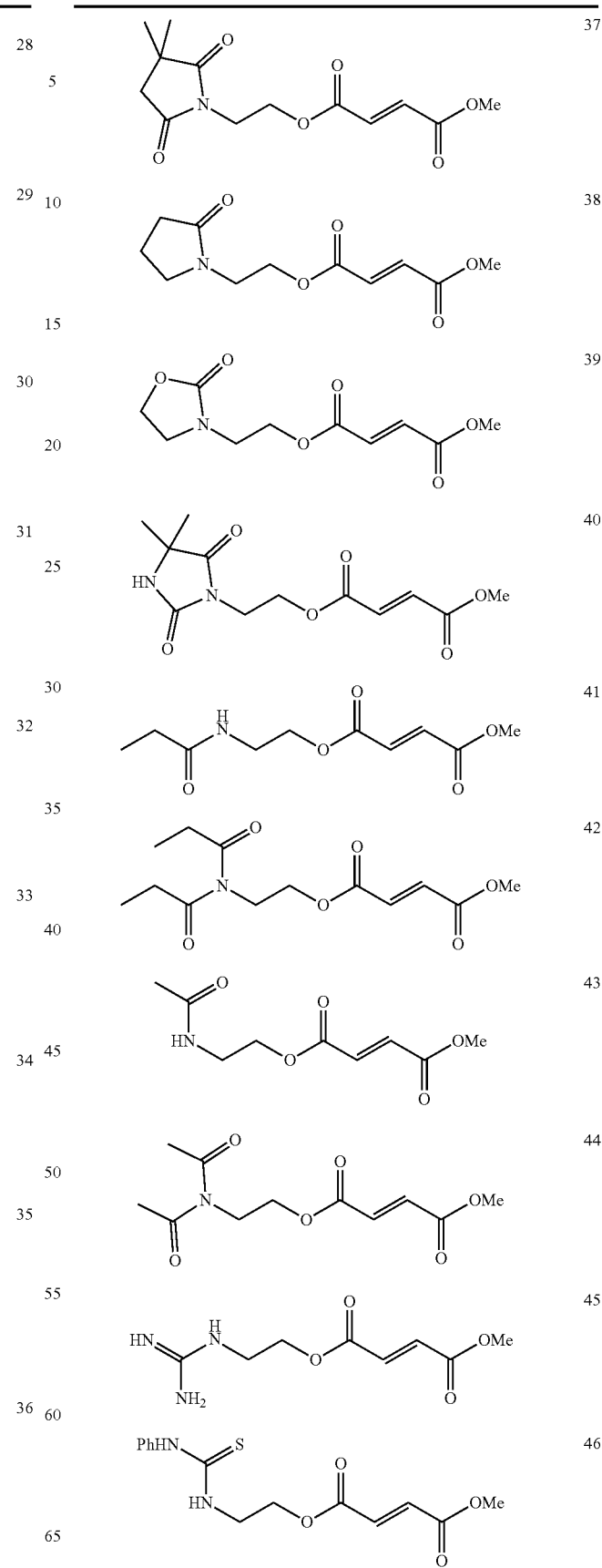

TABLE 1-continued
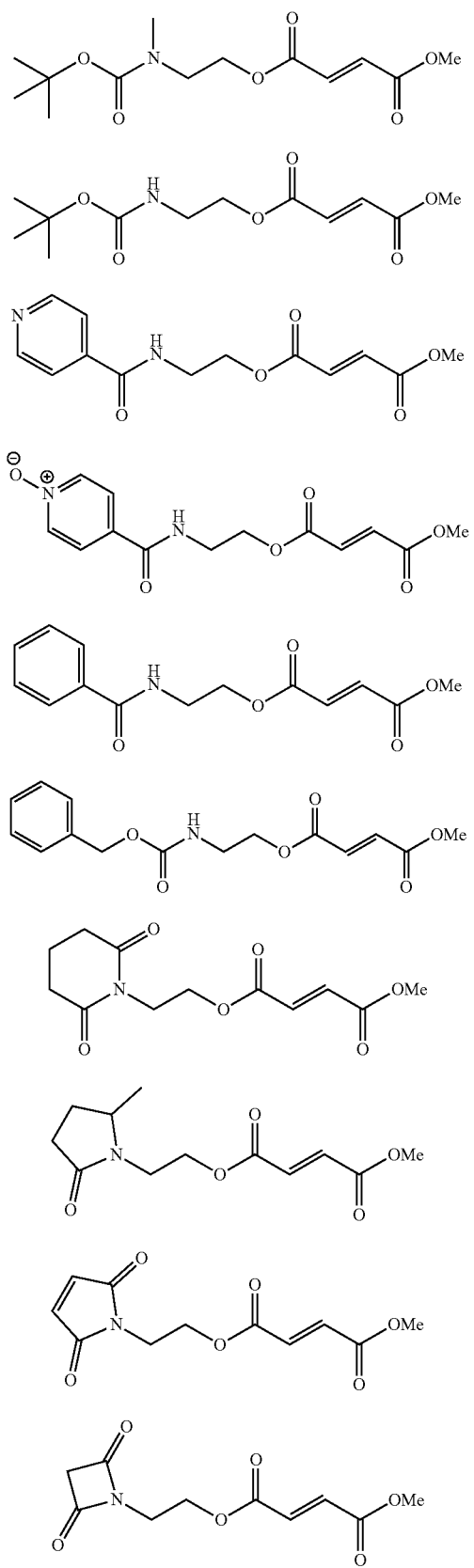
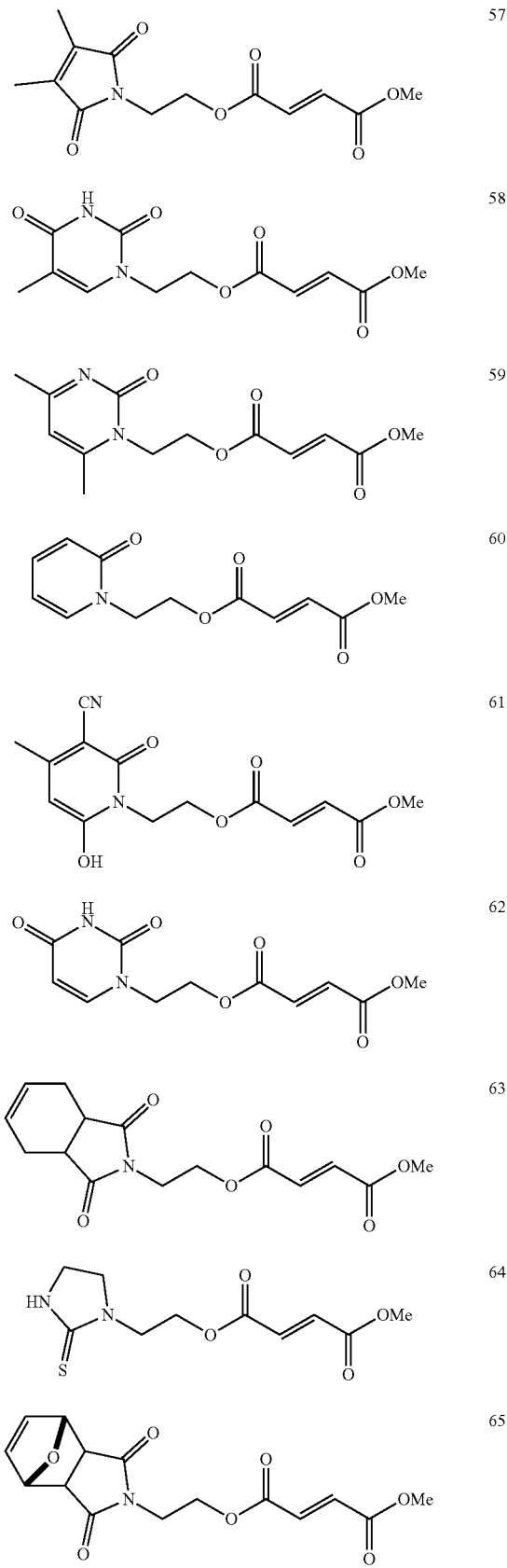

TABLE 1-continued
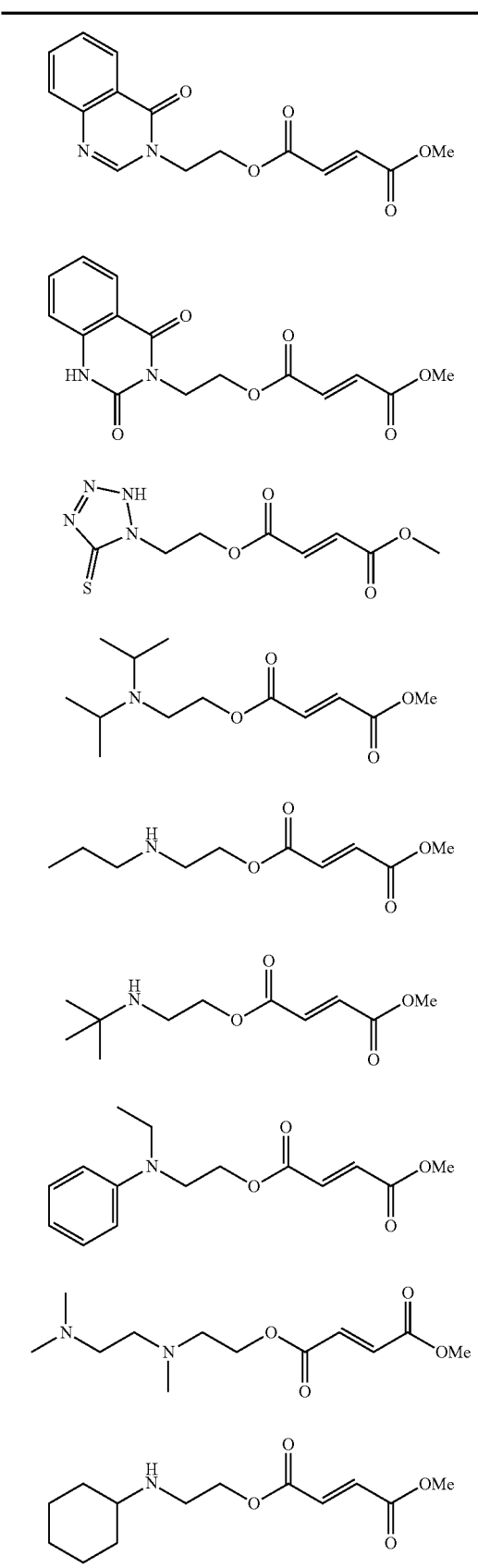
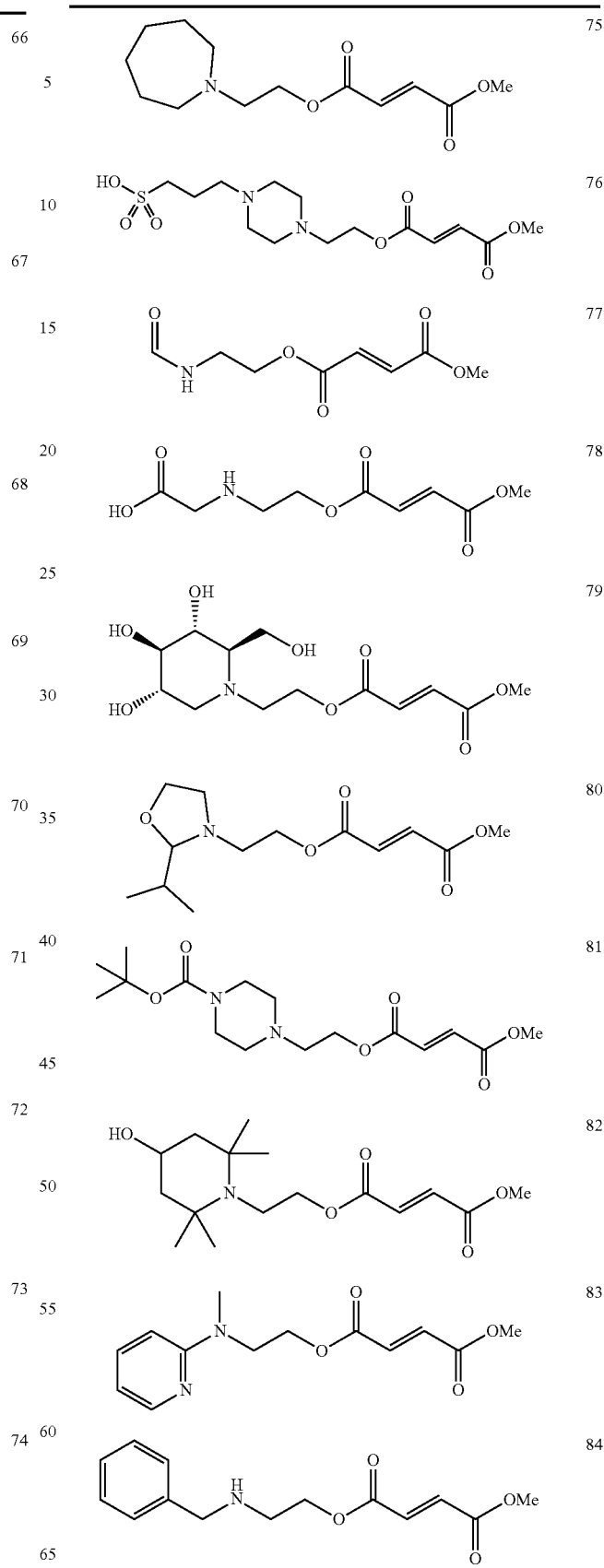

TABLE 1-continued
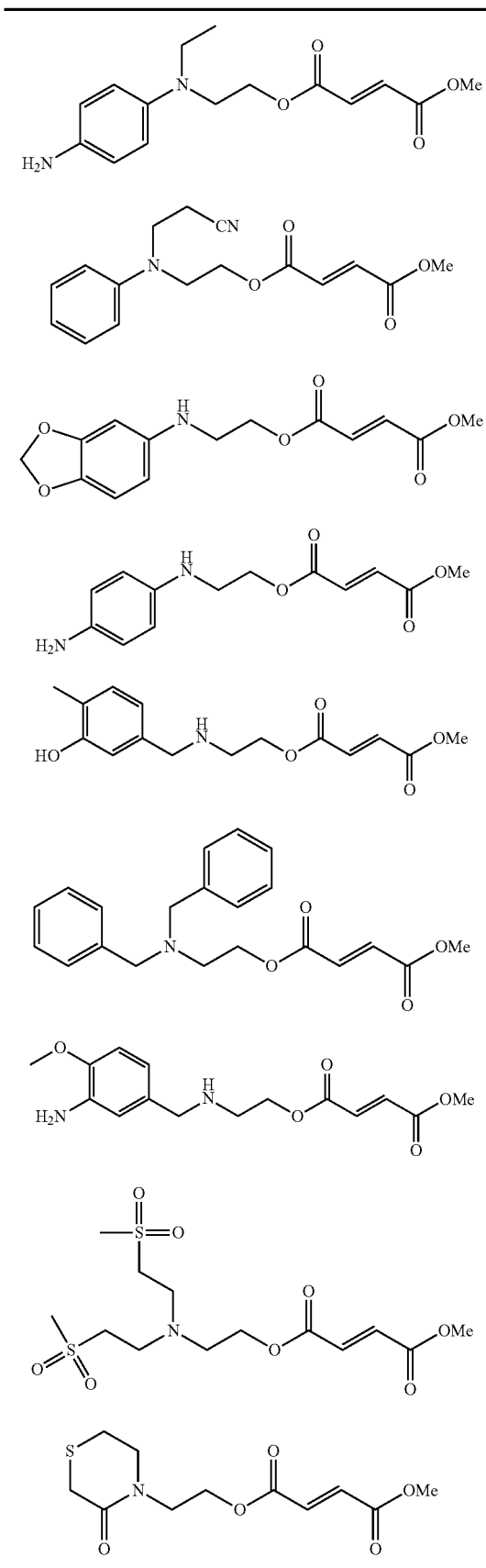
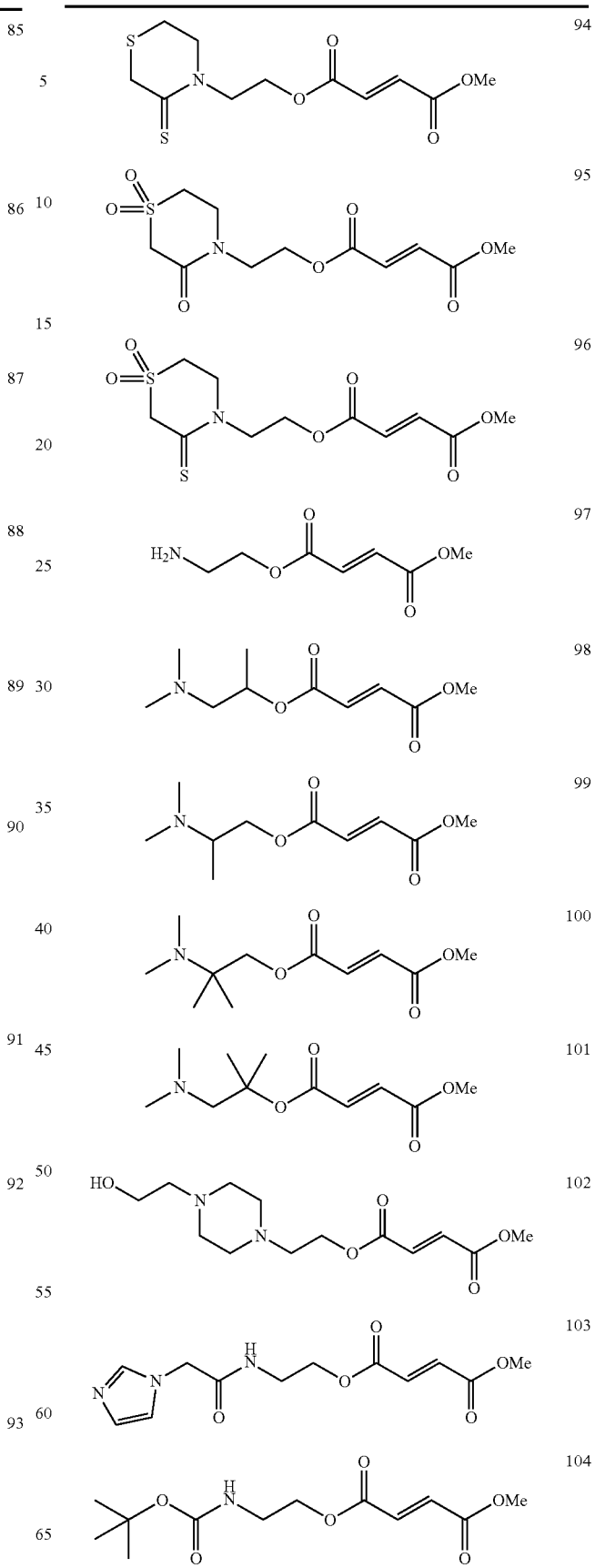

TABLE 1-continued
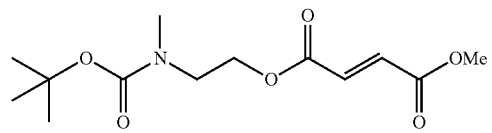 105
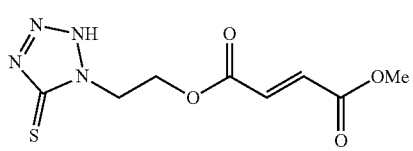 [SMILES: COC(=O)/C=C/C(=O)OCCn1[nH]nnc1=S] 106
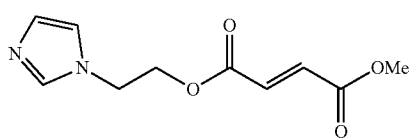 [SMILES: COC(=O)/C=C/C(=O)OCCn1ccnc1] 107
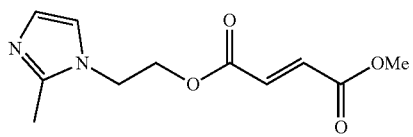 108
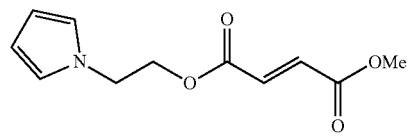 [SMILES: COC(=O)/C=C/C(=O)OCCn1cccc1] 109
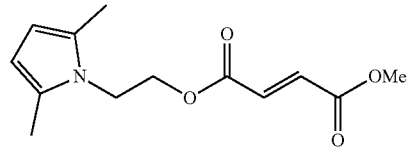 [SMILES: COC(=O)/C=C/C(=O)OCCn1c(C)ccc1C] 110
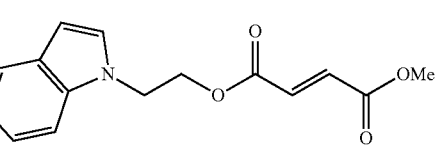 111
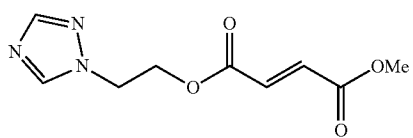 [SMILES: COC(=O)/C=C/C(=O)OCCn1cncn1] 112
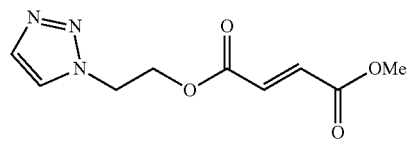 [SMILES: COC(=O)/C=C/C(=O)OCCn1ccnn1] 113
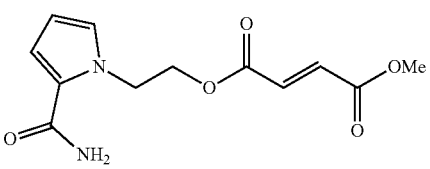 [SMILES: COC(=O)/C=C/C(=O)OCCn1cccc1C(N)=O] 114
TABLE 1-continued
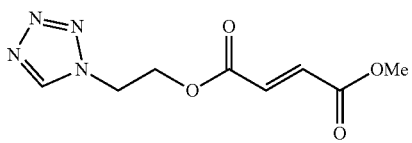 [SMILES: COC(=O)/C=C/C(=O)OCCn1cnnn1] 115
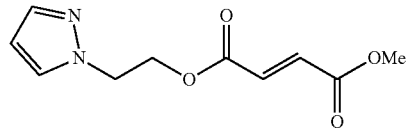 [SMILES: COC(=O)/C=C/C(=O)OCCn1cccn1] 116
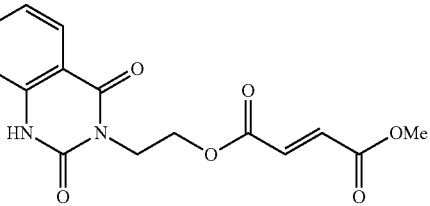 117
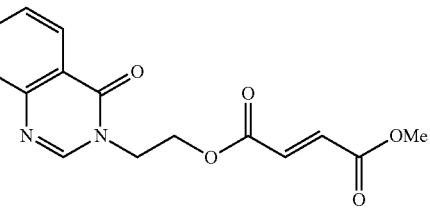 118
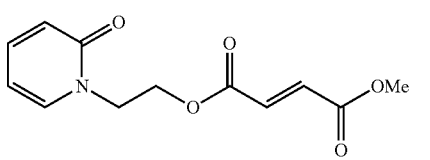 [SMILES: COC(=O)/C=C/C(=O)OCCn1ccccc1=O] 119
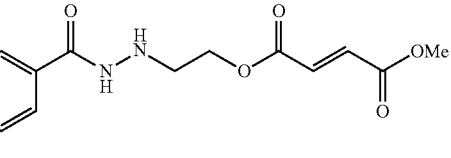 120
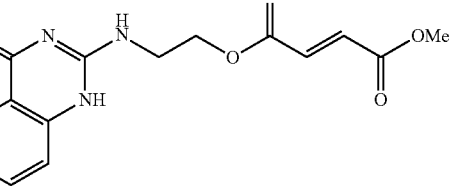 121
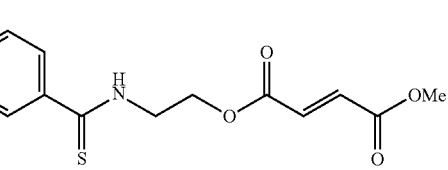 122
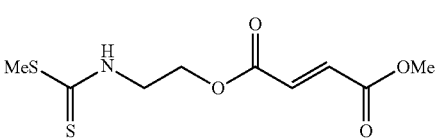 [SMILES: COC(=O)/C=C/C(=O)OCCNC(=S)SC] 123

TABLE 1-continued

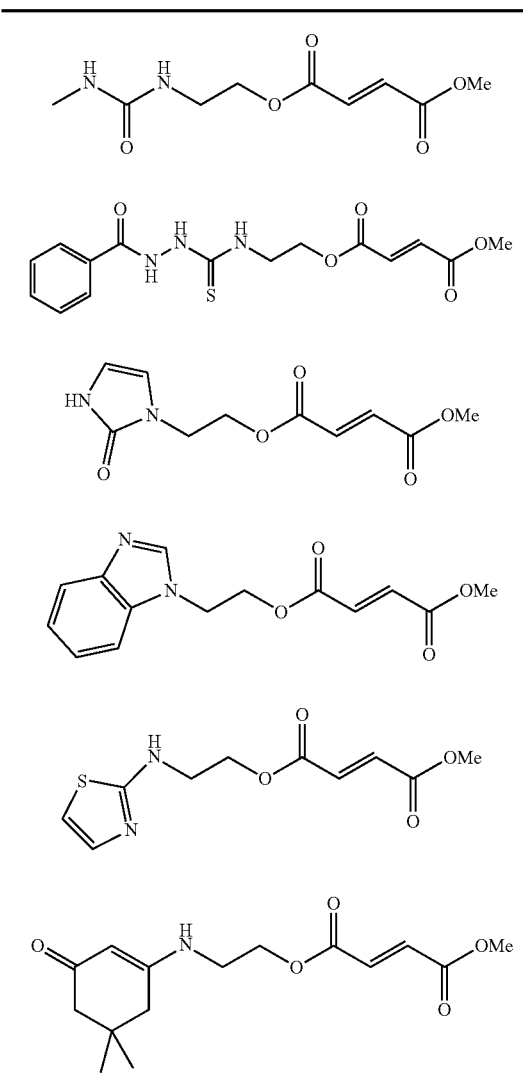

A⁻ is a pharmaceutically acceptable anion.

TABLE 2

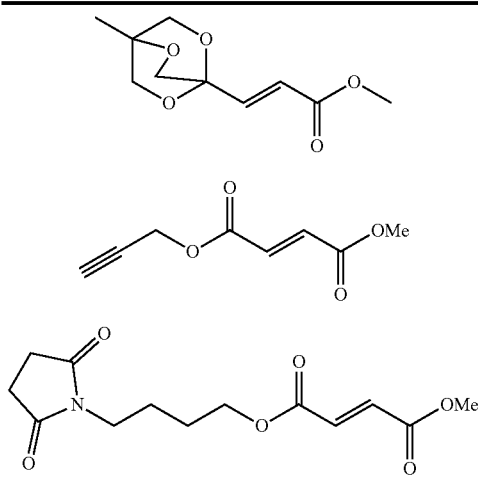

TABLE 2-continued

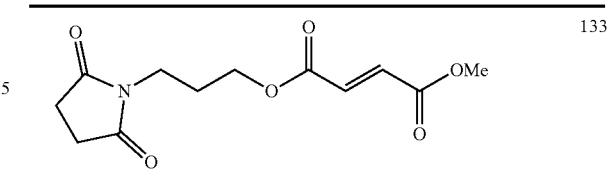

The present invention also provides pharmaceutical compositions comprising one or more compounds of Formula (I), (Ia), (Ib), (II), (III), or (IV) and one or more pharmaceutically acceptable carriers.

In one embodiment, the pharmaceutical composition is a controlled release composition comprising a compound of Formula (I), (Ia), (Ib), (II), (III), or (IV) and one or more pharmaceutically acceptable carriers, wherein the controlled release composition provides a therapeutically effective amount of monomethyl fumarate to a subject. In another embodiment, the pharmaceutical composition is a controlled release composition comprising a compound of Formula (I), (Ia), (Ib), (II), (III), or (IV) and one or more pharmaceutically acceptable carriers, wherein the controlled release composition provides a therapeutically effective amount of monomethyl fumarate to a subject for at least about 8 hours to at least about 24 hours. In another embodiment, the pharmaceutical composition is a controlled release composition comprising a compound of Formula (I), (Ia), (Ib), (II), (III), or (IV) and one or more pharmaceutically acceptable carriers, wherein the controlled release composition provides a therapeutically effective amount of monomethyl fumarate to a subject for at least about 8 hours, at least about 10 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours or at least about 24 hours or longer. For example, at least about 18 hours. For example, at least about 12 hours. For example, greater than 12 hours. For example, at least about 16 hours. For example, at least about 20 hours. For example, at least about 24 hours.

In another embodiment, a compound of Formula (I), (Ia), (Ib), (II), (III), or (IV) is efficiently converted to the active species, i.e., monomethyl fumarate, upon oral administration. For example, about 50 mole percent, about 55 mole percent, about 60 mole percent, about 65 mole percent, about 70 mole percent, about 75 mole percent, about 80 mole percent, about 85 mole percent, about 90 mole percent, or greater than 90 mole percent of the total dose of a compound of Formula (I), (Ia), (Ib), (II), (III), or (IV) administered is converted to monomethyl fumarate upon oral administration. In another embodiment, a compound of Formula (I), (Ia), (Ib), (II), (III), or (IV) is converted to the active species, i.e., monomethyl fumarate, upon oral administration more efficiently than dimethyl fumarate. In another embodiment, a compound of Formula (I), (Ia), (Ib), (II), (III), or (IV) is converted to the active species, i.e., monomethyl fumarate, upon oral administration more efficiently than one or more of the compounds described in U.S. Pat. No. 8,148,414. For example, a compound of Formula (I), (Ia), (Ib), (II), (III), or (IV) is essentially completely converted to the active species, i.e., monomethyl fumarate, upon oral administration. U.S. Pat. No. 8,148,414 is expressly incorporated by reference herein.

In another embodiment, any one of Compounds 1-133 is efficiently converted to the active species, i.e., monomethyl fumarate, upon oral administration. For example, about 50 percent, about 55 percent, about 60 percent, about 65 percent, about 70 percent, about 75 percent, about 80 percent, about 85 percent, about 90 percent, or greater than 90 percent of the total dose of any one of Compounds 1-133 administered is converted to monomethyl fumarate upon oral administration. In another embodiment, any one of Compounds 1-133 is converted to the active species, i.e., monomethyl fumarate, upon oral administration more efficiently than dimethyl fumarate. In another embodiment, any one of Compounds 1-133 is converted to the active species, i.e., monomethyl fumarate, upon oral administration more efficiently than one or more of the compounds described in U.S. Pat. No. 8,148,414. For example, any one of Compounds 1-133 is completely converted to the active species, i.e., monomethyl fumarate, upon oral administration.

For a drug to achieve its therapeutic effect, it is necessary to maintain the required level of blood or plasma concentration. Many drugs, including dimethyl fumarate, must be administered multiple times a day to maintain the required concentration. Furthermore, even with multiple administrations of such a drug per day, the blood or plasma concentrations of the active ingredient may still vary with time, i.e., at certain time points between administrations there are higher concentrations of the active ingredient than at other times. Thus, at certain time points of a 24-hour period, a patient may receive therapeutically effective amounts of the active ingredient, while at other time points the concentration of the active ingredient in the blood may fall below therapeutic levels. Additional problems with such drugs include that multiple dosing a day often adversely affects patient compliance with the treatment. Therefore, it is desirable to have a drug dosage form wherein the active ingredient is delivered in such a controlled manner that a constant or substantially constant level of blood or plasma concentration of the active ingredient can be achieved by one or at most two dosing per day. Accordingly, the present invention provides controlled-release formulations as described below. In general, such formulations are known to those skilled in the art or are available using conventional methods.

As used herein, "controlled-release" means a dosage form in which the release of the active agent is controlled or modified over a period of time. Controlled can mean, for example, sustained, delayed or pulsed-release at a particular time. For example, controlled-release can mean that the release of the active ingredient is extended for longer than it would be in an immediate-release dosage form, i.e., at least over several hours.

As used herein, "immediate-release" means a dosage form in which greater than or equal to about 75% of the active ingredient is released within two hours, or, more specifically, within one hour, of administration. Immediate-release or controlled-release may also be characterized by their dissolution profiles.

Formulations may also be characterized by their pharmacokinetic parameters. As used herein, "pharmacokinetic parameters" describe the in vivo characteristics of the active ingredient over time, including for example plasma concentration of the active ingredient. As used herein, "$C_{max}$" means the measured concentration of the active ingredient in the plasma at the point of maximum concentration. "$T_{max}$" refers to the time at which the concentration of the active ingredient in the plasma is the highest. "AUC" is the area under the curve of a graph of the concentration of the active ingredient (typically plasma concentration) vs. time, measured from one time to another.

The controlled-release formulations provided herein provide desirable properties and advantages. For example, the formulations can be administered once daily, which is particularly desirable for the subjects described herein. The formulation can provide many therapeutic benefits that are not achieved with corresponding shorter acting, or immediate-release preparations. For example, the formulation can maintain lower, more steady plasma peak values, for example, $C_{max}$, so as to reduce the incidence and severity of possible side effects.

Sustained-release dosage forms release their active ingredient into the gastro-intestinal tract of a patient over a sustained period of time following administration of the dosage form to the patient. Particular dosage forms include: (a) those in which the active ingredient is embedded in a matrix from which it is released by diffusion or erosion; (b) those in which the active ingredient is present in a core which is coated with a release rate-controlling membrane; (c) those in which the active ingredient is present in a core provided with an outer coating impermeable to the active ingredient, the outer coating having an aperture (which may be drilled) for release of the active ingredient; (d) those in which the active ingredient is released through a semipermeable membrane, allowing the drug to diffuse across the membrane or through liquid filled pores within the membrane; and (e) those in which the active ingredient is present as an ion exchange complex.

It will be apparent to those skilled in the art that some of the above means of achieving sustained-release may be combined, for example a matrix containing the active compound may be formed into a multiparticulate and/or coated with an impermeable coating provided with an aperture.

Pulsed-release formulations release the active compound after a sustained period of time following administration of the dosage form to the patient. The release may then be in the form of immediate- or sustained-release. This delay may be achieved by releasing the drug at particular points in the gastro-intestinal tract or by releasing drug after a predetermined time. Pulsed-release formulations may be in the form of tablets or multiparticulates or a combination of both. Particular dosage forms include: (a) osmotic potential triggered release (see U.S. Pat. No. 3,952,741); (b) compression coated two layer tablets (see U.S. Pat. No. 5,464,633); (c) capsules containing an erodible plug (see U.S. Pat. No. 5,474,784); sigmoidal releasing pellets (referred to in U.S. Pat. No. 5,112,621); and (d) formulations coated with or containing pH-dependent polymers including shellac, phthalate derivatives, polyacrylic acid derivatives and crotonic acid copolymers.

Dual release formulations can combine the active ingredient in immediate release form with additional active ingredient in controlled-release form. For example, a bilayer tablet can be formed with one layer containing immediate release active ingredient and the other layer containing the active ingredient embedded in a matrix from which it is released by diffusion or erosion. Alternatively, one or more immediate release beads can be combined with one or more beads which are coated with a release rate-controlling membrane in a capsule to give a dual release formulation. Sustained release formulations in which the active ingredient is present in a core provided with an outer coating impermeable to the active ingredient, the outer coating having an aperture (which may be drilled) for release of the active ingredient, can be coated with drug in immediate release form to give a dual release formulation. Dual release formulations can also combine drug in immediate release form with additional drug in pulsed release form. For example, a capsule containing an erodible plug could liberate drug initially and, after a predetermined period of time, release additional drug in immediate- or sustained-release form.

In some embodiments, the dosage forms to be used can be provided as controlled-release with respect to one or more active ingredients therein using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release formulations are designed to initially release an amount of drug that promptly produces the desired therapeutic effect, and gradually and continually release of additional amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, concentration, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing agent, wetting agent, suspending agent, and a preservative. Additional excipients, such as fillers, sweeteners, flavoring, or coloring agents, may also be included in these formulations.

A formulation of a pharmaceutical composition of the invention suitable for oral administration may be prepared or packaged in the form of a discrete solid dose unit including, but not limited to, a tablet, a hard or soft capsule, a cachet, a troche, or a lozenge, each containing a predetermined amount of the active ingredient. In one embodiment, a formulation of a pharmaceutical composition of the invention suitable for oral administration is coated with an enteric coat.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate and poloxamers. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets, optionally, with laser drilling. Tablets may further comprise a sweetener, a flavoring agent, a coloring agent, a preservative, or some combination of these in order to provide for pharmaceutically elegant and palatable formulations.

Hard capsules comprising the active ingredient may be made using a physiologically degradable composition, such as gelatin or HPMC. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, propyl, n-butyl, s-butyl, t-butyl, n-pentyl, s-pentyl, or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, "alkyl linker" is intended to include $C_1$, $C_2$, $C_3$, $C_4$, $C_5$, or $C_6$ straight chain (linear) saturated aliphatic hydrocarbon groups and $C_3$, $C_4$, $C_5$, or $C_6$ branched saturated aliphatic hydrocarbon groups. For example, $C_1$-$C_6$ alkyl linker is intended to include $C_1$, $C_2$, $C_3$, $C_4$, $C_5$, and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—). The term "substituted alkyl linker" refers to alkyl linkers having substituents replacing one or more hydrogen atoms on one or more carbons of the hydrocarbon backbone. Such substituents do not alter the sp3-hybridization of the carbon atom to which they are attached and include those listed below for "substituted alkyl."

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl(benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or two to four carbon atoms.

"Aryl" includes groups with aromaticity, including "conjugated", or multicyclic, systems with at least one aromatic ring. Examples include phenyl, benzyl, naphthyl, etc. "Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the heteroaryl is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

As used herein, "Ph" refers to phenyl, and "Py" refers to pyridinyl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, or indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

The term "acyl", as used herein, includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formulae of the invention (e.g., Formulas I, Ia, Ib, II III, and IV), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

As used herein, a "subject in need thereof" is a subject having a neurological disease. In one embodiment, a subject in need thereof has multiple sclerosis. A "subject" includes a mammal. The mammal can be e.g., any mammal, e.g., a human, primate, bird, mouse, rat, fowl, dog, cat, cow, horse, goat, camel, sheep or a pig. In one embodiment, the mammal is a human.

The present invention provides methods for the synthesis of the compounds of each of the formulae described herein. The present invention also provides detailed methods for the synthesis of various disclosed compounds of the present invention according to the following schemes and as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, polymorph, hydrate, solvate or co-crystal thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry Reactions, Mechanisms, and Structure, $5^{th}$ edition, John Wiley & Sons: New York, 2001; and Greene, T. W., Wuts, P. G. M., Protective Groups in Organic Synthesis, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with each of the formulae described herein may be prepared according to the following procedures from commercially available starting materials or starting materials which can be prepared using literature procedures. These procedures show the preparation of representative compounds of this invention.

EXPERIMENTAL

General Procedure 1

To a mixture of monomethyl fumarate (MMF) (1.0 equivalent) and HBTU (1.5 equivalents) in DMF (25 ml per g of MMF) was added Hünigs base (2.0 equivalents). The dark brown solution was stirred for 10 minutes, where turned into a brown suspension, before addition of the alcohol (1.0-1.5 equivalents). The reaction was stirred for 18 hours at room temperature. Water was added and the product extracted into ethyl acetate three times. The combined organic layers were washed with water three times, dried with magnesium sulphate, filtered and concentrated in vacuo at 45° C. to give the crude product. The crude product was purified by silica chromatography and in some cases further purified by trituration with diethyl ether to give the clean desired ester product. All alcohols were either commercially available or made following known literature procedures.

As an alternative to HBTU (N,N,N',N'-Tetramethyl-O-(1H-benzotriazol-1-yl)uronium hexafluorophosphate), any one of the following coupling reagents can be used: EDCl/HOBt (N-(3-dimethylaminopropyl)-N'-ethylcarbodiimide hydrochloride/hydroxybenzotriazole hydrate); COMU ((1-cyano-2-ethoxy-2-oxoethylidenaminooxy)dimethylamino-morpholino-carbenium hexafluorophosphate); TBTU (O-(benzotriazol-1-yl)-N,N,N',N'-tetramethyluronium tetrafluoroborate); TATU (O-(7-azabenzotriazole-1-yl)-1,1,3,3-tetramethyluronium tetrafluoroborate); Oxyma (ethyl (hydroxyimino)cyanoacetate); PyBOP ((benzotriazol-1-yloxy) tripyrrolidinophosphonium hexafluorophosphate); HOTT (S-(1-oxido-2-pyridyl)-N,N,N',N'-tetramethylthiuronium hexafluorophosphate); FDPP (pentafluorophenyl diphenylphosphinate); T3P (propylphosphonic anhydride); DMTMM (4-(4,6-dimethoxy-1,3,5-triazin-2-yl)-4-methyl-morpholinium tetrafluoroborate); PyOxim ([ethyl cyano(hydroxyimino)acetato-O$^2$]tri-1-pyrrolidinylphosphonium hexafluorophosphate); TSTU (N,N,N',N'-tetramethyl-O—(N-succinimidyl)uronium tetrafluoroborate); TDBTU (O-(3,4-dihydro-4-oxo-1,2,3-benzotriazin-3-yl)-N,N,N',N'-tetramethyluronium tetrafluoroborate); TPTU (O-(2-oxo-1(2H) pyridyl)-N,N,N',N'-tetramethyluronium tetrafluoroborate); TOTU (O-[(ethoxycarbonyl)cyanomethylenamino]-N,N,N', N'-tetramethyluronium tetrafluoroborate); IIDQ (isobutyl 1,2-dihydro-2-isobutoxy-1-quinolinecarboxylate); or Py-CIU (chlorodipyrrolidinocarbenium hexafluorophosphate), As an alternative to Hünig's base (diisopropylethylamine), any one of the following amine bases can be used: triethylamine; tributylamine; triphenylamine; pyridine; lutidine (2,6-dimethylpyridine); collidine (2,4,6-trimethylpyridine); imidazole; DMAP (4-(dimethylamino)pyridine); DABCO (1,4-diazabicyclo[2.2.2]octane); DBU (1,8-diazabicyclo[5.4.0]undec-7-ene); DBN (1,5-diazabicyclo[4.3.0] non-5-ene); or proton Sponge® (N,N,N',N'-tetramethyl-1,8-naphthalenediamine).

General Procedure 2—Conversion of the Ester Product into the Hydrochloride Salt

To a mixture of the ester product in diethyl ether (25 ml per g) was added 2M HCl in diethyl ether (1.5 equivalents). The mixture was stirred at room temperature for two hours. The solvent was decanted, more diethyl ether added and the solvent decanted again. The remaining mixture was then concentrated in vacuo at 45° C. and further dried in a vacuum oven at 55° C. for 18 hours to give the solid HCl salt.

General Procedure 3

To a 100 mL, one-necked, round-bottomed flask, fitted with a magnetic stirrer and nitrogen inlet/outlet, were added 11 mL of an MTBE solution containing freshly prepared monomethyl fumaryl chloride (4.9 g, 33 mmol) and 50 mL of additional MTBE at 20° C. The resulting yellow solution was cooled to <20° C. with an ice water bath. Then, the alcohol, (33 mmol, 1 eq) was added dropwise, via syringe, over approximately 10 minutes. The reaction mixture was allowed to stir at <20° C. for 10 minutes after which time the cooling bath was removed and the reaction was allowed to warm to 20° C. and stir at 20° C. temperature for 16 hours. The reaction was deemed complete by TLC after 16 hours at RT. The reaction mixture was filtered through a medium glass fritted funnel to collect the off-white solids. The solids were dried in a vacuum oven at 25° C. overnight to afford the final product as an HCl salt. All alcohols were either commercially available or made following known literature procedures.

General Procedure 4—Alkylation with an Appropriate Alkyl Mesylate

A mixture of monomethyl fumarate (MMF) (1.3 equivalent), the alkyl mesylate (1 equivalent), and potassium carbonate (1.5 equivalent) in acetonitrile (50 ml per g of MMF) was heated at reflux overnight. The mixture was partitioned between ethyl acetate and saturated aqueous sodium hydrogen carbonate, and the organic phase dried (MgSO$_4$). Filtration and removal of the solvent under reduced pressure gave the crude product which was purified in each case by silica chromatography.

General Procedure 5—Alkylation with an Appropriate Alkyl Chloride

A mixture of monomethyl fumarate (MMF) (1.3 equivalent), the alkyl chloride (1 equivalent), and potassium carbonate (1.5 equivalent) in acetonitrile or dimethylformamide (50 ml per g of MMF) was heated at 20 to 65° C. overnight. The mixture was partitioned between ethyl acetate and saturated aqueous sodium hydrogen carbonate, and the organic phase dried (MgSO$_4$). Filtration and removal of the solvent under reduced pressure gave the crude product which was further purified by silica chromatography.

Chemical Analysis/Procedures

The NMR spectra described herein were obtained with a Varian 400 MHz NMR spectrometer using standard techniques known in the art.

EXAMPLES

Example 1

(E)-2,2'-((2-(4-methoxy-4-oxobut-2-enoyl)oxy) ethyl)azanediyl)diacetic acid hydrochloride (1)

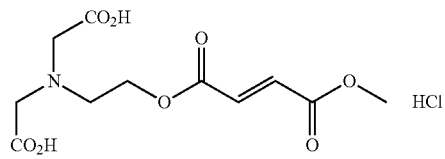 [SMILES: COC(=O)/C=C/C(=O)OCCN(CC(=O)O)CC(=O)O ; Cl]

To a solution of 2-(bis(2-(tert-butoxy)-2-oxoethyl)amino) ethyl methyl fumarate (2.52 g, 6.2 mmol) in dioxane (25 ml) was added 2M HCl in dioxane (30 ml) and the mixture stirred for 90 hours. The precipitate was filtered, washed with diethyl ether and dried in a vacuum oven at 55° C. for 18 hours to give (E)-2,2'-((2-((4-methoxy-4-oxobut-2-enoyl)oxy)ethyl)azanediyl)diacetic acid hydrochloride, a white solid (1.31 g, 65%).

$^1$H NMR (300 MHz, MeOD): δ 6.87 (2H, dd, J=16.1 Hz); 4.46-4.53 (2H, m); 4.09 (4H, s); 3.79 (3H, s); 3.57-3.63 (2H, m). [M+H]$^+$=290.12.

Methyl (2-(methyl(2-(methylsulfonyl)ethyl)amino)ethyl) fumarate hydrochloride (2)

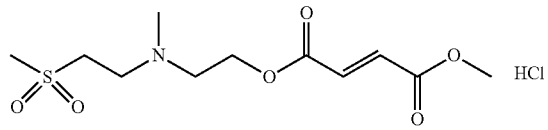

Methyl (2-(N-methylmethylsulfonamido)ethyl) fumarate 2 was synthesized following general procedure 1 and was converted to the HCl salt methyl (2-(methyl(2-(methylsulfonyl)ethyl)amino)ethyl) fumarate hydrochloride (procedure 2) (1.39 g, 95%).

$^1$H NMR (400 MHz, DMSO): δ 11.51 (1H, m); 6.83 (2H, dd, J=15.8 Hz); 4.48 (1H, bs); 3.24-3.90 (7H, m); 3.07 (3H, s); 2.78 (2H, bs). [M+H]$^+$=294.09.

2-(dimethylamino)propyl methyl fumarate hydrochloride (3)

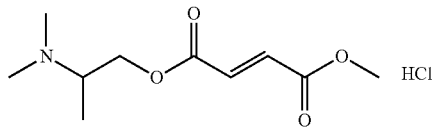

2-(dimethylamino)propyl methyl fumarate 3 was synthesized following general procedure 1 and was converted to the HCl salt: 2-(dimethylamino)propyl methyl fumarate hydrochloride (procedure 2) (329 mg, 92%).

$^1$H NMR (300 MHz, DMSO): δ 10.40 (1H, bs); 6.86 (2H, dd, J=15.8 Hz); 4.25-4.46 (2H, m); 3.71 (3H, s); 3.34 (1H, s); 2.69 (6H, s); 1.24 (3H, s). [M+H]$^+$=216.14.

(E)-2-((4-methoxy-4-oxobut-2-enoyl)oxy)-N,N,N-trimethylethanaminium iodide (4)

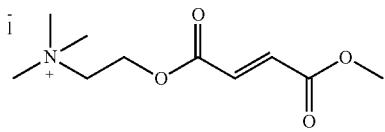

To a solution of 2-(dimethylamino)ethyl methyl fumarate 19 (760 mg, 3.7 mmol) in diethyl ether (20 ml) was added methyl iodide (246 μl, 3.9 mmol). The mixture was stirred at room temperature for 18 hours where a precipitate slowly formed. The mixture was filtered, washed with diethyl ether and dried in a vacuum oven at 55° C. for 18 hours to give (E)-2-((4-methoxy-4-oxobut-2-enoyl)oxy)-N,N,N-trimethylethanaminium iodide, a white solid (1.15 g, 90%).

$^1$H NMR (300 MHz, DMSO): δ 6.80 (2H, dd, J=16.1 Hz); 4.56 (2H, bs); 3.66-3.75 (5H, m); 3.11 (9H, s). [M+H]$^+$=216.14.

2-(4,4-difluoropiperidin-1-yl)ethyl methyl fumarate hydrochloride (5)

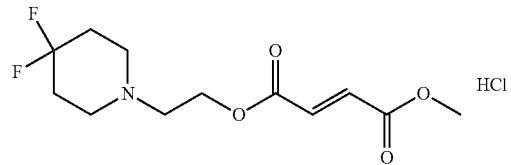 [SMILES: COC(=O)/C=C/C(=O)OCCN1CCC(F)(F)CC1 ; Cl]

2-(4,4-difluoropiperidin-1-yl)ethyl methyl fumarate 5 was synthesized following general procedure 1 and was converted to the HCl salt: 2-(4,4-difluoropiperidin-1-yl)ethyl methyl fumarate hydrochloride (procedure 2) (780 mg, 87%).

$^1$H NMR (300 MHz, DMSO): δ 11.25 (1H, bs); 6.84 (2H, dd, J=16.1 Hz); 4.50 (2H, bs); 3.35-4.00 (8H, m); 3.05-3.30 (2H, m); 2.20-2.45 (3H, s). [M+H]$^+$=278.16.

1-(dimethylamino)propan-2-yl methyl fumarate hydrochloride (6)

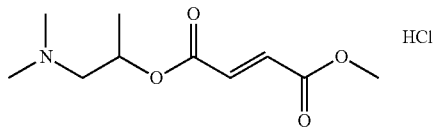

1-(dimethylamino)propan-2-yl methyl fumarate 6 was synthesized following general procedure 1 and was converted to the HCl salt 1-(dimethylamino)propan-2-yl methyl fumarate hydrochloride (procedure 2) (690 mg, 72%).

$^1$H NMR (300 MHz, DMSO): δ 10.41 (1H, bs); 6.80 (2H, dd, J=15.8 Hz); 5.18-5.33 (1H, m); 3.20-3.55 (2H, m); 3.72 (3H, s); 2.60-2.80 (7H, m); 1.18-1.28 (3H, m). [M+H]$^+$=216.14.

Methyl (2-thiomorpholinoethyl) fumarate hydrochloride (7)

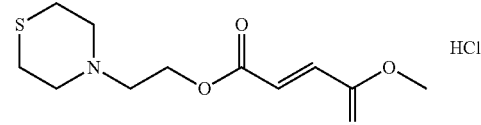

Methyl (2-thiomorpholinoethyl) fumarate 7 was synthesized following general procedure 1 and was converted to the HCl salt, methyl (2-thiomorpholinoethyl) fumarate hydrochloride (procedure 2) (623 mg, 93%).

$^1$H NMR (300 MHz, DMSO): δ 11.03 (1H, bs); 6.83 (2H, dd, J=15.6 Hz); 4.50 (2H, s); 3.00-3.80 (11H, m); 2.70-2.80 (2H, m). [M+H]$^+$=216.14. [M+H]$^+$=260.11.

Methyl (2-(phenylamino)ethyl) fumarate hydrochloride (8)

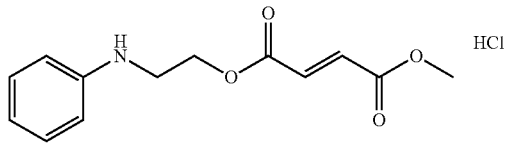 [SMILES: COC(=O)/C=C/C(=O)OCCNc1ccccc1 ; Cl]

Methyl (2-(phenylamino)ethyl) fumarate 8 was synthesized following general procedure 1 and was converted to the HCl salt methyl (2-(phenylamino)ethyl) fumarate hydrochloride (procedure 2) (1.80 g, quantitative).

$^1$H NMR (300 MHz, DMSO): δ 6.50-6.80 (9H, m); 4.29 (2H, t, 4.4 Hz); 3.72 (3H, s); 3.45 (2H, t, J=4.5 Hz). [M+H]$^+$=250.13.

2-(dimethylamino)-2-methylpropyl methyl fumarate hydrochloride (9)

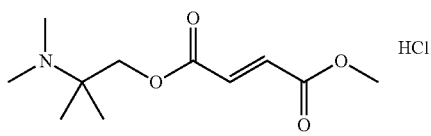

2-(dimethylamino)-2-methylpropyl methyl fumarate 9 was synthesized following general procedure 1 and was converted to the HCl salt, 2-(dimethylamino)-2-methylpropyl methyl fumarate hydrochloride (procedure 2) (883 mg, 76%).

$^1$H NMR (300 MHz, DMSO): δ 10.20 (1H, bs); 6.91 (2H, dd, J=15.6 Hz); 4.29 (2H, s); 3.73 (3H, s); 2.57-2.80 (6H, m); 1.32 (6H, s). [M+H]$^+$=230.16.

Methyl (2-(methylsulfonyl)ethyl) fumarate (10)

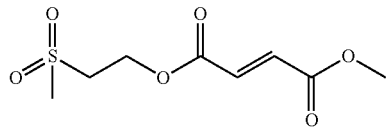

Methyl (2-(methylsulfonyl)ethyl) fumarate 10 was synthesized following general procedure 1 and (1.01 g, 37%).

$^1$H NMR (400 MHz, CDCl$_3$): δ 6.88 (2H, dd, J=16.0 Hz); 4.66 (2H, t, J=5.8 Hz); 3.82 (3H, s); 3.38 (2H, t, J=6.0 Hz); 2.99 (3H, s). [M+H]$^+$=236.97.

2-(1,1-dioxidothiomorpholino)ethyl methyl fumarate hydrochloride (11)

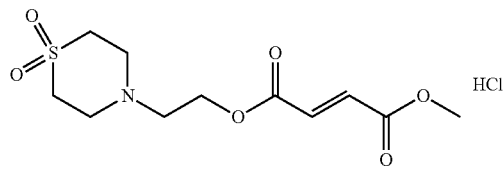 [SMILES: COC(=O)/C=C/C(=O)OCCN1CCS(=O)(=O)CC1 ; Cl]

2-(1,1-dioxidothiomorpholino)ethyl methyl fumarate 11 was synthesized following general procedure 1 and was converted to the HCl salt 2-(1,1-dioxidothiomorpholino) ethyl methyl fumarate hydrochloride (procedure 2) (1.33 g, 87%).

$^1$H NMR (400 MHz, DMSO): δ 6.79 (2H, dd, J=15.8 Hz); 4.34 (2H, bs); 3.72 (4H, s); 2.90-3.70 (11H, m). [M+H]$^+$=292.11.

Methyl (2-(methyl(phenyl)amino)ethyl) fumarate hydrochloride (12)

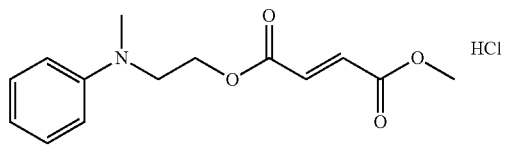 [SMILES: COC(=O)/C=C/C(=O)OCCN(C)c1ccccc1 ; Cl]

Methyl (2-(methyl(phenyl)amino)ethyl) fumarate 12 was synthesized following general procedure 1 and was converted to the HCl salt methyl (2-(methyl(phenyl)amino) ethyl) fumarate hydrochloride (procedure 2) (1.76 g, 97%).

$^1$H NMR (400 MHz, DMSO): δ 6.72-7.40 (5H, m); 6.64 (2H, dd, J=16.0 Hz); 4.27 (2H, s); 3.70 (5H, s); 2.97 (3H, s). [M+H]$^+$=264.14.

2-(benzyl(methyl)amino)ethyl methyl fumarate hydrochloride (13)

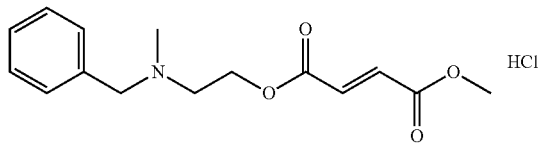 [SMILES: COC(=O)/C=C/C(=O)OCCN(C)Cc1ccccc1 ; Cl]

2-(benzyl(methyl)amino)ethyl methyl fumarate 13 was synthesized following general procedure 1 and was converted to the HCl salt 2-(benzyl(methyl)amino)ethyl methyl fumarate hydrochloride (procedure 2) (2.70 g, 96%).

$^1$H NMR (400 MHz, DMSO): δ 10.65 (1H, bs); 7.39-7.60 (5H, m); 6.82 (2H, dd, J=15.8 Hz); 4.20-4.60 (4H, m); 3.73 (3H, s); 3.27-3.50 (2H, m); 2.69 (3H, s). [M+H]$^+$=278.16.

2-(2,5-dioxopyrrolidin-1-yl)ethyl methyl fumarate (14)

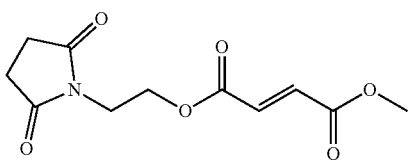 [SMILES: COC(=O)/C=C/C(=O)OCCN1C(=O)CCC1=O]

2-(2,5-dioxopyrrolidin-1-yl)ethyl methyl fumarate 14 was synthesized following general procedure 1 (1.03 g, 35%).

$^1$H NMR (400 MHz, DMSO): δ 6.81 (2H, dd, J=15.8 Hz); 4.36 (2H, t, J=5.3 Hz); 3.84 (2H, t, J=5.1 Hz); 3.80 (3H, s); 2.73 (4H, s). [M+H]$^+$=256.07.

Methyl (2-(piperidin-1-yl)ethyl) fumarate hydrochloride (15)

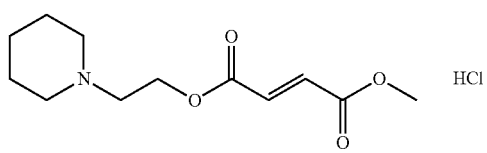 [SMILES: COC(=O)/C=C/C(=O)OCCN1CCCCC1 ; Cl]

Methyl (2-(piperidin-1-yl)ethyl) fumarate hydrochloride 15 was synthesized following general procedure 3.

$^1$H NMR (400 MHz, DMSO-d6) δ 10.76 (s, 1H), 6.94-6.77 (m, 2H), 4.58-4.51 (m, 2H), 3.76 (s, 3H), 3.48-3.36 (m, 4H), 2.94 (dddd, J=15.9, 12.1, 9.2, 4.4 Hz, 2H), 1.91-1.64 (m, 5H), 1.37 (dtt, J=16.4, 11.3, 4.9 Hz, 1H). [M+H]$^+$=241.93.

Methyl (2-morpholinoethyl) fumarate hydrochloride (16)

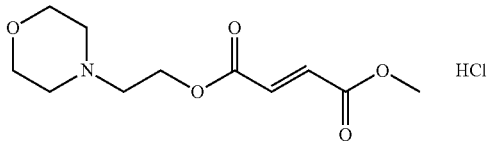 [SMILES: COC(=O)/C=C/C(=O)OCCN1CCOCC1 ; Cl]

Methyl (2-morpholinoethyl) fumarate hydrochloride 16 was synthesized following general procedure 3.

$^1$H 1H NMR (400 MHz, DMSO-d6) δ 11.36 (s, 1H), 6.92 (d, J=15.9 Hz, 1H), 6.82 (d, J=15.9 Hz, 1H), 4.60-4.52 (m, 2H), 4.00-3.77 (m, 6H), 3.76 (s, 3H), 3.22-3.04 (m, 4H). [M+H]$^+$=244.00.

2-(1,4-dioxa-8-azaspiro[4.5]decan-8-yl)ethyl methyl fumarate hydrochloride (17)

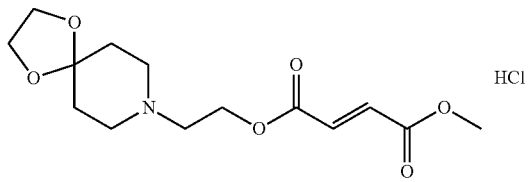 [SMILES: COC(=O)/C=C/C(=O)OCCN1CCC2(CC1)OCCO2 ; Cl]

2-(1,4-dioxa-8-azaspiro[4.5]decan-8-yl)ethyl methyl fumarate hydrochloride 17 was synthesized following general procedure 3.

$^1$H NMR (400 MHz, DMSO-d6) δ 11.26 (s, 1H), 6.91 (d, J=15.9 Hz, 1H), 6.82 (d, J=15.9 Hz, 1H), 4.58-4.51 (m, 2H), 3.93 (s, 4H), 3.76 (s, 3H), 3.57-3.43 (m, 4H), 3.22-3.03 (m, 2H), 2.20-2.02 (m, 2H), 1.89-1.79 (m, 2H). [M+H]$^+$=300.00.

Methyl (2-(pyrrolidin-1-yl)ethyl) fumarate hydrochloride (18)

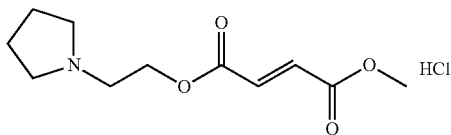 [SMILES: COC(=O)/C=C/C(=O)OCCN1CCCC1 ; Cl]

Methyl (2-(pyrrolidin-1-yl)ethyl) fumarate hydrochloride 18 was synthesized following general procedure 3.

$^1$H NMR (400 MHz, DMSO-d6) δ 11.12 (s, 1H), 6.94 (d, J=15.8 Hz, 1H), 6.82 (d, J=15.8 Hz, 1H), 4.53-4.46 (m, 2H), 3.76 (s, 3H), 3.61-3.45 (m, 4H), 3.11-2.94 (m, 2H), 2.06-1.79 (m, 4H). [M+H]$^+$=228.46.

2-(dimethylamino)ethyl methyl fumarate hydrochloride (19)

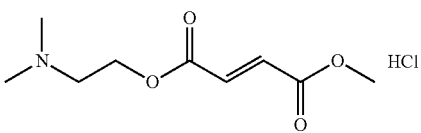

2-(dimethylamino)ethyl methyl fumarate hydrochloride 19 was synthesized following general procedure 3.

$^1$H NMR (500 MHz, DMSO-d6) δ 10.87 (s, 1H), 6.93 (d, J=15.9 Hz, 1H), 6.80 (d, J=15.9 Hz, 1H), 4.53-4.45 (m, 2H), 3.75 (s, 3H), 3.44-3.38 (m, 2H), 2.77 (s, 5H). [M+H]$^+$=201.84.

2-(diethylamino)ethyl methyl fumarate hydrochloride (20)

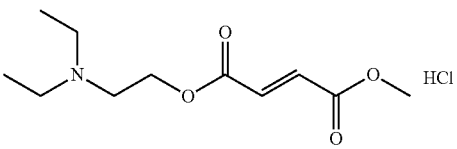 [SMILES: CCN(CC)CCOC(=O)/C=C/C(=O)OC ; Cl]

2-(diethylamino)ethyl methyl fumarate hydrochloride 20 was synthesized following general procedure 3.

$^1$H NMR (400 MHz, DMSO-d6) δ 10.85 (s, 1H), 6.90 (d, J=15.8 Hz, 1H), 6.81 (d, J=15.9 Hz, 1H), 4.56-4.48 (m, 2H), 3.76 (s, 3H), 3.48-3.38 (m, 2H), 3.15 (qq, J=9.7, 5.5, 4.9 Hz, 4H), 1.24 (t, J=7.3 Hz, 6H). [M+H]$^+$=230.59.

2-(3,3-difluoropyrrolidin-1-yl)ethyl methyl fumarate hydrochloride (21)

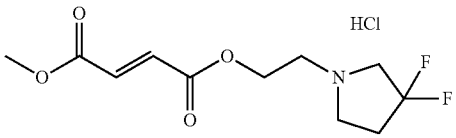 [SMILES: COC(=O)/C=C/C(=O)OCCN1CCC(F)(F)C1 ; Cl]

2-(3,3-Difluoropyrrolidin-1-yl)ethyl methyl fumarate 21 was synthesised from 2-(3,3-difluoropyrrolidin-1-yl)ethanol following general procedure 1.

2-(3,3-difluoropyrrolidin-1-yl)ethyl methyl fumarate was converted to 2-(3,3-difluoropyrrolidin-1-yl)ethyl methyl fumarate hydrochloride following general procedure 2 (0.55 g, 69%).

$^1$H NMR (300 MHz, DMSO); δ 6.79 (2H, d); 4.20-4.39 (2H, m), 3.81 (2H, t), 3.66 (3H, s), 3.53-3.65 (4H, m), 2.54 (2H, sep). m/z [M+H]$^+$=264.14.

2-(bis(2-methoxyethyl)amino)ethyl methyl fumarate hydrochloride (24)

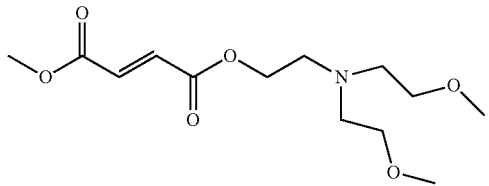

2-(Bis(2-methoxyethyl)amino)ethyl methyl fumarate 24 was synthesised from 2-(bis(2-methoxyethyl)amino)ethanol following general procedure 1. 2-(Bis(2-methoxyethyl)amino)ethyl methyl fumarate was converted to 2-(bis(2-methoxyethyl)amino)ethyl methyl fumarate hydrochloride following general procedure 2 (1.00 g, 27%).

$^1$H NMR (300 MHz, DMSO); δ 12.84 (1H, br s), 6.90 (2H, d), 4.73 (2H, t), 3.92 (4H, t), 3.81 (3H, s), 3.62 (2H, br s), 3.51-3.36 (4H, m), 3.34 (6H, s). m/z [M+H]$^+$=290.12.

2-(2,4-Dioxo-3-azabicyclo[3.1.0]hexan-3-yl)ethyl methyl fumarate (22)

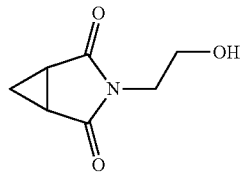 [SMILES: O=C1C2CC2C(=O)N1CCO]

3-oxabicyclo[3.1.0]hexane-2,4-dione (1.0 g, 8.9 mmol) and ethanolamine (545 mg, 8.9 mmol) were heated neat at 200° C. for 2 hours. The crude reaction mixture was purified by silica chromatography (EtOAc) giving 3-(2-Hydroxyethyl)-3-azabicyclo[3.1.0]hexane-2,4-dione (1.06 g, 77%).

$^1$H NMR (300 MHz, CDCl$_3$): δ 3.71 (2H, t), 3.56 (2H, t), 2.51 (2H, dd), 1.95 (1H, br s), 1.59-1.43 (2H, m).

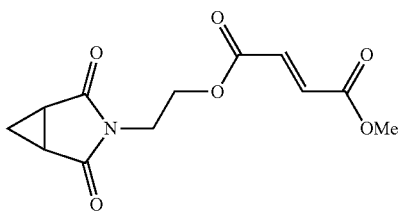 [SMILES: COC(=O)/C=C/C(=O)OCCN1C(=O)C2CC2C1=O]

2-(2,4-dioxo-3-azabicyclo[3.1.0]hexan-3-yl)ethyl methyl fumarate 22 was synthesised from 3-(2-Hydroxyethyl)-3-azabicyclo[3.1.0]hexane-2,4-dione following general procedure 1 (452 mg, 53%).

$^1$H NMR (300 MHz, CDCl$_3$): δ 6.81 (2H, d), 4.28 (2H, t), 3.80 (3H, s), 3.69 (2H, t), 2.48 (2H, dd), 1.59-1.49 (1H, m), 1.44-1.38 (1H, m). m/z [M+H]$^+$=268.11.

2-(2,2-Dimethyl-5-oxopyrrolidin-1-yl)ethyl methyl fumarate (24)

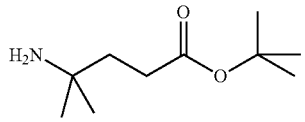

Tert-butyl acrylate (19.7 mL, 134.8 mmol) was added dropwise over 10 minutes to a refluxing solution of 2-nitropropane and Triton B (40% in methanol) (440 µL) in ethanol (50 mL). The reaction was heated at reflux overnight. The reaction solvent was removed under reduced pressure giving a crude residue that was dissolved in ethanol (200 mL) and hydrogenated overnight (300 psi) using Raney nickel (approximately 15 g). The reaction was filtered through celite. The solvent was removed under reduced pressure giving tert-butyl 4-amino-4-methylpentanoate (15.82 g, 63% yield).

$^1$H NMR (300 MHz, CDCl$_3$): δ 2.26 (2H, t), 1.65 (2H, t), 1.43 (9H, s), 1.68 (6H, s).

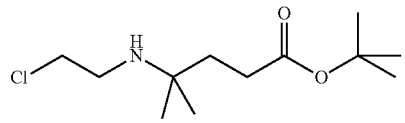 [SMILES: CC(C)(CCC(=O)OC(C)(C)C)NCCCl]

To a solution of tert-butyl 4-amino-4-methylpentanoate (3.0 g, 16.04 mmol) in methanol (100 mL) was added chloroacetaldehyde (45% in H$_2$O) (6.7 mL, 38.4 mmol) followed by acetic acid (2 mL, 35.0 mmol). After 1.5 hours sodium cyanoborohydride (1.51 g, 24.0 mmol) was added and the mixture stirred at room temperature for 3 hours. The reaction was partitioned between saturated aqueous sodium hydrogen carbonate (100 mL) and dichloromethane (300 mL). The organic phase was dried (MgSO$_4$). Filtration and removal of the solvent under reduced pressure gave tert-butyl 4-((2-chloroethyl)amino)-4-methylpentanoate (3.90 g, 98% yield).

$^1$H NMR (300 MHz, CDCl$_3$): δ 3.63 (2H, t), 2.85 (2H, t), 2.24 (2H, t), 1.67 (2H, t), 1.44 (9H, s), 1.07 (6H, s).

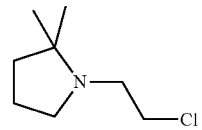

A mixture of tert-butyl 4-((2-chloroethyl)amino)-4-methylpentanoate (3.9 g, 15.7 mmol) and trifluoroacetic acid (27 mL) in dichloromethane (80 mL) were stirred at room temperature overnight. The reaction mixture was concentrated under reduced pressure. The residue was dissolved in further dichloromethane and concentrated again. This was repeated a further 3 times until the majority of the excess trifluoroacetic acid had been removed. The residue was dissolved in dichloromethane (500 mL) and N-(3-Dimethylaminopropyl)-N'-ethylcarbodiimide hydrochloride (4.61 g, 24.1 mmol), hydroxybenzotriazole hydrate (3.25 g, 24.1 mmol) and diisopropylethylamine (21 mL, 120 mmol) added. The mixture was stirred at room temperature overnight. The reaction was washed with water (300 mL) and dried (MgSO$_4$). Filtration and removal of the solvent under reduced pressure gave a crude residue that was purified by silica chromatography (heptane to ethyl acetate) giving 1-(2-chloroethyl)-5,5-dimethylpyrrolidin-2-one (1.24 g, 44% yield).

$^1$H NMR (300 MHz, CDCl$_3$): δ 3.61 (2H, t), 3.41 (2H, t), 2.38 (2H, t), 1.88 (2H, t), 1.24 (6H, s).

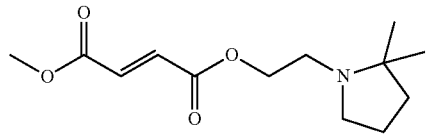

2-(2,2-Dimethyl-5-oxopyrrolidin-1-yl)ethyl methyl fumarate 24 was synthesised from 1-(2-chloroethyl)-5,5-dimethylpyrrolidin-2-one following general procedure 5 (1.02 g, 41%).

$^1$H NMR (300 MHz, CDCl$_3$); 6.85 (2H, d), 4.33 (2H, t), 3.80 (3H, s), 3.41 (2H, t), 2.39 (2H, t), 1.88 (2H, t), 1.23 (6H, s). m/z [M+H]$^+$=270.17.

(E)-4-(2-((4-methoxy-4-oxobut-2-enoyl)oxy)ethyl)morpholine 4-oxide (26)

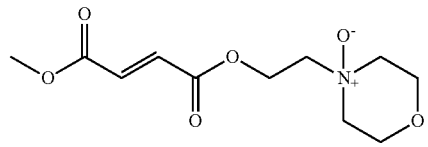 [SMILES: COC(=O)/C=C/C(=O)OCC[N+]1([O-])CCOCC1]

To a solution of methyl (2-morpholinoethyl) fumarate (1.1 g, 4.5 mmol) [synthesised from 4-(2-chloroethyl)morpholine following general procedure 5] in dichloromethane was added m-chloroperbenzoic acid (1.87 g, 5.4 mmol) and the reaction mixture stirred for 1 h. The reaction mixture was diluted with water (25 mL) and washed with dichloromethane (3×50 mL). The aqueous phase was lyophilized giving (E)-4-(2-((4-methoxy-4-oxobut-2-enoyl)oxy)ethyl)morpholine 4-oxide 26 (0.19 g, 16%).

$^1$H NMR (300 MHz, CDCl$_3$); 6.87 (1H, d), 6.81 (1H, d), 4.92-4.88 (2H, M), 4.44 (2H, t), 3.78-3.73 (2H, m), 3.54-3.48 (2H, m), 3.34 (2H, t), 3.15 (2H, d). m/z [M+H]$^+$=260.2.

2-(3,5-dioxomorpholino)ethyl methyl fumarate (27)

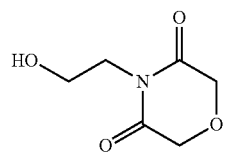 [SMILES: O=C1COCC(=O)N1CCO]

To a solution of diglycolic anhydride (2.0 g, 17 mmol) in pyridine (10 mL) was added ethanolamine (2.1 g, 34 mmol) and heated at reflux for 2 h. The volatiles were removed in vacuo and the residue heated at 180° C. for 2 h and then 220° C. for 90 min. The reaction mixture was cooled and the residue purified on silica eluting with dichloromethane/ethyl acetate (4:1) giving 4-(2-hydroxyethyl)morpholine-3,5-dione (1.05 g, 38%).

$^1$H NMR (300 MHz, CDCl$_3$); 4.39 (4H, s), 4.02 (2H, t), 3.80 (2H, t).

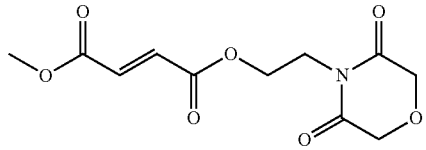 [SMILES: COC(=O)/C=C/C(=O)OCCN1C(=O)COCC1=O]

2-(3,5-dioxomorpholino)ethyl methyl fumarate 27 was synthesised from 4-(2-hydroxyethyl)morpholine-3,5-dione following general procedure 1 (0.82 g, 96%).

$^1$H NMR (300 MHz, CDCl$_3$); 6.83 (1H, d), 6.75 (1H, d), 4.39-4.43 (6H, m), 4.12 (2H, t), 3.79 (3H, s).

2-(2,2-dimethylmorpholino)ethyl methyl fumarate hydrochloride (28)

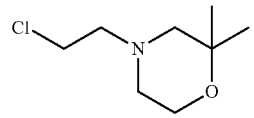

To a solution of 2,2-dimethylmorpholine (1.0 g, 8.7 mmol) in dichloromethane (35 mL) was added chloroacetaldehyde (50% in water, 1.65 mL, 13.0 mmol), followed by sodium triacetoxyborohydride (2.8 g, 13.0 mmol). The reaction mixture was stirred for 90 min, diluted with 1 M aqueous sodium hydroxide (40 mL) and the organic phase separated. The aqueous phase was extracted with dichloromethane (2×30 mL) and the organic phases combined. After being dried over MgSO$_4$ the volatiles were removed in vacuo giving 4-(2-chloroethyl)-2,2-dimethylmorpholine (1.45 g, 94%).

$^1$H NMR (300 MHz, CDCl$_3$); 3.73 (2H, dd), 3.55 (2H, t), 2.64 (2H, t), 2.43 (2H, dd), 2.25 (2H, s), 1.24 (6H, s).

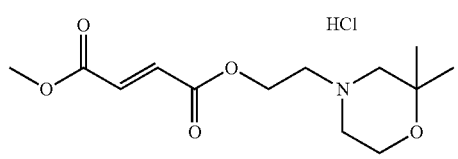

2-(2,2-Dimethylmorpholino)ethyl methyl fumarate 28 was synthesised from 4-(2-chloroethyl)-2,2-dimethylmorpholine following general procedure 5 (0.71 g, 93%). 4-(2-chloroethyl)-2,2-dimethylmorpholine was converted to 4-(2-chloroethyl)-2,2-dimethylmorpholine hydrochloride following general procedure 2 (0.69 g, 87%).

$^1$H NMR (300 MHz, CDCl$_3$); 6.85 (1H, d), 6.77 (1H, d), 4.52-4.47 (2H, m), 3.93-3.85 (2H, m), 3.70 (3H, s), 3.48-3.43 (2H, m), 3.32-3.00 (4H, m), 1.24 (6H, s). m/z [M+H]$^+$= 272.2.

2-(2,6-dimethylmorpholino)ethyl methyl fumarate hydrochloride (29)

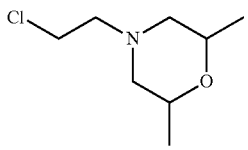

To a solution of 2,6-dimethylmorpholine (1.0 g, 9.0 mmol) in dichloromethane (40 mL) was added chloroacetaldehyde (50% in water, 1.02 mL, 13.5 mmol) and acetic acid (0.75 mL, 13.5 mmol) followed by sodium triacetoxyborohydride (2.8 g, 13.5 mmol). The reaction mixture was stirred for 4 h, diluted with dichloromethane (20 mL) and washed with saturated aqueous sodium hydrogen carbonate (30 mL). The organic phase separated, dried over MgSO$_4$ the volatiles were removed in vacuo. The residue was further purified by silica chromatography eluting with heptanes/ethyl acetate (1:1) giving 4-(2-chloroethyl)-2,6-dimethylmorpholine (0.44 g, 30%).

$^1$H NMR (300 MHz, CDCl$_3$); 3.75-3.62 (2H, m), 3.58 (2H, t), 2.65-2.79 (4H, m), 1.83 (2H, t), 1.15 (6H, d).

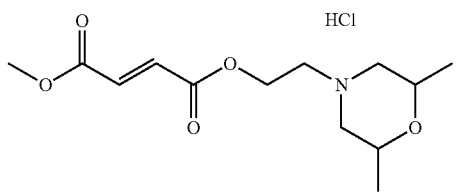

2-(2,6-dimethylmorpholino)ethyl methyl fumarate 29 was synthesised from 4-(2-chloroethyl)-2,6-dimethylmorpholine following general procedure 5 (0.54 g, 71%). 2-(2,6-dimethylmorpholino)ethyl methyl fumarate was converted to 2-(2,6-dimethylmorpholino)ethyl methyl fumarate hydrochloride following general procedure 2 (0.19 g, 64%).

$^1$H NMR (300 MHz, CDCl$_3$); 6.83 (1H, d), 6.75 (1H, d), 4.47-4.43 (2H, m), 3.93-3.82 (2H, m), 3.67 (3H, s), 3.46-3.40 (2H, m), 2.72 (2H, t), 1.10 (6H, d). m/z [M+H]$^+$=272.2

Methyl (2-(3-oxomorpholino)ethyl) fumarate (30)

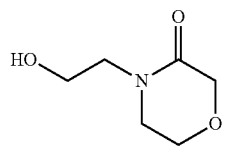

A mixture of potassium tert-butoxide (5.9 g, 52.3 mmol) and toluene (50 mL) was heated at 75° C. for 30 min and then diethanolamine (5.0 g, 47.6 mmol) added. The reaction mixture was heated a further 30 min and then methyl chloroacetate (4.4 mL, 50.0 mmol) added. After a further 2 h heating the reaction was diluted with methanol (21 mL) and cooled to room temperature. The reaction mixture was filtered, washed with toluene and the mother liquor evaporated. The residue was further purified by silica flash column chromatography giving 4-(2-hydroxyethyl)morpholin-3-one (0.65 g, 9%).

$^1$H NMR (300 MHz, CDCl$_3$); 4.19 (2H, s), 3.89 (2H, t), 3.81 (2H, t), 3.57 (2H, t), 3.48 (2H, t), 2.89 (1H, s).

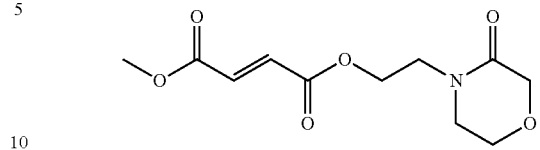

Methyl (2-(3-oxomorpholino)ethyl) fumarate 30 was synthesised from 4-(2-hydroxyethyl)morpholin-3-one following general procedure 1 (0.71 g, 62%).

$^1$H NMR (300 MHz, DMSO); 6.72 (2H, s), 4.28 (2H, t), 3.98 (2H, s), 3.77 (2H, t), 3.71 (3H, t), 3.59 (2H, t), 3.38 (2H, t). m/z [M+H]$^+$=258.1.

Methyl (2-(2-oxomorpholino)ethyl) fumarate hydrochloride (31)

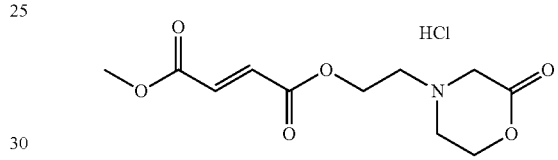

Methyl (2-(2-oxomorpholino)ethyl) fumarate 31 was synthesised from 4-(2-hydroxyethyl)morpholin-2-one following general procedure 1 (0.53 g, 34%). Methyl (2-(2-oxomorpholino)ethyl) fumarate was converted to methyl (2-(2-oxomorpholino)ethyl) fumarate hydrochloride following general procedure 2 (0.20 g, 34%).

$^1$H NMR (300 MHz, DMSO); 3.75 (2H, s), 4.29-4.23 (4H, m), 3.71 (3H, s), 3.34 (2H, s), 2.73 (2H, t), 2.68 (2H, t). m/z [M+H]$^+$=258.15.

2-(8-Oxa-3-azabicyclo[3.2.1]octan-3-yl)ethyl methyl fumarate hydrochloride (32)

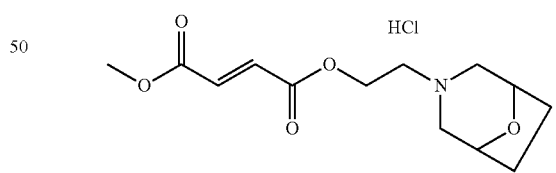

2-(8-Oxa-3-azabicyclo[3.2.1]octan-3-yl) methyl fumarate 32 was synthesised from 3-(2-chloroethyl)-8-oxa-3-azabicyclo[3.2.1]octane following general procedure 5 (0.25 g, 50%). 2-(8-Oxa-3-azabicyclo[3.2.1]octan-3-yl) ethyl methyl fumarate was converted to 2-(8-oxa-3-azabicyclo[3.2.1]octan-3-yl)ethyl methyl fumarate hydrochloride following general procedure 2 (0.20 g, 73%).

$^1$H NMR (300 MHz, D$_2$O); 6.82 (1H, d), 6.75 (1H, d), 4.52-4.42 (4H, m), 3.69 (3H, s), 3.45-3.37 (4H, m), 3.26-3.19 (2H, m), 2.10-1.85 (4H, m). m/z [M+H]$^+$=270.0.

2-(2-((Dimethylamino)methyl)morpholino)ethyl methyl fumarate hydrochloride (33)

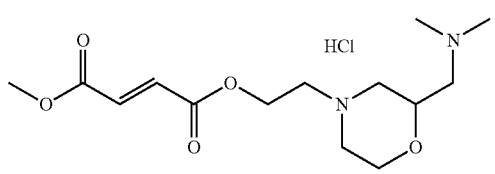

2-(2-((Dimethylamino)methyl)morpholino)ethyl methyl fumarate 33 was synthesised from 1-(4-(2-chloroethyl)morpholin-2-yl)-N,N-dimethylmethanamine following general procedure 5 (0.17 g, 16%).

2-(2-((Dimethylamino)methyl)morpholino)ethyl methyl fumarate was converted to 2-(2-((Dimethylamino)methyl)morpholino)ethyl methyl fumarate hydrochloride following general procedure 2 (0.17 g, 95%).

$^1$H NMR (300 MHz, D$_2$O); 6.84 (1H, d), 6.77 (1H, d), 4.50-4.45 (2H, m), 4.21-4.06 (2H, m), 3.87-3.77 (1H, m), 3.68 (3H, s), 3.56-3.47 (2H, m), 3.25-3.09 (3H, m), 2.94 (1H, dd), 2.81 (6H, bs). m/z [M+H]$^+$=301.2

2-((3S,5S)-3,5-Dimethylmorpholino)ethyl methyl fumarate hydrochloride (34)

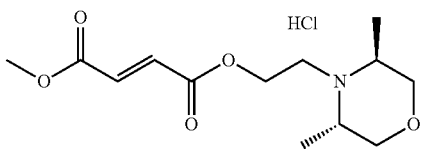 [SMILES: COC(=O)/C=C/C(=O)OCCN1[C@@H](C)COC[C@@H]1C ; Cl]

2-((3S,5S)-3,5-Dimethylmorpholino)ethyl methyl fumarate 34 was synthesised from (3S,5S)-4-(2-chloroethyl)-3,5-dimethylmorpholine following general procedure 5 (0.11 g, 25%). 2-((3S,5S)-3,5-Dimethylmorpholino)ethyl methyl fumarate was converted to 2-((3S,5S)-3,5-dimethylmorpholino)ethyl methyl fumarate hydrochloride following general procedure 2 (0.08 g, 68%).

$^1$H NMR (300 MHz, D$_2$O); 7.15-7.00 (2H, m), 4.77-4.70 (2H, m), 4.20-4.08 (2H, m), 4.01-3.85 (8H, m), 3.68-3.58 (1H, m). m/z [M+H]$^+$=272.3

2-(2,5-Dioxomorpholino)ethyl methyl fumarate (35)

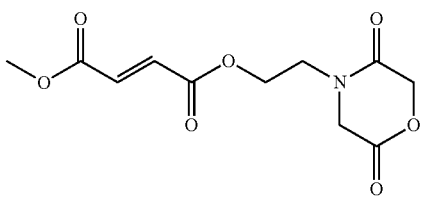 [SMILES: COC(=O)/C=C/C(=O)OCCN1CC(=O)OCC1=O]

2-(2,5-Dioxomorpholino)ethyl methyl fumarate 35 was synthesised from 4-(2-hydroxyethyl)morpholine-2,5-dione following general procedure 1 (0.27 g, 65%). $^1$H NMR (300 MHz, DMSO); 6.75 (1H, d), 6.71 (1H, d), 4.72 (2H, s), 4.30 (2H, s), 4.26 (2H, t), 3.72 (3H, s), 3.60 (2H, t). m/z [M+H]$^+$=272.2.

(E)-Methyl 3-(4-methyl-2,5,7-trioxabicyclo[2.2.2]octan-1-yl)acrylate (130)

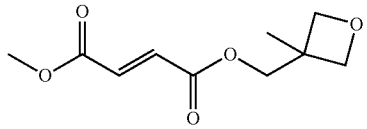

Methyl ((3-methyloxetan-3-yl)methyl) fumarate was synthesised from 3-methyl-3oxetane methanol following general procedure 1 (0.86 g, 89%).

$^1$H NMR (300 MHz, CDCl$_3$); 6.88 (2H, s), 4.52 (2H, d), 4.40 (2H, d), 4.30 (2H, s), 3.82 (3H, s), 1.35 (3H, s).

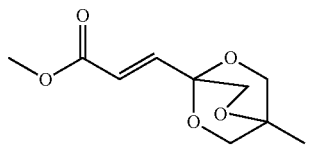

To a solution of methyl ((3-methyloxetan-3-yl)methyl) fumarate 130 (0.20 g, 0.93 mmol) in dichloromethane (5 mL) at 5° C. was added borontrifluoride diethyletherate (0.058 mL, 0.47 mmol). After 1 h a further portion of borontrifluoride diethyletherate (0.058 mL, 0.47 mmol) was added and the reaction mixture warmed to 20° C. over 1 h. To the reaction mixture was added triethylamine (0.13 mL, 0.93 mmol) and then this was loaded directly onto a silica column. The desired product was eluted with heptane/ethyl acetate (6:4) containing triethylamine (2.5% v/v) giving (E)-methyl 3-(4-methyl-2,5,7-trioxabicyclo[2.2.2]octan-1-yl)acrylate (0.12 g, 60%).

$^1$H NMR (300 MHz, CDCl$_3$); 6.66 (1H, d), 6.25 (1H, d), 3.97 (6H, s), 3.73 (3H, s), 0.84 (3H, s). m/z [M+H]$^+$=215.2.

Methyl prop-2-yn-1-yl fumarate (131)

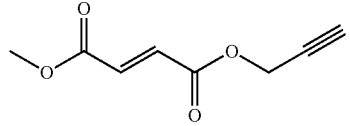

Methyl prop-2-yn-1-yl fumarate 131 was synthesized from propargyl alcohol following general procedure 1 (0.51 g, 68%).

$^1$H NMR (300 MHz, DMSO); 6.85-6.70 (2H, m), 4.81 (2H, d), 3.72 (3H, s), 3.60 (1H, t).

2-(1,3-Dioxoisoindolin-2-yl)ethyl methyl fumarate (36)

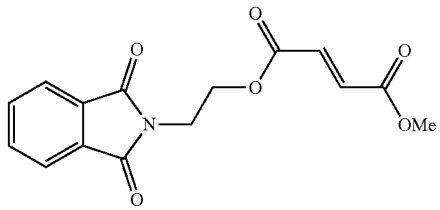 [SMILES: COC(=O)/C=C/C(=O)OCCN1C(=O)c2ccccc2C1=O]

2-(1,3-Dioxoisoindolin-2-yl)ethyl methyl fumarate 36 was synthesised from 2-(2-hydroxyethyl)isoindoline-1,3-dione following general procedure 1 (0.63 g, 79%).

$^1$H NMR (300 MHz, MeOD); 7.87-7.77 (4H, m), 6.74-6.73 (2H, m), 4.45-4.40 (2H, m), 4.01-3.96 (2H, m), 3.76 (3H, s). m/z [M+H]$^+$=304.1.

4-(2,5-Dioxopyrrolidin-1-yl)butyl methyl fumarate (132)

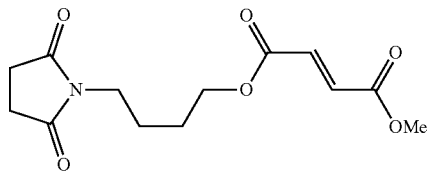 [SMILES: COC(=O)/C=C/C(=O)OCCCCN1C(=O)CCC1=O]

4-(2,5-Dioxopyrrolidin-1-yl)butyl methyl fumarate 132 was synthesised from 1-(4-hydroxybutyl)pyrrolidine-2,5-dione following general procedure 1 (0.77 g, 79%).

$^1$H NMR (300 MHz, MeOD); 6.81-6.79 (2H, m), 4.20 (2H, t), 3.78 (3H, s), 3.50 (2H, t), 2.67 (4H, s), 1.71-1.62 (4H, m). m/z [M+H]$^+$=284.2.

2-(3,3-Dimethyl-2,5-dioxopyrrolidin-1-yl)ethyl methyl fumarate (36)

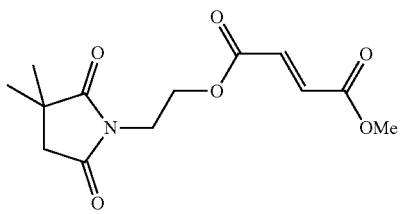 [SMILES: COC(=O)/C=C/C(=O)OCCN1C(=O)CC(C)(C)C1=O]

2-(3,3-Dimethyl-2,5-dioxopyrrolidin-1-yl)ethyl methyl fumarate 36 was synthesised from 1-(2-hydroxyethyl)-3,3-dimethylpyrrolidine-2,5-dione following general procedure 1 (0.72 g, 74%).

$^1$H NMR (300 MHz, CDCl$_3$); 6.83 (1H, d), 6.77 (1H, d), 4.38 (2H, t), 3.82 (1H, t), 3.80 (3H, s), 2.55 (2H, s), 1.31 (6H, s). m/z [M+H]$^+$=284.1.

3-(2,5-Dioxopyrrolidin-1-yl)propyl methyl fumarate (133)

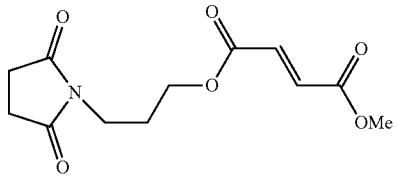 [SMILES: COC(=O)/C=C/C(=O)OCCCN1C(=O)CCC1=O]

3-(2,5-Dioxopyrrolidin-1-yl)propyl methyl fumarate 133 was synthesised from 1-(3-hydroxypropyl)pyrrolidine-2,5-dione following general procedure 1 (0.64 g, 69%).

$^1$H NMR (300 MHz, MeOD); 6.82 (2H, s), 4.17 (2H, t), 3.79 (3H, s), 3.59 (2H, t), 2.67 (4H, s), 1.95 (2H, dt). m/z [M+H]$^+$=270.2.

Methyl (2-(2-oxopyrrolidin-1-yl)ethyl) fumarate (38)

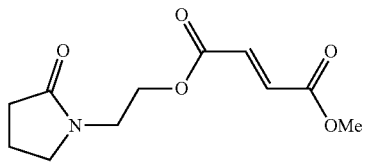 [SMILES: COC(=O)/C=C/C(=O)OCCN1CCCC1=O]

Methyl (2-(2-oxopyrrolidin-1-yl)ethyl) fumarate 38 was synthesised from 1-(2-hydroxyethyl)pyrrolidin-2-one following general procedure 1 (0.68 g, 73%).

$^1$H NMR (300 MHz, MeOD); 6.85 (2H, s), 4.33 (2H, t), 3.80 (3H, s), 3.59 (2H, t), 3.46 (2H, t), 2.37 (2H, t), 2.03 (2H, dt). [M+H]$^+$=242.1.

Methyl (2-(2-oxooxazolidin-3-yl)ethyl) fumarate (39)

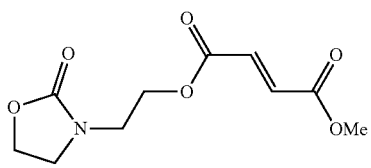 [SMILES: COC(=O)/C=C/C(=O)OCCN1CCOC1=O]

Methyl (2-(2-oxooxazolidin-3-yl)ethyl) fumarate 39 was synthesised from 3-(2-hydroxyethyl)oxazolidin-2-one following general procedure 1 (0.77 g, 92%).

$^1$H NMR (300 MHz, MeOD); 6.82 (2H, s), 4.39-4.30 (4H, m), 3.78 (3H, s), 3.72-3.67 (2H, m), 3.58-3.54 (2H, m). m/z [M+H]$^+$=244.2.

2-(4,4-Dimethyl-2,5-dioxoimidazolidin-1-yl)ethyl methyl fumarate (42)

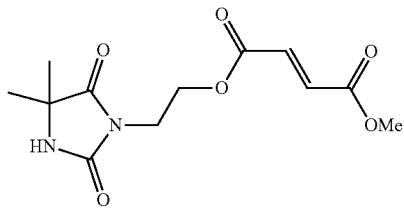 [SMILES: COC(=O)/C=C/C(=O)OCCN1C(=O)NC(C)(C)C1=O]

2-(4,4-Dimethyl-2,5-dioxoimidazolidin-1-yl)ethyl methyl fumarate 42 was synthesised from 3-(2-hydroxyethyl)-5,5-dimethylimidazolidine-2,4-dione following general procedure 1 (0.33 g, 33%).

$^1$H NMR (300 MHz, CDCl$_3$); 6.82 (2H, s), 5.50 (NH), 4.40 (2H, t), 3.86-3.76 (5H, m), 1.43 (6H, s). m/z [M+H]$^+$= 285.2.

Methyl (2-(N-propionylpropionamido)ethyl) fumarate (42)

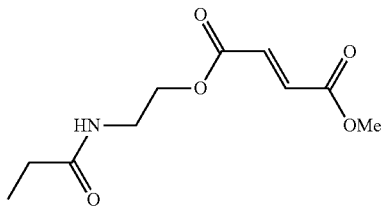 [SMILES: CCC(=O)NCCOC(=O)/C=C/C(=O)OC]

Methyl (2-propionamidoethyl) fumarate 41 was synthesised from N-(2-hydroxyethyl)propionamide following general procedure 1 (1.7 g, 96%).

$^1$H NMR (300 MHz, CDCl$_3$); 6.87 (2H, s), 4.29 (2H, t), 3.81 (3H, s), 3.58 (2H, q), 2.21 (2H, q), 1.15 (3H, t).

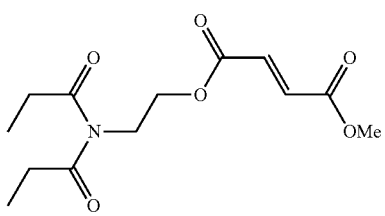 [SMILES: CCC(=O)N(CCOC(=O)/C=C/C(=O)OC)C(=O)CC]

A mixture of methyl (2-propionamidoethyl) fumarate (1.7 g, 7.4 mmol), propionic anhydride (36 mL) and sodium propionate (1.0 g, 10.4 mmol) was heated at 150° C. for 16 h. The reaction was cooled, concentrated to ⅓$^{rd}$ volume and then loaded onto a silica column and eluted with 0-20% ethyl acetate/dichloromethane. The product containing fractions were combined, evaporated and re-purified by silica flash chromatography eluting with 10-50% ethyl acetate/heptanes giving methyl (2-(N-propionylpropionamido)ethyl) fumarate 42 (0.18 g, 21%).

$^1$H NMR (300 MHz, CDCl$_3$); 6.83-6.82 (2H, m), 4.34 (2H, t), 4.01 (2H, t), 3.81 (3H, s), 2.75 (4H, q), 1.16 (6H, t).

2-((3R,4S)-3,4-Dimethyl-2,5-dioxopyrrolidin-1-yl)ethyl methyl fumarate (23)

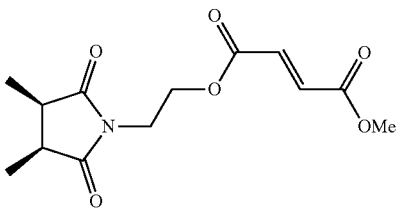 [SMILES: COC(=O)/C=C/C(=O)OCCN1C(=O)[C@@H](C)[C@@H](C)C1=O]

Racemic 2-((3R,4S)-3,4-dimethyl-2,5-dioxopyrrolidin-1-yl)ethyl methyl fumarate 23 was synthesised from racemic (3R,4S)-1-(2-hydroxyethyl)-3,4-dimethylpyrrolidine-2,5-dione following general procedure 1 (0.54 g, 44%).

$^1$H NMR (300 MHz, CDCl$_3$); 6.81-6.80 (2H, m), 4.37 (2H, t), 3.82 (2H, t), 3.80 (3H, s), 3.00-2.88 (2H, m), 1.25-1.18 (6H, m). m/z [M+H]$^+$=284.2.

2-Acetamidoethyl methyl fumarate (43)

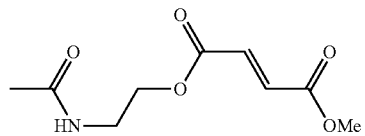

2-Acetamidoethyl methyl fumarate was synthesised from N-(2-hydroxyethyl)acetamide 43 following general procedure 1 (0.23 g, 70%).

$^1$H NMR (300 MHz, CDCl$_3$); 6.87 (2H, s), 5.80 (NH), 4.29 (2H, t), 3.81 (3H, s), 3.57 (2H, q), 2.00 (3H, s). m/z [M+H]$^+$=216.14.

2-(N-Acetylacetamido)ethyl methyl fumarate (44)

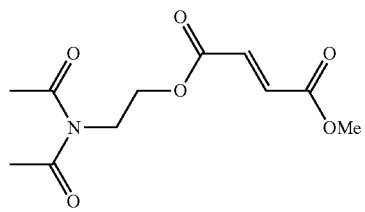 [SMILES: COC(=O)/C=C/C(=O)OCCN(C(C)=O)C(C)=O]

A mixture of 2-acetamidoethyl methyl fumarate (0.62 g, 2.9 mmol), acetic anhydride (15 mL) and sodium acetate (0.33 g, 4.0 mmol) was heated at reflux for 20 h. The reaction mixture was evaporated and the residue suspended in dichloromethane. The supernatant was loaded onto a silica column and eluted with 0-205 ethyl acetate/dichloromethane giving 2-(N-Acetylacetamido)ethyl methyl fumarate 44 (0.36 g, 48%).

$^1$H NMR (300 MHz, CDCl$_3$); 6.87 (1H, d), 6.82 (1H, d), 4.36 (2H, d), 4.00 (2H, d), 3.81 (3H, s), 2.44 (3H, s).

2-((tert-butoxycarbonyl)amino)ethyl methyl fumarate (48)

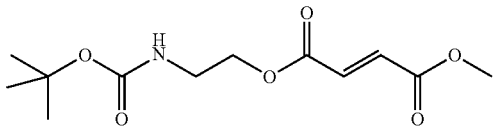 [SMILES: COC(=O)/C=C/C(=O)OCCNC(=O)OC(C)(C)C]

To a suspension of monomethyl fumarate (MMF) (1.0 equivalent) in dichloromethane (11 mL per g of MMF) was added diisopropylethylamine (3 equivalents), 2-((tert-butoxylcarbonyl)amino)ethanol (1.02 equivalents) and N,N,N',N'-tetramethyl-O-(1H-benzotriazol-1-yl)uronium tetrafluoroborate (1.5 equivalents). The reaction was stirred for 1-18 hours at <10° C. The reaction was quenched with 1M hydrochloric acid (0.6 mL/mL of DCM). The organic layer was washed with 10% (w/w) aqueous sodium bicarbonate solution (0.6 mL/mL of DCM) followed by 37% (w/w) sodium chloride solution (0.6 mL/mL of DCM). The organic layer was dried over sodium sulfate, filtered to remove the drying agent, and the solution added to a silica plug (~6 g of silica gel/g of MMF) and the plug flushed with DCM until no more product eluted. ~80% of the DCM was removed under reduced pressure at 30° C. after which time 25 mL of MTBE/g of MMF were added and the solution further concentrated at 30° C. until ~10 mL/g of MMF remained. The resulting suspension was cooled to 5° C. for at least 1 hour and then the resulting solids were collected by filtration to give the desired MMF ester prodrug. (3.8 g, 91%).

$^1$H NMR (400 MHz, DMSO-$d_6$) δ 7.08 (t, J=5.4 Hz, 1H), 6.89 (d, J=15.8 Hz, 1H), 6.79 (d, J=15.8 Hz, 1H), 4.18 (t, J=5.3 Hz, 2H), 3.81 (s, 3H), 3.28 (q, J=5.4 Hz, 2H), 1.43 (s, 9H). m/z [M+H]+=274.3.

2-(2,5-dioxo-2,5-dihydro-1H-pyrrol-1-yl)ethyl methyl fumarate (55)

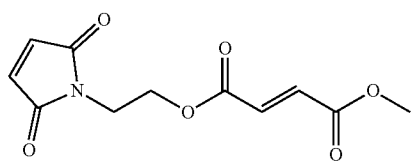 [SMILES: COC(=O)/C=C/C(=O)OCCN1C(=O)C=CC1=O]

To a suspension of monomethyl fumarate (MMF) (1.0 equivalent) in dichloromethane (11 ml per g of MMF) was added diisopropylethylamine (3 equivalents), the desired alcohol (1.02 equivalents) and N,N,N',N'-tetramethyl-O-(1H-benzotriazol-1-yl)uronium tetrafluoroborate (1.5 equivalents). The reaction was stirred for 1-18 hours at <10° C. The reaction was quenched with 1M hydrochloric acid (0.6 mL/mL of DCM). The organic layer was washed with 10% (w/w) aqueous sodium bicarbonate solution (0.6 mL/mL of DCM) followed by 37% (w/w) sodium chloride solution (0.6 mL/mL of DCM). The organic layer was dried over sodium sulfate, filtered to remove the drying agent, and the solution added to a silica plug (~6 g of silica gel/g of MMF) and the plug flushed with DCM until no more product eluted. ~80% of the DCM was removed under reduced pressure at 30° C. after which time 25 mL of MTBE/g of MMF were added and the solution further concentrated at 30° C. until ~10 mL/g of MMF remained. The resulting suspension was cooled to 5° C. for at least 1 hour and then the resulting solids were collected by filtration to give the desired MMF ester prodrug. (2.4 g, 67%).

$^1$H NMR (400 MHz, Chloroform-d) δ 6.82 (d, J=2.8 Hz, 2H), 6.74 (s, 2H), 4.36 (t, J=5.3 Hz, 2H), 3.86 (t, J=5.3 Hz, 2H), 3.81 (s, 3H). m/z [M+H]+=254.2.

Reference Compound A 2-(diethylamino)-2-oxoethyl methyl fumarate

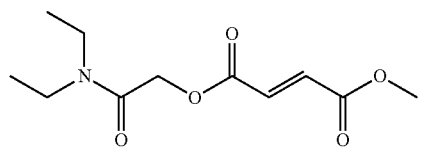 [SMILES: CCN(CC)C(=O)COC(=O)/C=C/C(=O)OC]

2-(diethylamino)-2-oxoethyl methyl fumarate was synthesized following general procedure 3 and conformed to reported data in U.S. Pat. No. 8,148,414.

Example 2—Aqueous Chemical Stability of Several Compounds

Stock solutions of the compounds in acetonitrile or acetonitrile/methanol were prepared at 20 mg/mL and 20 μL, spiked into 3 mL of buffer phosphate (100 mM) and incubated at 37° C. Aliquots (50 μL) were sampled at different time points and diluted 20 fold with ammonium formate (pH 3.5)/acetonitrile. The diluted samples were analyzed by HPLC. The peak areas corresponding to the compounds were plotted against time and the data were fitted to a first-order mono-exponential decay where the rate constant and the half-life were determined (Table 3). In some cases, in which the half life is too long (>360 min), an estimated value of the half life is reported using the initial slope at low conversion (<10%).

TABLE 3

| Compound | pH 8 (t½, min) |
| --- | --- |
| 1 | 15 |
| 4 | 45 |
| 5 | 24 |
| 6 | 2.0 |
| 7 | 26.0 |
| 8 | 36.0 |
| 9 | 7.0 |
| 10 | 67.0 |
| 11 | >240 |
| 12 | 396 |
| 14 | 144 |
| 15 | 3.0 |
| 16 | 20.0 |
| 17 | 11.0 |
| 18 | 5.0 |
| 19 | 6.0 |
| 20 | 5.0 |
| Reference Compound A | 120 |

Stock solutions of the compounds in acetonitrile or acetonitrile/MeOH were prepared at 0.05M. A 0.010 mL aliquot of the stock was spiked into 1 mL of 50 mM buffer phosphate pH 8 and incubated at 37° C. Typically, aliquots (0.010 mL) were sampled at different time points and immediately injected in the HPLC with UV detection (211 nm). The peak areas corresponding to the compounds were plotted against time and the data were fitted to a first-order mono-exponential decay where the rate constant and the half-life were determined from the slope (Table 4).

TABLE 4

| Compound | pH 8 (t½, min) |
|---|---|
| 1 | 15 |
| 4 | 30 |
| 5 | 24 |
| 6 | 2 |
| 19 | 117 |
| 22 | 144 |
| 23 | 186 |
| 26 | 129 |
| 27 | 37 |
| 28 | <10 |
| 29 | <10 |
| 30 | 229 |
| 31 | 26 |
| 32 | 13 |
| 33 | 115 |
| 35 | |
| 37 | 182 |
| 38 | 201 |
| 39 | 183 |
| 40 | 203 |
| 42 | 158 |
| 43 | 177.5 |
| 44 | 145 |
| 48 | 220 |
| 130 | 1010 |
| 131 | 96 |
| 133 | 246 |

Example 3—Evaluation of Aqueous Chemical Stability with NMR

The chemical hydrolysis was followed by dissolving the ester in phosphate buffered $D_2O$ (pH 7.9) in an NMR tube, heating the NMR tube to 37° C. and periodically recording the spectra. These various species produced by hydrolysis of the diesters were followed over time. See FIGS. 1-5.

Example 4—Delivery of MMF in Rats Upon Oral Administration of Prodrugs

Rats were obtained commercially and were pre-cannulated in the jugular vein. Animals were conscious at the time of the experiment. All animals were fasted overnight and until 4 hours post-dosing of a prodrug in the disclosure.

Blood samples (0.25 mL/sample) were collected from all animals at different time-points up to 24 hours post-dose into tubes containing sodium fluoride/sodium EDTA. Samples were centrifuged to obtain plasma. Plasma samples were transferred to plain tubes and stored at or below −70° C. prior to analysis.

To prepare analysis standards, 20 uL of rat plasma standard was quenched with 60 uL of internal standard. The sample tubes were vortexed for at least 1 min and then centrifuged at 3000 rpm for 10 min. 50 uL of supernatant was then transferred to 96-well plates containing 100 μL water for analysis by LC-MS-MS.

LC-MS/MS analysis was performed using an API 4000 equipped with HPLC and autosampler. The following HPLC column conditions were used: HPLC column: Waters Atlantis T3; flow rate 0.5 mL/min; run time 5 min; mobile phase A: 0.1% formic acid in water; mobile phase B: 0.1% formic acid in acetonitrile (ACN); gradient: 98% A/2% B at 0.0 min; 98% A/2% B at 1 min; 5% A/95% B at 3 min; 5% A/95% B at 3.75 min; 97% A/3% B at 4 min; and 98% A/2% B at 5.0 min. MMF was monitored in positive ion mode.

MMF, DMF or MMF prodrug was administered by oral gavage to groups of two to six adult male Sprague-Dawley rats (about 250 g). Animals were conscious at the time of the experiment. MMF, DMF or MMF prodrug was orally administered in an aqueous solution of 0.5% hydroxypropyl methyl cellulose (HPMC), 0.02% polysorbate 80, and 20 mM citrate buffer (pH 5), at a dose of 10 mg-equivalents MMF per kg body weight.

The percent absolute bioavailability (F %) of MMF was determined by comparing the area under the MMF concentration vs time curve (AUC) following oral administration of MMF, DMF or MMF prodrug with the AUC of the MMF concentration vs time curve following intravenous administration of MMF on a dose normalized basis.

The MMF prodrugs, when administered orally to rats at a dose of 10 mg/kg MMF-equivalents in the aqueous vehicle, exhibited an absolute oral bioavailability (relative to IV) ranging from about 3% to about 96% (See Tables 5 and 6). Tables 5 and 6 show data from two independent studies.

TABLE 5

| Compound No. | Percent Absolute Bioavailability (F %) |
|---|---|
| MMF | 43% |
| DMF | 53% |
| 16 | 60-82% |
| 4 | 3% |
| 14 | 96% |
| 10 | 73% |

TABLE 6

| Compound No. | Percent Absolute Bioavailability (F %) |
|---|---|
| MMF | 69.6 |
| DMF | 69.6 |
| 132 | 60.3 |
| 40 | 70.4 |
| 39 | 91.4 |
| 5 | 81.1 |
| 11 | 71.4 |

Example 5—Delivery of MMF in Dogs Upon Oral Administration of Prodrugs

Male Beagle dogs were obtained from the test facility's colony of non-native animals. All animals were fasted overnight prior to dose administration.

Oral doses were administered via oral gavage. The gavage tube was flushed with 10 mL of water prior to removal.

All animals were observed at dosing and at each scheduled collection. All abnormalities were recorded.

Blood samples were collected in Sodium Fluoride/$Na_2$EDTA tubes and stored on wet ice until processed to plasma by centrifugation (300 rpm at 5° C.) within 30 minutes of collection. All plasma samples were transferred into separate 96-well plates (matrix tubes) and stored at −80° C. until concentration analysis was performed via LC/MS/MS using an RGA 3 assay.

Extraction Procedure:
Note: Thawed test samples at 4° C. (Kept in ice while on bench).
1. Aliquoted 20 uL of study sample, standard, and QC samples into labeled 96-well plate.
2. Added 120 uL of appropriate internal standard solution (125 ng/mL mouse embryo fibroblasts (MEF)) to each tube, except for the double blank to which 120 uL of appropriate acetonitrile:FA (100:1) was added.
3. Sealed and vortexed for one minute.
4. Centrifuged at 3000 rpm for 10 minutes.
5. Transferred 100 uL of supernatant to a clean 96-well plate containing 100 uL water.
6. Sealed and vortexed gently for 2 minutes.

The percent absolute bioavailability (F %) of MMF was determined by comparing the area under the MMF concentration vs time curve (AUC) following oral administration of MMF prodrug with the AUC of the MMF concentration vs time curve following intravenous administration of MMF on a dose normalized basis.

The MMF prodrugs, when administered orally to dogs at a dose of 10 mg/kg MMF-equivalents in the aqueous vehicle, exhibited an absolute oral bioavailability (relative to IV) ranging from about 31% to about 78% (See Table 7).

TABLE 7

| Compound No. | Percent Absolute Bioavailability (F %) |
|---|---|
| 16 | 54% |
| 16 (capsule) | 54% |
| 14 | 78% |
| 10 | 31% |

Figure 6:
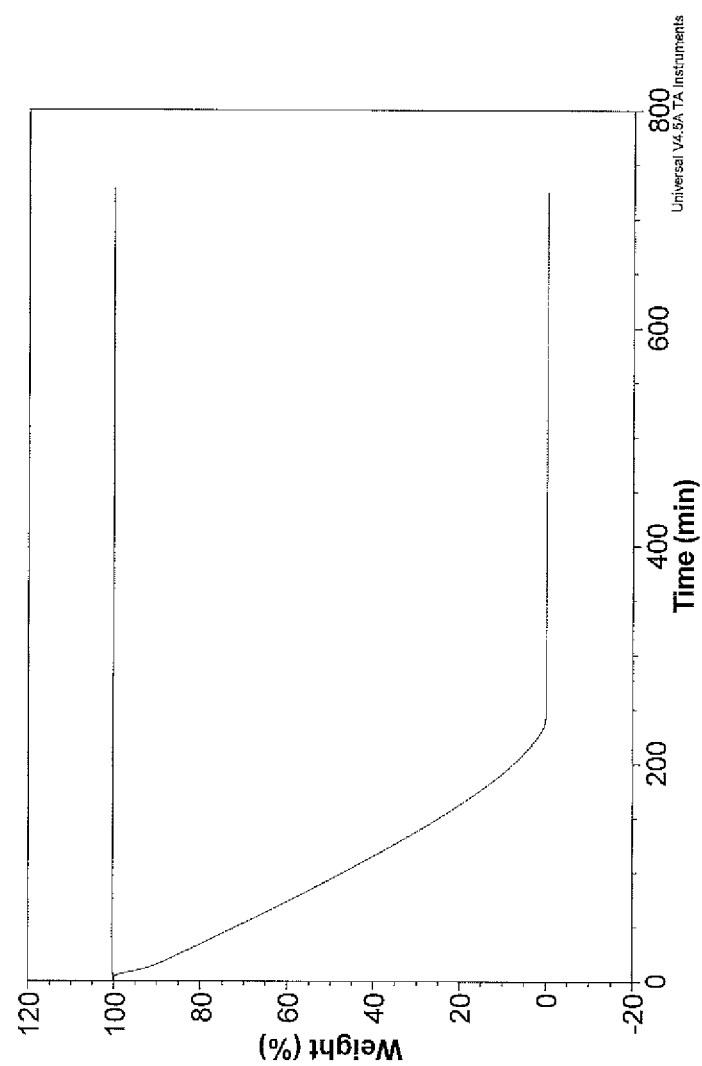
FIG. 6 depicts a plot of weight loss vs time for Compound 14 and DMF.

Example 6—Physical Stability of the Instant Prodrugs and DMF in Crystalline Form The physical stability of compounds of the present invention and DMF were measured via thermogravimetric analysis (TGA). FIG. 6 shows a plot of weight loss at 60° C. vs time for Compound 14 (12.15 mg), no change, and DMF (18.40 mg), ~100% weight loss in less than 4 hours. These data indicate that DMF undergoes sublimation while Compound 14 is physically stable under similar conditions.

Example 7—Single Crystal X-Ray Data for Compound 14

Figure 7:
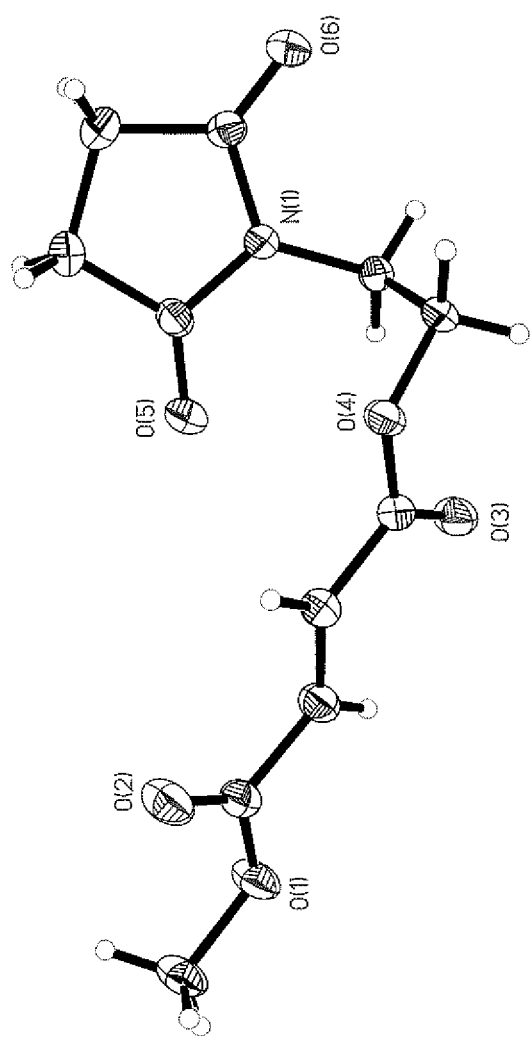
FIG. 7 depicts the unit cell for crystalline Compound 14.

Compound 14 produced by the method described in Example 1 was analyzed. FIG. 7 depicts the unit cell. The single crystal x-ray data are included below:

Single crystal data:
Empirical formula: C11 H13 N O6
Formula weight: 255.22
Temperature: 173(2) K
Wavelength: 1.54178 Å
Space group: P-1
Unit cell dimensions:

| a = 6.07750(10) Å | α = 84.9390(10)°. |
|---|---|
| b = 7.96290(10) Å | β = 80.0440(10)°. |
| c = 12.7850(2) Å | γ = 71.9690(10)°. |

Volume: 579.080(15) Å$^3$
Z: 2
Density (calculated): 1.464 Mg/m$^3$
Absorption coefficient: 1.034 mm$^{-1}$
F(000): 268
Crystal size: 0.37×0.15×0.15 mm$^3$
Reflections collected: 8446
Independent reflections: 2229 [R(int)=0.0249]
Refinement method: Full-matrix least-squares on F$^2$
Goodness-of-fit on F$^2$:1.049
Final R indices [I>2sigma(I)] R1=0.0317, wR2=0.0850
R indices (all data): R1=0.0334, wR2=0.0864.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the formula

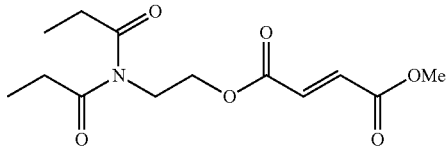 [SMILES: CCC(=O)N(CCOC(=O)/C=C/C(=O)OC)C(=O)CC]

or a pharmaceutically acceptable salt thereof.

2. A pharmaceutical composition comprising the compound of claim 1, or a pharmaceutically acceptable salt thereof.

3. A method of treating multiple sclerosis in a subject in need thereof, comprising administering to the subject a therapeutically effective amount of the compound of claim 1.

4. A method of treating multiple sclerosis in a subject in need thereof, comprising administering to the subject a therapeutically effective amount of a composition of claim 2.

* * * * *